(12) United States Patent
Hromas et al.

(10) Patent No.: US 8,889,689 B2
(45) Date of Patent: Nov. 18, 2014

(54) BIFUNCTIONAL METNASE/INTNASE INHIBITORS AND RELATED COMPOSITIONS AND METHODS OF TREATMENT OF CANCER

(75) Inventors: Robert Hromas, Gainesville, FL (US); Andrei Leitao, Sao Carlos (BR); Tudor I. Oprea, Albuquerque, NM (US); Larry A. Sklar, Albuquerque, NM (US); Elizabeth A. Williamson, Gainesville, FL (US); Justin Wray, Albuquerque, NM (US); Wei Wang, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 13/574,941

(22) PCT Filed: Jan. 26, 2011

(86) PCT No.: PCT/US2011/022508
§ 371 (c)(1),
(2), (4) Date: Jul. 24, 2012

(87) PCT Pub. No.: WO2011/094260
PCT Pub. Date: Aug. 4, 2011

(65) Prior Publication Data
US 2012/0302582 A1    Nov. 29, 2012

Related U.S. Application Data

(60) Provisional application No. 61/336,754, filed on Jan. 26, 2010, provisional application No. 61/305,705, filed on Feb. 18, 2010.

(51) Int. Cl.
| | |
|---|---|
| *A61K 31/497* | (2006.01) |
| *A61K 45/06* | (2006.01) |
| *C07D 401/12* | (2006.01) |
| *C07D 215/56* | (2006.01) |
| *A61K 31/4709* | (2006.01) |
| *A61K 31/47* | (2006.01) |

(52) U.S. Cl.
CPC .............. *C07D 215/56* (2013.01); *A61K 45/06* (2013.01); *C07D 401/12* (2013.01); *A61K 31/4709* (2013.01); *A61K 31/47* (2013.01)
USPC .................................................. 514/253.08

(58) Field of Classification Search
CPC . A61K 31/47; A61K 31/4709; C07D 215/56; C07D 215/233
USPC .................................................. 514/253.08
See application file for complete search history.

(56) References Cited

U.S. PATENT DOCUMENTS 5,854,227 A    12/1998    Hartmann

FOREIGN PATENT DOCUMENTS

WO    03084475 A2    10/2003

OTHER PUBLICATIONS

Lucero et al 'Synthesis and anti-HSV-1 activity of quinolonic acyclovir analogues' Bioorganic and Medicinal Chemistry Letters, vol. 16, p. 1010-1013, 2006.*
Greene TW and WUTS PGM; Protective Groups in Organic Synthesis, Third Edition; John Wiley, New York, 1999.
Bostrom J, Greenwood Jr, and Gottfries J; Assessing the performance of OMEGA with respect to retrieving bioactive conformations; Journal of Molecular Graphics and Modeling 2003, 21, 449-462.
McGann MR, Almond HR, Nicholls A, Grant JA, and Brown FK; Gaussian Docking Functions; Biopolymers 2003; 68, 76-90.
Wang H et al., Design, synthesis and antitumor activity of 3-substituted quinolone derivatives (I). Chinese Chemical Letters 2008; 19:1395-1397.
Wray J et al., Metnase mediates chromosome decatenation in acute leukemia cells. Blood 2009; 114:1852-1858.
Wray J et al., Metnase Mediates Resistance to Topoisomerase II Inhibitors in Breast Cancer Cells. PloS One 2009; 4: e5323.

* cited by examiner

*Primary Examiner* — Wu-Cheng Winston Shen
*Assistant Examiner* — Christopher R Stone
(74) *Attorney, Agent, or Firm* — Henry D. Coleman; R. Neil Sudol

(57) ABSTRACT

This invention relates to novel cancer treatment compositions and associated therapeutic methods. More particularly, this invention relates in part to small chemical bifunctional inhibitors of DNA replication and repair proteins Metnase and/or Intnase (also termed Gypsy Integrase, Gypsy Integrease-1, Gypsy Retransposon Integrase 1, or GIN-I) that simultaneously damage DNA, and to a therapeutic method that utilizes the inhibitors to increase the effectiveness of cancer treatment protocols, including radiation therapy. In preferred embodiments, compounds, compositions and methods of treatment of the invention are used to treat a patient suffering from leukemia (e.g. acute myeloid leukemia (AML) and related cancers. In certain aspects of such treatments, compounds, compositions and methods of treatment of the invention are administered as a monotherapy (in some cases, to patients who have exhibited resistance to Topo IIalpha inhibitors such as VP-16), or are co-administered with a Topo IIalpha inhibitor or other anti-cancer agents as otherwise described herein or in combination with radiation therapy.

13 Claims, 45 Drawing Sheets

Figure 1
Metnase/Gypsy Integrase Inhibitor
ChemDiv 5483-0023

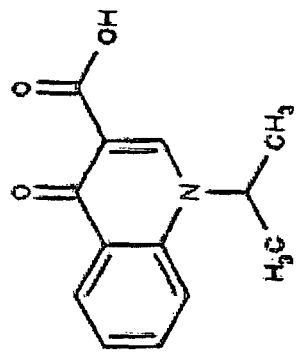

Virtually screening for compounds that can dock within the active site of the transposase domain of Metnase uncovered a family of related compounds, including 5483-0023

The electrostatic surface of the enzyme is displayed on the left: high-electron density regions (red), low-electron density regions (blue), normal density (white). The right panel shows the required magnesium atom (red dot).

5483-0023 decreases proliferation of KG-1 cells on its own and potentiates VP-16

DNA combing shows that Metnase is required for replication fork restart after stalling

FIGURE 4

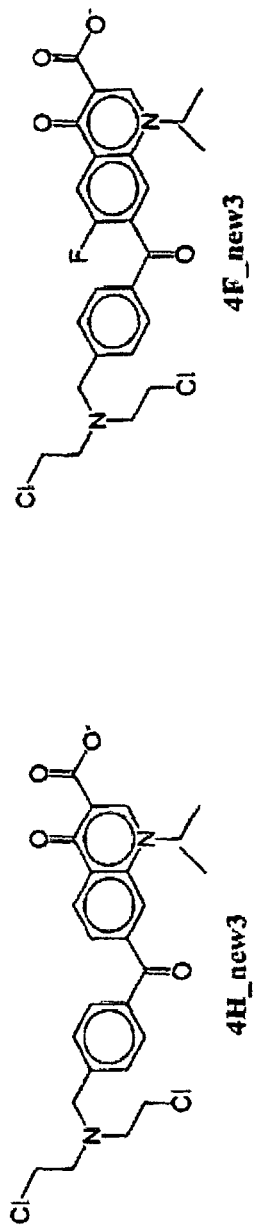

4H_new3

4F_new3

Since Metnase and Gypsy Integrase are required for replication fork progression, and cross-linking DNA stalls replication forks, we generate bi-functional compound that both cross-links DNA using a nitrogen mustard group and docks into the active site of Metnase, to inhibit it. Thus, the cross-linking of DNA will stall a cancer cell's replication fork, while the 5483-0023 transposase domain inhibitor will block the ability Metnase/Gypsy Integrase to re-start the fork.

The binding mode of one possible bifunctional compound depicts two possible binding modes to the Intnase transposase domain. The nitrogen mustard group is too close to the protein to efficiently interact with DNA, therefore further derivatives were generated.

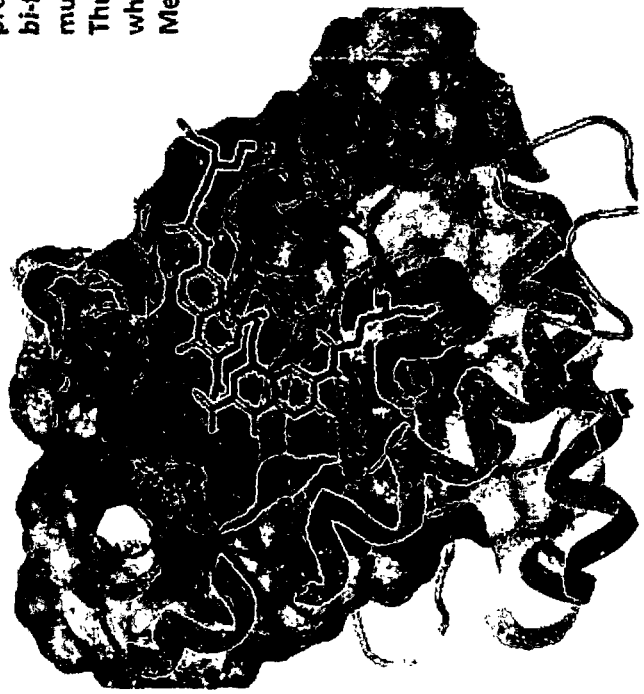

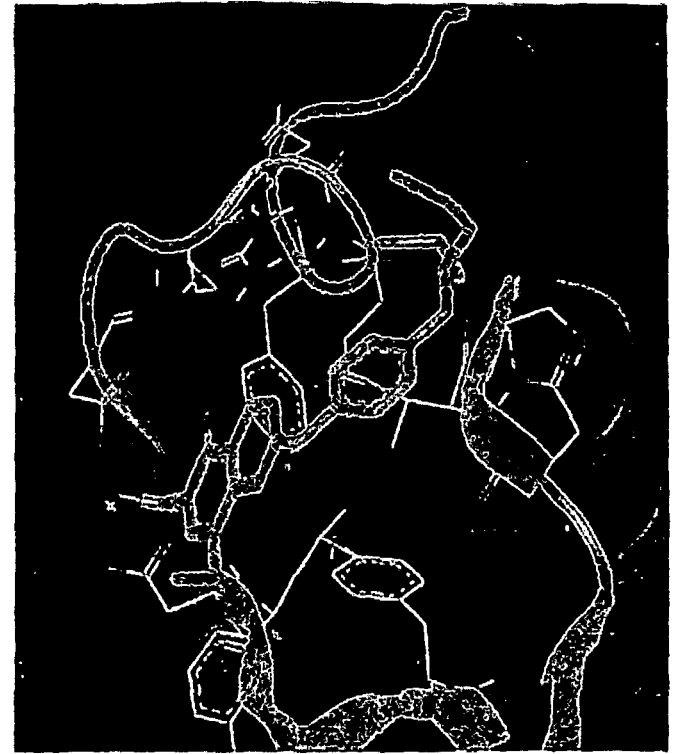
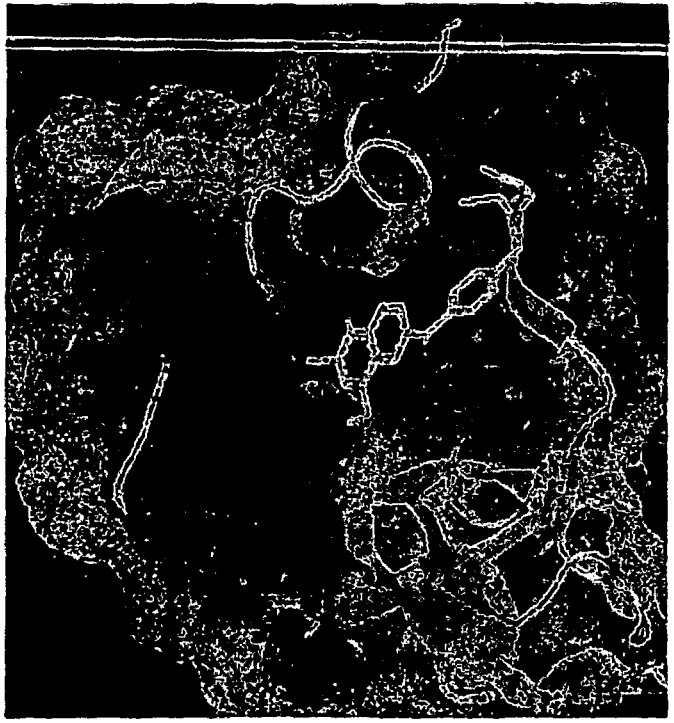
Figure 5
Docking of hypothesized bifunctional compounds into the transposase domain of Intnase.

Docking results of a possible bifunctional compound into the Metnase transposase domain.

Figure 8

Docking of 4H-new5 into the active site of the Metnase Transposase domain shows that the nitrogen mustard domain is free to interact with DNA.

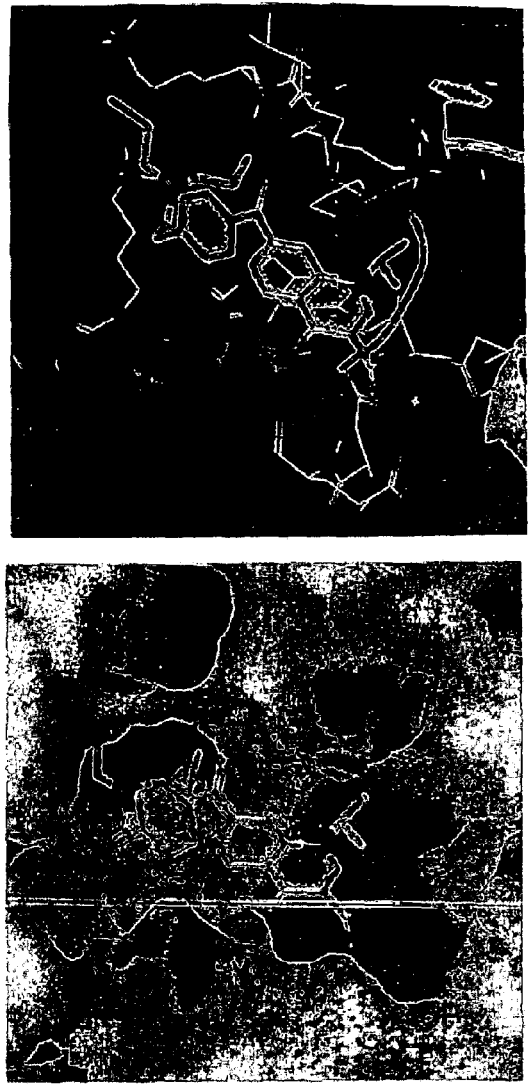

| Name | Total Score | Steric | Desolvation | HB Acc | HB Donor | Metal |
|---|---|---|---|---|---|---|
| 4H_new5 | -77.41 | -58.37 | 7.62 | -1.70 | 0 | -24.96 |
| 5483-0023 | -43.29 | -27.00 | 7.59 | 0 | 0 | -23.87 |

The electrostatic surface of the enzyme is displayed on the left: high-electron density regions (red), low-electron density regions (blue), normal density (white). The metal atom and the catalytic aspartates are shown at the bottom of the pictures on the right. Ligands are depicted as stick figures. Only nearby amino acids (up to 350 pm away from these compounds) are represented as wireframes on the right. Atom colors: oxygen (red), carbon (gray), polar hydrogen (white), nitrogen (blue), fluorine (orange) and chlorine (green). The cartoon representation of the protein depicts helices (red) and loops (gray).

Figure 9
ChemDiv 3731-0098
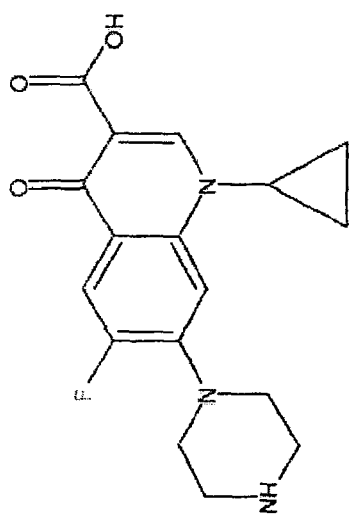
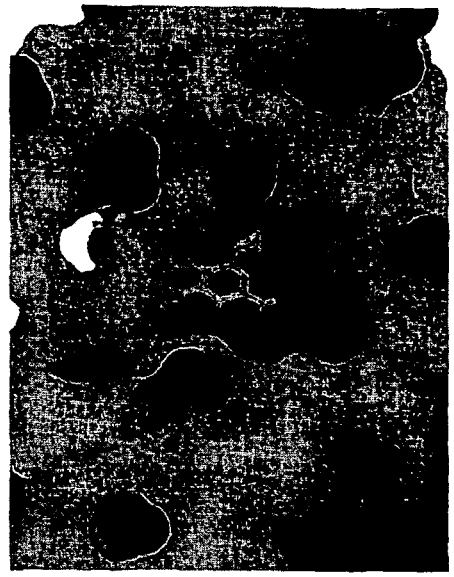
Virtual docking of 3731-0098 in Metnase
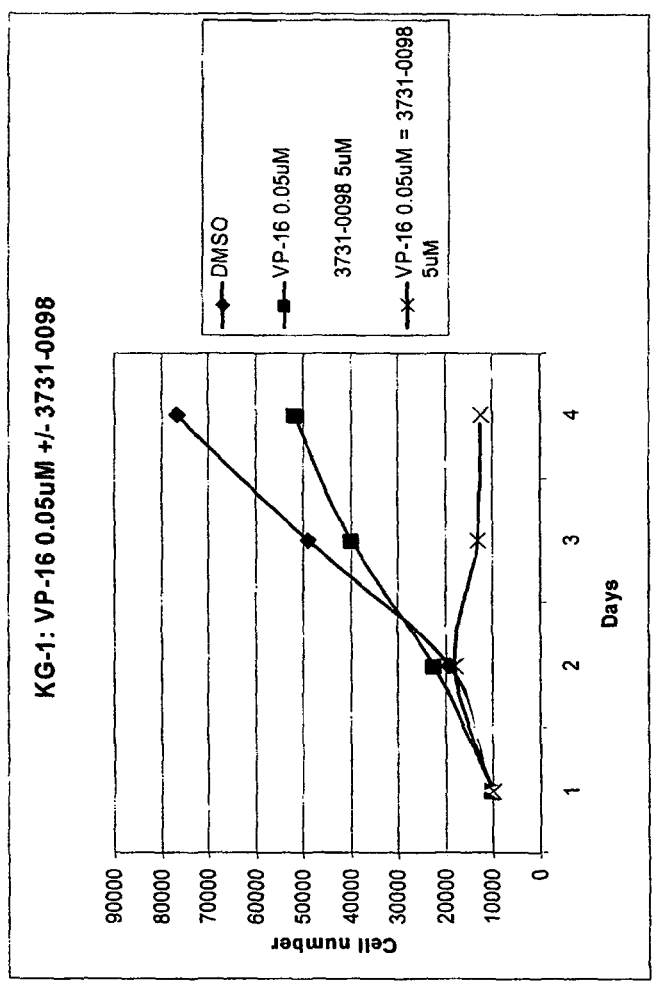

Since Metnase is required for replication fork progression, and cross-linking DNA stalls replication forks, we generated a bi-functional compound that both cross-links DNA and docks into the active site of Metnase, to inhibit it.

Docking of
4H_new5 into
the active site
of the Metnase
Transposase
domain

Figure 11

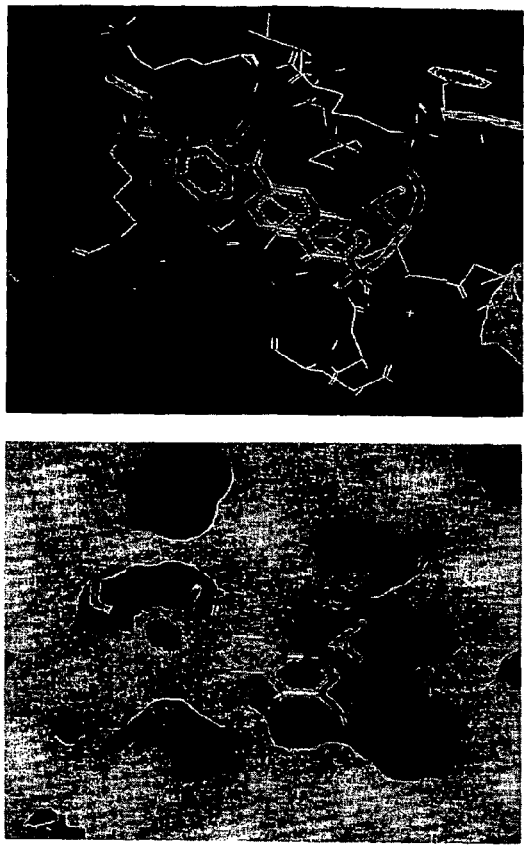

| Name | Total Score | Steric | Desolvation | HB Acc | HB Donor | Metal |
|---|---|---|---|---|---|---|
| 4H_new5-5483-0023 | -77.41 | -58.37 | 7.62 | -1.70 | 0 | -24.96 |
|  | -43.29 | -27.00 | 7.59 | 0 | 0 | -23.87 |

The electrostatic surface of the enzyme is displayed on the left: high-electron density regions (red), low-electron density regions (blue), normal density (white). The metal atom and the catalytic aspartates are shown at the bottom of the pictures on the right. Ligands are depicted as stick figures. Only nearby amino acids (up to 350 pm away from these compounds) are represented as wireframes on the right. Atom colors: oxygen (red), carbon (gray), polar hydrogen (white), nitrogen (blue), fluorine (orange) and chlorine (green). The cartoon representation of the protein depicts helices (red) and loops (gray).

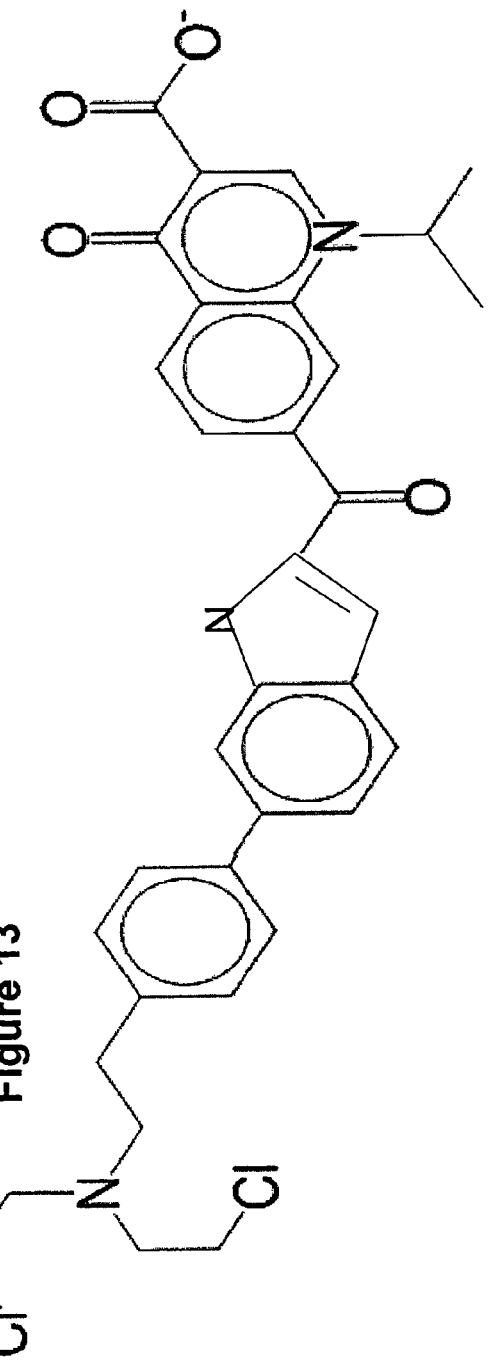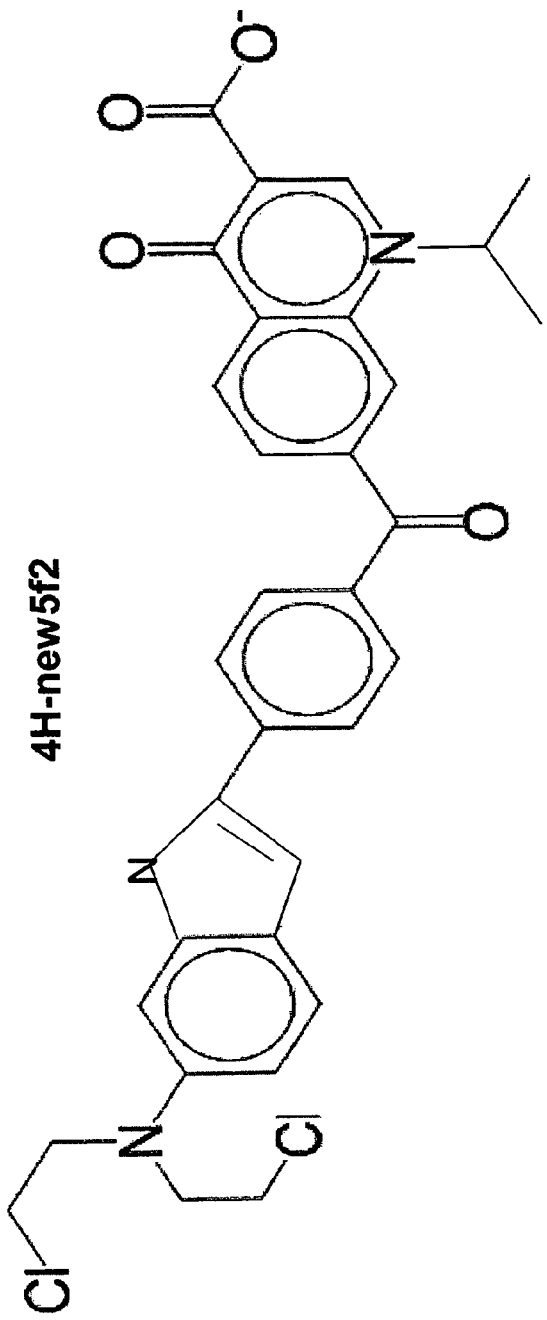
Figure 13

4H-new5H1

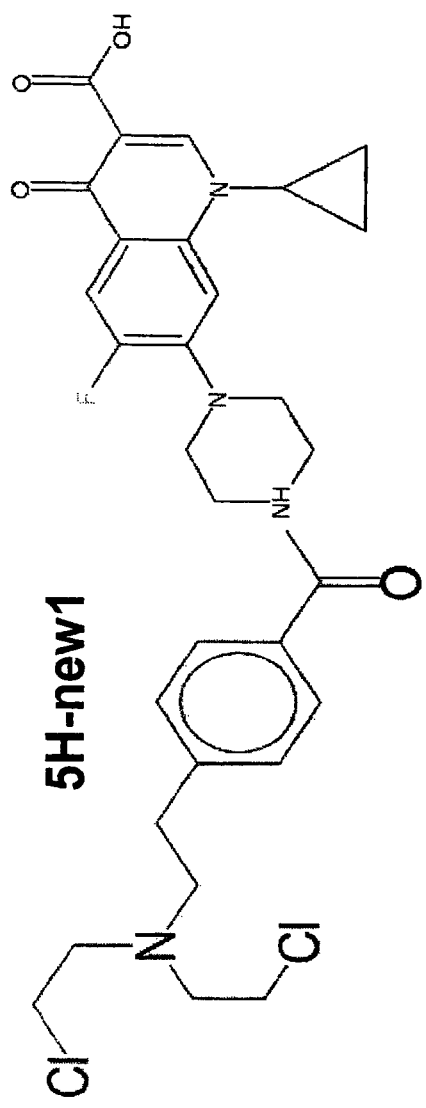# 
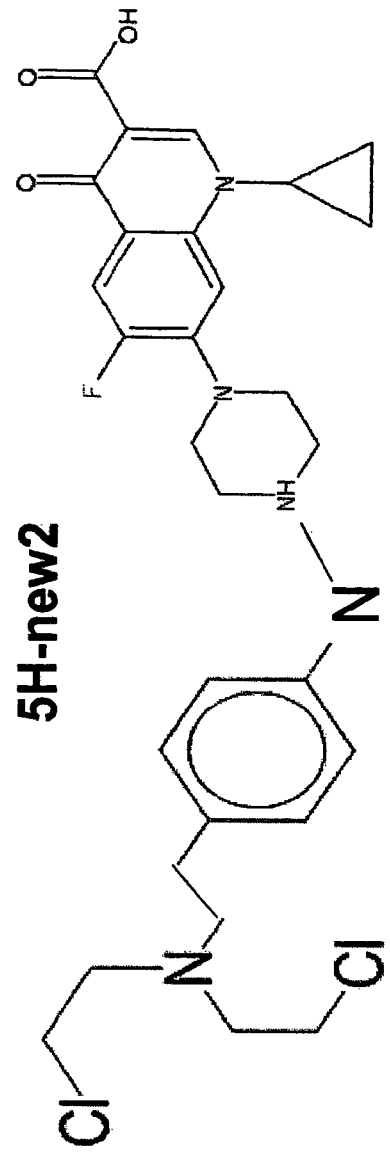
Figure 15

5H-new3

A549: Z641-0011 (chronic)

A549: Z641-0013 Overnight +/- Cisplatin n=3

A549: Z641-0013 Overnight n=3

BIFUNCTIONAL METNASE/INTNASE INHIBITORS AND RELATED COMPOSITIONS AND METHODS OF TREATMENT OF CANCER

This application is a United States national phase application based upon and claiming priority from International Patent Application No. PCT/US2011/022508, filed Jan. 26, 2011, said application claims the benefit of priority of U.S. provisional application numbers US61/336,754, filed Jan. 26, 2010, and US61/305,705, filed Feb. 18, 2010, all three of which applications entitled "Novel Bifunctional Metnase/Intnase Inhibitors and Related Compositions and Methods of Treatment", all three of which applications are incorporated by reference in their entirety herein.

RELATED APPLICATIONS AND GOVERNMENT INTEREST

This patent application was supported by Grant RO1 HL093606 from the National Institutes of Health. The Government has certain rights in the invention.

FIELD OF THE INVENTION

This invention relates to novel cancer treatment compositions and associated therapeutic methods. More particularly, this invention relates in part to small chemical bifunctional inhibitors of DNA replication and repair proteins Metnase (also termed SETMAR) and/or Intnase (also termed Gypsy Integrase, Gypsy Integrase-1, Gypsy Retransposon Integrase 1, or GIN-1) and to a therapeutic method that utilizes the inhibitors to increase the effectiveness of cancer treatment protocols.

In preferred embodiments, compounds, compositions and methods of treatment of the invention are used to treat a patient suffering from leukemia (e.g. acute myeloid leukemia (AML). In certain aspects of such treatments, compounds, compositions and methods of treatment of the invention are administered as a monotherapy (in some cases, to patients who have exhibited resistance to Topo IIalpha inhibitors such as VP-16), or are co-administered with a Topo IIalpha inhibitor or other cancer therapies.

BACKGROUND OF THE INVENTION

Most cancer chemotherapy and radiation therapy kills cancer cells by damaging their DNA and preventing DNA replication. Cancer cells resist therapy and relapse by increasing their ability to repair their DNA and then proceed to replicate their DNA. Identifying the DNA repair proteins that cancer cells use to repair their DNA after therapy would provide new targets to enhance therapy and prevent relapse. Small chemical inhibitors of those target DNA repair and replication proteins could prevent cancer cells from escaping therapy.

We previously demonstrated that Metnase is important for DNA repair. We have now found that is required for DNA replication fork re-start after stalling. Replication forks can stall at sites of cross-linked DNA. We previously generated a class of Metnase and Intnase (also termed Gypsy Integrase, a related protein required for DNA replication) inhibitors that dock into their transpoase domains, which are similar to the retroviral integrase family of proteins. By connecting a potent Metnase inhibitor with a nitrogen mustard DNA alkylating agent we can both create a drug that would be much more difficult for cancer cells to deal with. In one molecule DNA is cross-linked by the nitrogen mustard group, which would stall replication forks, and at the same time, Metnase is inhibited, which is required to re-start stalled replication forks. This would inhibit the very mechanism by which the cell would deal with the cross linked DNA.

OBJECTS OF THE INVENTION

It is an object of the present invention to provide a novel composition or group of related compositions that are useful in the treatment of cancer.

It is a more particular object of the present invention to provide a novel composition or group of related compositions that are useful in inhibiting the DNA repair proteins that aid cancer cells in resisting therapy and relapse.

It is yet another object of the present invention to provide novel pharmaceutical compositions which combine bifunctional inhibitors of Metnase and/or Intnase with a traditional anticancer agent.

It is a further object of the invention to provide combination therapies which utilize bifunctional inhibitors of Metnase and Intnase as described herein in combination with a traditional anticancer agent or other therapy, especially including radiation therapy in the treatment of cancer.

Another object of the present invention is to provide associated cancer treatment protocols and therapies.

Any one or more of these and/or other objects of the present invention will be apparent from the drawings and descriptions herein.

BRIEF DESCRIPTION OF THE FIGURES

FIG. 1. Virtually screening for compounds that can dock within the active site of the transposase domain of Metnase uncovered a family of related compounds, including the compound 5483-0023. The electrostatic surface of the enzyme is displayed on the left: high-electron density regions (red), low-electron density regions (blue), normal density (white). The right panel shows the required magnesium atom (red dot).

FIG. 4. Since Metnase is required for replication fork restart after stalling, and DNA cross-links stall replication forks, fusing the Metnase inhibitor 5483-0023 with a nitrogen mustard group that cross-links DNA into a bifunctional anti-cancer drug would both stall replication forks and block their restart in cancer cells. This figure shows two possible bifunctional agents 4H_new3 and 4F_new3, and the docking of 4H_new3 into the transposase active site of Intnase in two possible conformations. Adding the fluorine group onto 4H_new3 to make 4F_new3 may allow these bifunctional agents to be administered orally by preventing P450 hepatic inactivation of the intestinally absorbed product.

FIG. 5. This also demonstrates one of the docking modes of 4H_new3 into the active site of Intnase using other models.

FIG. 8 illustrates how docking of 4H-new5 into the active site of the Metnase Transposase domain leaves the nitrogen mustard domain free to interact with DNA. The electrostatic surface of the enzyme is displayed on the left: high-electron density regions (red), low-electron density regions (blue), normal density (white). The metal atom and the catalytic aspartates are shown at the bottom of the pictures on the right. Ligands are depicted as stick figures. Only nearby amino acids (up to 350 pm away from these compounds) are represented as wireframes on the right. Atom colors: oxygen (red), carbon (gray), polar hydrogen (white), nitrogen (blue), fluorine (orange) and chlorine (green). The cartoon representation of the protein depicts helices (red) and loops (gray).

FIG. 9 shows the compound 3731-0098 and its virtual docking in Metnase. This figure also shows that the compound 3731-0098 not only increases the cytotoxic activity of the anti-cancer drug VP-16 in KG-1 leukemia cells, but also has cytotoxic activity on its own.

FIG. 11 shows the docking of 4H_new5 into the active site of the Metnase Transposase domain. The electrostatic surface of the enzyme is displayed on the left: high-electron density regions (red), low-electron density regions (blue), normal density (white). The metal atom and the catalytic aspartates are shown at the bottom of the pictures on the right. Ligands are depicted as stick figures. Only nearby amino acids (up to 350 pm away from these compounds) are represented as wireframes on the right. Atom colors: oxygen (red), carbon (gray), polar hydrogen (white), nitrogen (blue), fluorine (orange) and chlorine (green). The illustrated representation of the protein depicts helices (red) and loops (gray).

FIGS. 12-16 show certain preferred bifunctional compounds according to the present invention. These include 4H-new5b1, 4H-new5b2; 4H-new5f1; 4H-new5f2; 4H-new5H1; 5H-new1 and 5H-new2 and 5H-new3 as depicted in the figures.

FIGS. 20-21 show the biological activity of compound labeled Z641-0002 against A549 lung cancer cells in colony formation assays. Lung cancer cells were chosen for these assays because they are often resistant to most chemotherapeutic agents, and novel compounds to treat lung cancer patients are needed. Although cisplatin is one of the most active current drugs for treating lung cancer, this lung cancer cell line is resistant to cisplatin. The assays were performed with this compound constantly present over the time course of the assay. Fractional colony formation with the compound present was compared to colony formation in the presence of vehicle and shown as a percentage of the control. A dose dependent effect against colony survival was evidenced by Z641-0002 in combination with cisplatin. Note that cisplatin is present for a shorter period of time which was chosen to mimic the physiologic serum presence of the drug in patients.

FIGS. 22-23 show the biological activity of compound labeled Z641-0011 against A549 lung cancer cells in colony formation assays. The assays were performed with this compound constantly present over the time course of the assay. Fractional colonal formation with the compound present was compared to colony formation in the presence of vehicle and shown as a percentage of the control. A significant dose dependent effect against colony survival was evidenced by Z641-0011 alone, or in combination with cisplatin. Note that cisplatin is present for a shorter period of time which was chosen to mimic the physiologic serum presence of the drug in patients.

FIGS. 24-27 show the biological activity of compound labeled Z641-0013 against A549 lung cancer cells in colony formation assays. The assays were performed with this compound constantly present over the time course of the assay. Fractional colony formation with the compound present was compared to colony formation in the presence of vehicle and shown as a percentage of the control after overnight assays and in chronic exposure (for the time course of the assay). When this compound is present, it has more colony forming cell cytotoxicity than a higher concentration of cisplatin; however, cisplatin is present for a shorter period. This cisplatin time period was chosen to mimic the physiologic serum presence of the drug in patients. A significant dose dependent effect against colony survival was evidenced by Z641-0013 alone, or in combination with cisplatin, although administration of the compound for a longer period (chronic) resulted in a greater anticancer (cytotoxic) effect.

FIGS. 28-29 show the biological activity of compound labeled Z641-0016 against A549 lung cancer cells in colony formation assays. The assays were performed with this compound constantly present over the time course of the assay. Fractional colony formation with the compound present was compared to colony formation in the presence of vehicle and shown as a percentage of the control. A significant dose dependent effect against colony survival was evidenced by Z641-0016 alone (although at higher concentrations), or in combination with cisplatin.

FIGS. 30-31 show the biological activity of compound labeled Z641-0017 against A549 lung cancer cells in colony formation assays. The assays were performed with this compound constantly present over the time course of the assay. Fractional colony formation with the compound present was compared to colony formation in the presence of vehicle and shown as a percentage of the control. A significant dose dependent effect against colony survival was evidenced by Z641-0017 alone (at higher concentrations), or in combination with cisplatin (again, at higher concentrations).

FIGS. 32-33 show the biological activity of compound labeled Z641-0032 against A549 lung cancer cells in colony formation assays. The assays were performed with this compound constantly present over the time course of the assay. Fractional colony formation with the compound present was compared to colony formation in the presence of vehicle and shown as a percentage of the control. A significant dose dependent effect against colony survival was evidenced by Z641-0032 alone or in combination with cisplatin.

FIGS. 34-35 show the biological activity of compound labeled Z641-0033 against A549 lung cancer cells in colony formation assays. The assays were performed with this compound constantly present over the time course of the assay. Fractional colony formation with the compound present was compared to colony formation in the presence of vehicle and shown as a percentage of the control. A significant dose dependent effect against colony survival was evidenced by Z641-0033 alone or in combination with cisplatin, although at higher concentrations.

FIGS. 36-37 show the biological activity of compound labeled Z641-0035 against A549 lung cancer cells in colony formation assays. The assays were performed with this compound constantly present over the time course of the assay. Fractional colony formation with the compound present was compared to colony formation in the presence of vehicle and shown as a percentage of the control. A significant dose dependent effect against colony survival was evidenced generally by Z641-0035 alone or in combination with cisplatin (at higher concentrations).

FIGS. 38-39 show the biological activity of compound labeled Z641-0036 against A549 lung cancer cells in colony formation assays. The assays were performed with this compound constantly present over the time course of the assay. Fractional colony formation with the compound present was compared to colony formation in the presence of vehicle and shown as a percentage of the control. A significant dose dependent effect against colony survival was evidenced by Z641-0017 alone (dose dependent) or in combination with cisplatin (also dose dependent).

FIGS. 40-41 show the biological activity of compound labeled WW-10 against A549 lung cancer cells in colony formation assays. Colony formation assays were performed with this compound for 24 hours at the beginning of the assay and then removed. Fractional colony formation with the compound present was compared to colony formation in the presence of vehicle and shown as a percentage of the control. A significant dose dependent effect against colony survival was evidenced by WW-10 alone at higher dose or in combination with cisplatin (also at higher dose). This bifunctional compound exhibited greater colony forming cell cytotoxicity than did cisplatin present at a higher concentration; however, the cisplatin was present for a shorter period of time.

FIG. 42 shows the biological activity of compound WW-01. Compound WW-01 is a novel derivative of the cancer drug bandamustine, where a Metnase inhibitor is ligated to it. The assays were performed with this compound constantly present over the time course of the assay. Fractional colony formation with the compound present was compared to colony formation in the presence of vehicle and shown as a percentage of the control. WW-01 exhibited significantly greater activity than cisplatin, although cisplatin was present for a shorter period of time.

SUMMARY OF THE INVENTION

Figure 2:
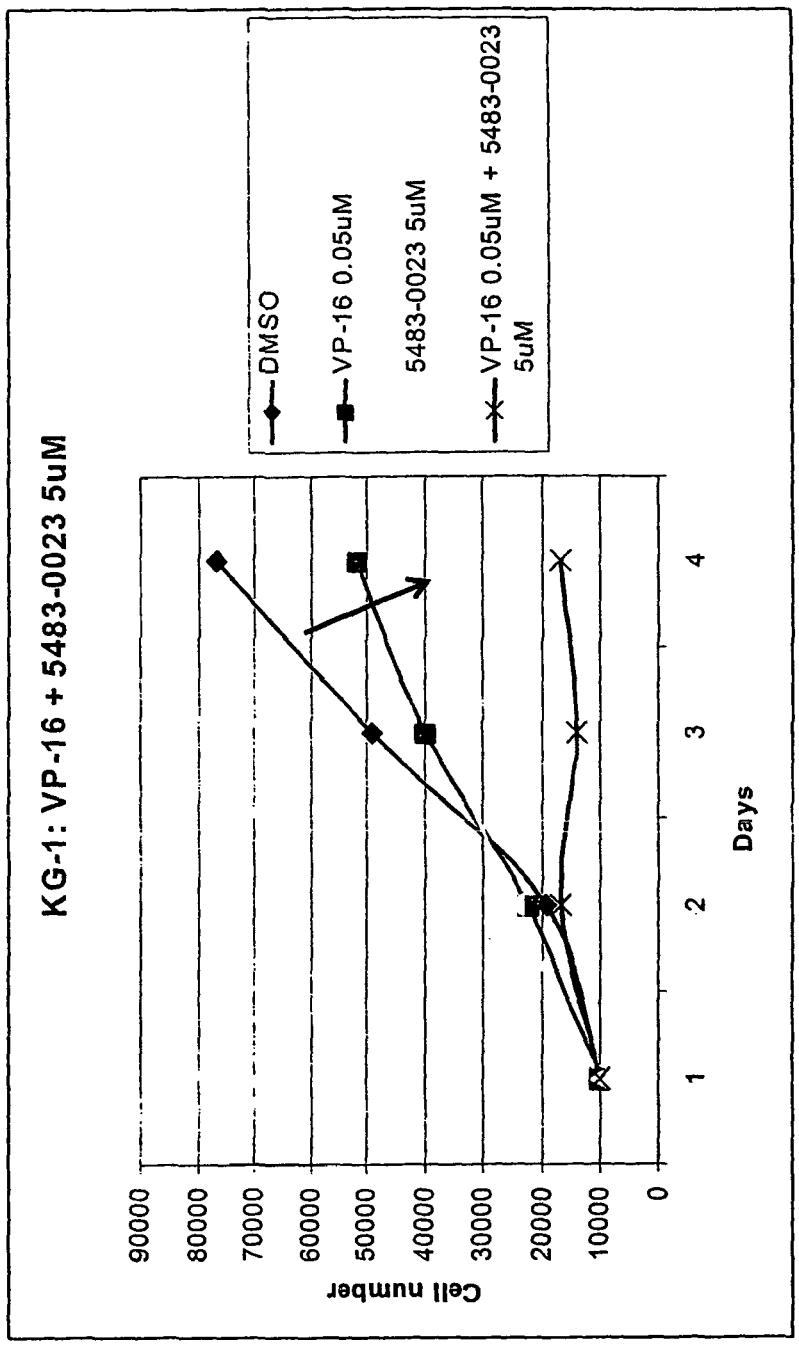
FIG. 2. As previously shown, the compound 5483-0023 not only increases the cytotoxic activity of the anti-cancer drug VP-16 in KG-1 leukemia cells, but also has cytotoxic activity on its own.

The present invention relates to compounds that are useful in the treatment of cancer, related pharmaceutical compositions, and methods of treating cancer. In preferred embodiment of the present invention, these compounds comprise a bifunctional agent one portion of which compounds comprise a Metnase and/or Intnase inhibitor and the other portion comprising an alkylating agent, preferably a nitrogen mustard moiety (e.g., bis(2-chloroethyl)amine).

In one aspect, the present invention relates to bifunctional inhibitors of Metnase and/or Intnase which have the chemical structure (or its corresponding carboxylate anion):

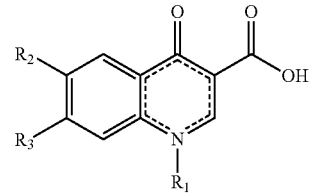

wherein:

$R_1$ is a $C_1$-$C_6$ hydrocarbon, preferably a linear, branched or cyclic alkyl group, preferably including a cyclopropane group or isopropyl group which is optionally substituted, a $(CH_2)_j$—$C_1$-$C_6$ ether or thioether group which is optionally substituted, a $(CH_2)_j$—$C_1$-$C_6$ acyl group which is optionally substituted, a $(CH_2)_j$—$NR^1R^2$ group wherein $R^1$ and $R^2$ are each independently H, or a $C_1$-$C_6$ alkyl group optionally substituted with halo or at least one hydroxyl group, an optionally substituted $(CH_2)_n$-amide group, an optionally substituted $(CH_2)_n$-thioamide group, an optionally substituted $(CH_2)_n$-aryl group or an optionally substituted $(CH_2)_n$-heterocyclic group, preferably a 5-12-membered non-aromatic heterocyclic group, preferably a 5- or 6-membered heterocyclic group (preferably a piperazinyl group);

Each j is independently 0, 1, 2, 3, 4, 5 or 6, preferably 1, 2 or 3;

Each n is independently 0, 1, 2, 3, 4, 5, or 6, preferably 0, 1, 2, or 3

$R_2$ is H, halo (preferably F, Cl, Br, I), or an optionally substituted $C_1$-$C_6$ hydrocarbon, preferably an optionally substituted linear, branched or cyclic alkyl group or an aryl group, preferably a carbocyclic aromatic group, such as a phenyl or naphthyl group which is optionally substituted (the phenyl group on the ortho, meta or para position, preferably meta or para position), preferably wherein the aryl, preferably carbocyclic aromatic group is substituted with a —$C_0$-$C_6$-hydrocarbon-$NR^cR^d$ group wherein said hydrocarbon (preferably an aliphatic hydrocarbon) is optionally substituted and is more preferably a —$(CH_2)_i$—$NR^cR^d$ group, where $R^c$ and $R^d$ are each independently a —$(CH_2)_i$—W group where each i is independently 0, 1, 2, 3, 4, 5 or 6, preferably 1, 2 or 3, more preferably 2, and W is a halo group, preferably a Cl or Br group, more preferably a Cl group;

$R_3$ is H, halo, —$N(H)R^a$, —$N(H)C(=O)R^a$, —$C(=O)R^b$, a

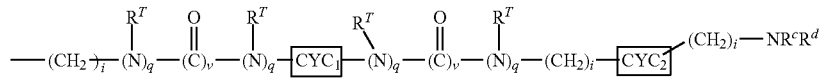

group or a —$C_0$-$C_6$-hydrocarbon-$NR^cR^d$ group which is optionally substituted, preferably an aliphatic hydrocarbon group, which is optionally substituted, preferably a —$(CH_2)_i$—$NR^cR^d$ group as set forth above and wherein $R_2$ and $R_3$ are not both H or halo; each of i, $R^c$ and $R^d$ is independently the same as described above;

each $R^T$ is independently H or a $C_1$-$C_3$ alkyl group which is optionally substituted with one or two hydroxyl groups;
each v is independently 0 or 1;
each q is independently 0 or 1;
CYC₁ is a first cyclic hydrocarbon group including a carbocyclic group, a heterocyclic group, an aryl or heteroaryl, preferably a heterocyclic group or aryl all of which groups may be optionally substituted, preferably a piperazine group or an optionally substituted phenyl group;
CYC₂ is a second cyclic hydrocarbon group including a carbocyclic group, heterocyclic group, aryl or heteroaryl, preferably a heteroaryl or aryl group, preferably an aromatic group, preferably a phenyl, indole or piperazine group, all of which groups may be optionally substituted;
$R^a$ is

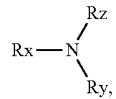

where $R_x$ is a $C_1$-$C_6$ hydrocarbon, preferably a linear branched or cyclic alkyl group which is optionally substituted, a $(CH_2)_j$—$C_1$-$C_6$ ether or thioether group which is optionally substituted, a $(CH_2)_j$—$C_1$-$C_6$ acyl group which is optionally substituted, an optionally substituted $(CH_2)_n$-amide group, or an optionally substituted $(CH_2)_n$-thioamide group, $R_y$, and $R_z$ are each independently, a $C_1$-$C_6$ hydrocarbon, preferably a linear branched or cyclic alkyl group which is optionally substituted, a $(CH_2)_j$—$C_1$-$C_6$ ether or thioether group which is optionally substituted, a $(CH_2)_j$—$C_1$-$C_6$ acyl group which is optionally substituted, a $(CH_2)_j$—$NR^1R^2$ group wherein $R^1$ and $R^2$ are each independently H, or a $C_1$-$C_6$ alkyl group optionally substituted with halo or at least one hydroxyl group, an optionally substituted $(CH_2)_n$-amide group, or an optionally substituted $(CH_2)_n$-thioamide group; $R^b$ is aryl (preferably optionally substituted carbocyclic aryl such as phenyl), a ($C_0$-$C_6$ hydrocarbon)-aryl, preferably a —$C_1$-$C_6$ alkyl-aryl, —O-aryl, a ($C_0$-$C_6$ hydrocarbon)-hetaryl, preferably a —$C_0$-$C_6$ alkyl-hetaryl, —O-hetaryl, wherein hetaryl is preferably a 5- or 6-membered heteroaromatic ring containing from 1 to 4 heteroatoms independently selected from N, O and S, and said 5 or 6-membered heteroaromatic ring is optionally fused with a benzene ring, and each $R^b$ group is further substituted with one or more substituents, each of which is independently $R^a$ as defined above, halo, $C_1$-$C_6$ hydrocarbon (preferably —$C_1$-$C_6$ alkyl), —$C_1$-$C_6$ haloalkyl, —O—$C_1$-$C_6$ alkyl, —O—$C_1$-$C_6$ haloalkyl, oxo (=O), or —$CO_2R_m$, where $R_m$ is —H or —$C_1$-$C_6$ alkyl which is optionally substituted with at least one hydroxyl group, or $R^b$ may be an optionally substituted $C_0$-$C_6$alkyl-W—X—Z group where W is an optionally substituted carbocyclic aryl or heteroaryl group, X is absent, S, O or a —$N(R^N)$—group where $R^N$ is H or a $C_1$-$C_3$ alkyl group which is optionally substituted with one or two hydroxyl groups and Z is absent, a carbocyclic aryl or heteroaryl group which is further optionally substituted with one or more substituents, each of which is independently $R^{a'}$, halo, $C_1$-$C_6$ hydrocarbon (preferably —$C_1$-$C_6$ alkyl), —$C_1$-$C_6$ haloalkyl, —O—$C_1$-$C_6$ alkyl, —O—$C_1$-$C_6$ haloalkyl, oxo (=O), or —$CO_2R_m$, wherein $R^{a'}$ is

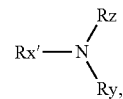

where Rx' is absent or $R_x$, and Ry and Rz are the same as described above, or
a pharmaceutically acceptable salt, solvate or polymorph thereof.

In preferred aspects of the invention, compounds according to the present invention as described above are represented by the following chemical structure:

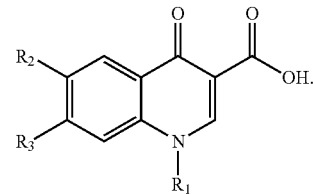

In certain preferred aspects, $R_1$ is H or a $C_1$-$C_6$ aliphatic (alkyl, alkenyl, or alkynyl) group, preferably alkyl, further preferably cyclopropyl or isopropyl, which is optionally substituted with at least one hydroxyl or halo group;
$R_2$ is H, halo or an optionally substituted (e.g. with an $C_1$-$C_6$ alkylene group between the phenyl group and the quinoline moiety) phenyl group which is substituted in the meta or para position with a —$(CH_2)_i$—$NR^cR^d$ group, where $R^c$ and $R^d$ are each independently a —$(CH_2)_i$—W group where each i is independently 1, 2 or 3, (preferably 2) and W is a Cl or Br group, more preferably a Cl group; and
$R_3$ is H, halo, —$N(H)R^a$, —$N(H)C(=O)R^a$, or —$C(=O)R^b$, a

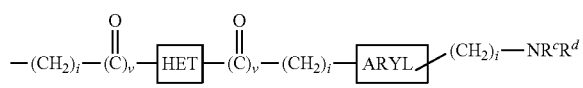

group, a

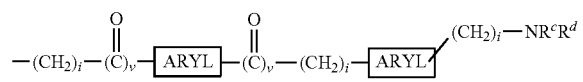

group or a

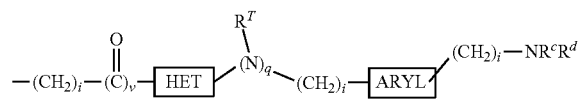

group
Where HET is a non-aromatic or aromatic heterocyclic group which is optionally substituted, preferably a non-aromatic heterocyclic group, further preferably a piperazine group;

ARYL is a carbocyclic aryl or heteroaryl group, preferably a carbocyclic aryl group, more preferably a phenyl group or an indole group;

Each i is independently 0, 1, 2, 3, 4, 5 or 6;
q is 0 or 1;
Each v is independently 0 or 1;
and $R^c$ and $R^d$ are each independently a $C_1$-$C_6$ aliphatic group, preferably an alkyl group which is substituted with at least one halo group, and
where $R^b$ is aryl (preferably aromatic aryl, preferably, phenyl) which is substituted (preferably in the meta- or para-position of the phenyl group) by $R^a$ as defined above where $R_x$ is a —(CH$_2$)$_i$— group, and each of $R_y$ and $R_z$ is a —CH$_2$CH$_2$Cl group. In preferred aspects of the invention, $R^c$ and $R^d$ are each preferably a —CH$_2$CH$_2$Cl group.

In other preferred aspects, compounds according to the present invention contain at least one mustard group, preferably one mustard group —(CH$_2$)$_i$—NR$^c$R$^d$ group on R$_2$ or R$_3$, where R$^c$ and R$^d$ are each independently a —(CH$_2$)$_i$—W group where each i is independently 1, 2 or 3, (preferably 2) and W is a Cl or Br group, more preferably a Cl group.

In certain further preferred embodiments, R$_1$ is a cyclopropyl or isopropyl group, R$_2$ is H opr halo when R$_3$ is a phenyl group substituted in the meta or para position with a —(CH$_2$)$_i$—W group where i is 1, 2 or 3, (preferably 2) and W is a Cl or Br group, more preferably a Cl group.

Exemplary and preferred structures and/or compounds of the present invention are presented in the present application, including FIGS. 1-41, especially FIGS. 12-19 which depict chemical structures of preferred embodiments of the present compounds hereof. Each of these modifications defined above can be attached to the nitrogen mustard group to produce a bifunctional cancer drug that would both stall replication forks by cross-linking DNA and inhibit the ability of Metnase and/or Intnase, preferably both, to repair those stalled forks. Other compounds as disclosed have anti-cancer activity as well, either alone or in combination with another anticancer agent (synergistic activity) or in combination with radiation therapy as otherwise described herein.

Another aspect of the invention relates to pharmaceutical compositions comprising an effective amount of at least one bifunctional inhibitor of Metnase and/or Intnase as described above, optionally in combination with a pharmaceutically acceptable carrier, additive or excipient, further optionally in combination with an effective amount of an additional bioactive agent, including an anticancer agent, as otherwise described herein.

Another aspect of the invention relates to a method of inhibiting both Metnase and Intnase wherein both Metnase and Intnase, and in particular Metnase and Intnase in a patient, are exposed to an effective amount of a bifunctional inhibitor of Metnase and Intnase as described above. Inhibition of Metnase and Intnase in a patient, especially a cancer patient, comprising administering an effective amount of a bifunctional inhibitor of Metnase and Intnase to that patient, represents another aspect of the present invention.

A further aspect of the invention relates to the use of a bifunctional inhibitor of Metnase and/or Intnase, either alone or preferably in combination with an anticancer agent or other anticancer therapy such as radiation therapy, to treat a cancer patient. In this method, a bifunctional inhibitor of Metnase and/or Intnase as otherwise described herein is administered to a cancer patient, alone or in combination with at least one traditional anticancer agent to treat cancer. In many aspects of the invention, the combination of a bifunctional inhibitor of Metnase and/or Intnase and at least one anticancer agent or other anticancer therapy provides a synergistically favorable treatment of the cancer.

Still a further aspect of the invention relates to the use of a bifunctional inhibitor of Metnase and/or Intnase, especially including specific bifunctional inhibitors of Metnase and/or Intnase described herein for enhancing or potentiating the biological effects of an anticancer agent or anticancer therapy (radiation therapy). There administration of the bifunctional inhibitor may occur prior to, concomitant with and/or subsequent, preferably immediately subsequent to radiation treatment in order to enhance the effects of the radiation therapy and treatment of cancer.

In preferred embodiments, compounds, compositions and methods of treatment of the invention are used to treat a patient suffering from leukemia (e.g. acute myeloid leukemia (AML)), as well as numerous other cancers, including prostate cancer, and as otherwise disclosed in greater detail herein. In certain aspects of such treatments, compounds, compositions and methods of treatment of the invention are administered as a monotherapy (in some cases, to patients who have exhibited drug resistance to numerous anticancer agents including for example, Topo IIalpha inhibitors such as VP-16), or are co-administered with a Topo IIalpha inhibitor, as well as a large number of other traditional anticancer agents.

DETAILED DESCRIPTION OF THE INVENTION

The following terms, among others, are used to describe the present invention. It is to be understood that a term which is not specifically defined is to be given a meaning consistent with the use of that term within the context of the present invention as understood by those of ordinary skill.

The term "compound", as used herein, unless otherwise indicated, refers to any specific chemical compound disclosed herein and includes tautomers, regioisomers, geometric isomers, and where applicable, optical isomers (e.g. enantiomers) thereof, as well as pharmaceutically acceptable salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds as well as diastereomers and epimers, where applicable in context. The term also refers, in context to prodrug forms of compounds which have been modified to facilitate the administration and delivery of compounds to a site of activity.

The term "patient" or "subject" is used throughout the specification within context to describe an animal, generally a mammal and preferably a human, to whom treatment, including prophylactic treatment (prophylaxis), with the compositions according to the present invention is provided. For treatment of those infections, conditions or disease states which are specific for a specific animal such as a human patient, the term patient refers to that specific animal. Bifunctional inhibitors of Metnase and/or Intnase according to the present invention may be used to treat cancer per se, or to enhance the effects of other chemotherapeutic agents (anticancer) in treating cancer in patients. However, in certain important aspects of the present invention, bifunctional inhibitors of Metnase and/or Intnase or antagonists also find use to potentiate the therapeutic effects of radiation therapy.

It is noted that while bifunctional inhibitors of Metnase and/or Intnase according to the present invention may be used to treat cancer in all patients (including HIV infected patients), in certain embodiments, and in particular, with respect to the use of the integrase inhibitors including, for example, N-(2-(4-(4-fluorobenzylcarbamoyl)-5-hydroxy-1-methyl-6-oxo-1,6-dihydropyrimidine-2-yl)propan-2-yl)-5-methyl-1,3,4-oxadiazole-2-carboxamide (Raltegravir) and (S)-6-(3-chloro-2-fluorobenzyl)-1-(1-hydroxy-3-methylbutan-2-yl)-7-methoxy-4-oxo-1,4-dihydroquinoline-3-carboxylic acid (Elvitegravir), the use of the present compounds to inhibit Metnase and/or Intnase and to treat cancer (or potentiate other anticancer agents and/or radiation therapy) in patients including human immunodeficiency virus HIV positive patients (further including patients with acquired immunodeficiency deficiency syndrome (AIDS) and aids-related complex (ARC) is a further aspect of the invention. Thus, the present invention may also be used to inhibit Metnase and/or Intnase, and to treat cancer in patients, including HIV patients, to whom standard monofunctional integrase (which compounds may also inhibit Metanse and/or Intnase) inhibitors, are also administered.

In HIV patients, the bifunctional compounds according to the present invention also may be used to treat cancers including those cancers which are typically found secondary to HIV infections in HIV patients, in particular, Kaposi's sarcoma, among other cancers, including non-Hodgkin's lymphoma, and invasive cervical cancer. However, other types of cancer also appear to be more common among those infected with HIV, all of which are also treated by the present invention. While not classified as AIDS-defining, these malignancies are found to be affecting the HIV/AIDS community greatly and have been referred to as "AIDS-associated malignancies" or "opportunistic" cancers, including Hodgkin's disease, anal cancer, lung cancer and testicular germ cell cancer, among others. All of these cancers may be treated by the bifunctional inhibitors according to the present invention, alone or in combination with other anti-cancer agents or with other monofunctional Metnase and/or Intnase inhibitors.

The term "HIV infection" is used to describe an infection in a person with human immunodeficiency virus 1 and/or 2 who is a candidate or potential candidate for treatment with an integrase inhibitor.

The term "human immunodeficiency virus" or "HIV" shall be used to describe human immunodeficiency viruses 1 and 2 (HIV-1 and HIV-2).

The terms "ARC" and "AIDS" refer to syndromes of the immune system caused by the human immunodeficiency virus, which are characterized by susceptibility to certain diseases and T cell counts which are depressed compared to normal counts. HIV progresses from Category 1 (Asymptomatic HIV Disease) to Category 2 (ARC), to Category 3 (AIDS), with the severity of the disease.

The term "effective" is used herein, unless otherwise indicated, to describe an amount of a compound or composition which, in context, is used to produce or effect an intended result, whether that result relates to the inhibition of the effects of Metnase and/or Intnase, to potentiate an anticancer agent or radiation therapy in cancer or as otherwise described herein. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for or afflicted by cancer, including the inhibition of cancer cell or tumor growth, promotion of apoptosis and/or death of cancer cells and/or tumorous tissue resulting in the shrinkage or reduction in cancer cells, including tumors, improvement in the cancer through lessening or suppression of at least one symptom, delay in progression of cancer or the reduction in likelihood or the prevention of metastasis of cancer or the potentiation/enhancement of anticancer agents and/or other cancer therapies including radiation therapy. Treatment, as used herein, encompasses both prophylactic (including, as described, "reducing the likelihood" of a disease state and/or condition) and therapeutic treatment.

The term "Intnase", "Gypsy Retransposon Integrase 1", "GIN-1", or "Gypsy Integrase-1" is used to describe a human protein with an Integrase domain that is related to HIV Integrase and the retroviral Integrases such as Rous sarcoma virus (FIGS. 1 and 2). Such Integrase domains are known to have endonuclease activity, and it is demonstrated here that Intnase also has such activity, consistent with its membership in the family of proteins. The Intnase protein has endonuclease activity that nicks and linearizes double stranded plasmid DNA. It also has single stranded DNA endonuclease activity, wherein it can specifically cleave off 4 nucleotides from the 3' end of a single strand of DNA. Repressing Intnase expression makes cells more sensitive to the cancer chemotherapeutic agent hydroxyurea and over-expressing it reduces sensitivity to hydroxyurea and radiation, both of which are widely used in cancer treatment. This demonstrates that this protein is an important target for inhibition to increase the effectiveness of cancer chemotherapy and radiation. Compounds that bind, or dock, to the active site of the Intnase protein have been identified by computer screening, and these compounds have been demonstrated to increase the sensitivity of several cancer chemotherapeutic agents. In this way, compounds according to the present invention function to enhance anticancer therapy, including anticancer agents and radiation therapy.

The term "Intnase inhibitor" is used to refer to a compound which inhibits the protein Intnase (also Gypsy Integrase-1, GIN-1, or Gypsy Retrotransposon 1) preferably in a patient or subject. An Intnase inhibitor for use in the present invention includes, for example, compounds which are specifically set forth herein, including the attached figures, as well as compounds which are disclosed in U.S. Pat. Nos. 7,169,780; 7,176,220; 7,435,734, WO2006/060712; 7,538,112; 7,538,112; 7,138,408; 7,517,532; 7,399,763; 7,479,497; 7,148,237; 7,358,249; 7,157,447; 7,368,571; 7,135,467; 7,468,375; 7,135,482; 7,135,482; 7,459,459; 7,115,601; 7,109,201; 7,109,186; 7,037,908; 7,001,912; 7,015,212 and PCT/

US2010/029462 (published as WO2010/114919), each of which patents/applications is incorporated by reference in its entirety herein.

"Metnase" (also termed SETMAR) is a human SET and transposase domain protein that methylates histone H3 and promotes DNA double-strand break repair. After DNA replication, sister chromatids must be untangled, or decatenated, before mitosis so that chromatids do not tear during anaphase. Topoisomerase IIalpha (Topo IIalpha) is the major decatenating enzyme. Topo IIalpha inhibitors prevent decatenation, causing cells to arrest during mitosis. Acute myeloid leukemia cells fail to arrest at the mitotic decatenation checkpoint, and their progression through this checkpoint is regulated by the DNA repair component Metnase. Metnase contains a SET histone methylase and transposase nuclease domain, and is a component of the nonhomologous end-joining DNA double-strand break repair pathway. Metnase interacts with Topo IIalpha and enhances its decatenation activity. Multiple types of acute leukemia cells have an attenuated mitotic arrest when decatenation is inhibited and that in an acute myeloid leukemia (AML) cell line this is mediated by Metnase. Of further importance, Metnase permits continued proliferation of these AML cells even in the presence of the clinical Topo IIalpha inhibitor VP-16. In vitro, purified Metnase prevents VP-16 inhibition of Topo IIalpha decatenation of tangled DNA. Thus, Metnase expression levels may predict AML resistance to Topo IIalpha inhibitors, and Metnase is a potential therapeutic target for small molecule interference.

Thus, Metnase physically interacts and co-localizes with Topoisomerase IIα (Topo IIα), the key chromosome decatenating enzyme. Metnase promotes progression through decatenation and increases resistance to the Topo IIα inhibitors ICRF-193 and VP-16. Purified Metnase greatly enhanced Topo IIα decatenation of kinetoplast DNA to relaxed circular forms. Nuclear extracts containing Metnase decatenated kDNA more rapidly than those without Metnase, and neutralizing anti-sera against Metnase reversed that enhancement of decatenation. Metnase automethylates at K485, and the presence of a methyl donor blocked the enhancement of Topo IIα decatenation by Metnase, implying an internal regulatory inhibition. Metnase therefore enhances Topo IIα decatenation, and this activity is repressed by automethylation, suggesting that cancer cells could subvert Metnase to mediate clinically relevant resistance to Topo IIα inhibitors.

The term "cancer" is used throughout the present invention to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Representative cancers include, for example, prostate cancer, metastatic prostate cancer, stomach, colon, rectal, liver, pancreatic, lung, breast, cervix uteri, corpus uteri, ovary, testis, bladder, renal, brain/CNS, head and neck, throat, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, esophagus, larynx, nasopharyngeal, kidney cancer and lymphoma, among others, which may be treated by one or more compounds according to the present invention. Because of the activity of the present compounds as Metnase and/or Intnase inhibitors, the present invention has general applicability treating virtually any cancer in any tissue, thus the compounds, compositions and methods of the present invention are generally applicable to the treatment of cancer.

Although all cancers may be treated with bifunctional inhibitors of Metnase and/or Intnase, either alone or in combination with one or more anticancer agents or in combination with radiation therapy, in certain particular aspects of the present invention, the cancer which is treated is pancreatic cancer, lung cancer, breast cancer, leukemia or prostate cancer, including metastatic prostate cancer, especially where radiation therapy is used to treat the prostate cancer. Thus, the present invention is generally applicable and may be used to treat any cancer in any tissue, regardless of etiology.

The term "pharmaceutically acceptable salt" or "salt" is used throughout the specification to describe a salt form of one or more of the compositions herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, including the treatment of prostate cancer, including metastatic prostate cancer, the term "salt" shall mean a pharmaceutically acceptable salt, consistent with the use of the compounds as pharmaceutical agents.

The term "co-administration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, including sequential administration. Preferably, effective concentrations of all co-administered compounds or compositions are found in the subject at a given time. Bifunctional inhibitors of Metnase and Intnase according to the present invention may be administered with one or more additional anti-cancer agents or other agents which are used to treat or ameliorate the symptoms of cancer, especially prostate cancer, including metastatic prostate cancer. Exemplary anticancer agents which may be co-administered in combination with one or more chimeric compounds according to the present invention include, for example, antimetabolites, inhibitors of topoisomerase I and II, alkylating agents and microtubule inhibitors (e.g., taxol). Specific anticancer compounds for use in the present invention include, for example, adriamyucin aldesleukin; alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral;

calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemcitabine, gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); uracil mustard; valrubicin; valtorcitabine (monoval LDC); vinblastine; vinorelbine; zoledronate; and mixtures thereof, among others.

The term "radiation therapy" is used to describe therapy for cancer, especially including prostate cancer, which may be used in conjunction with the present compounds which exhibit activity as Intnase inhibitors having inherent anticancer activity. Radiation therapy uses high doses of radiation, such as X-rays, to destroy cancer cells. The radiation damages the genetic material of the cells so that they can't grow. Although radiation damages normal cells as well as cancer cells, the normal cells can repair themselves and function, while the cancer cells cannot.

Radiation therapy may be used in combination with the presently claimed compounds, which inhibit Intnase and consequently, the cancer cells' ability to repair damage done by the radiation, thus potentiating radiation therapy. Radiation therapy is most effective in treating cancers that have not spread (metastasized). But it also may be used if the cancer has spread to nearby tissue. Radiation is sometimes used after surgery to destroy any remaining cancer cells and to relieve pain from metastatic cancer.

Radiation is delivered in one of two ways: External-beam radiation therapy and branchytherapy. External-beam radiation therapy uses a large machine to aim a beam of radiation at the tumor. After the area of cancer is identified, an ink tattoo no bigger than a pencil tip is placed on the skin of the subject so that the radiation beam can be aimed at the same spot for each treatment. This helps focus the beam on the cancer to protect nearby healthy tissue from the radiation. External radiation treatments usually are done 5 days a week for 4 to 8 weeks or more. If cancer has spread, shorter periods of treatment may be given to specific areas to relieve pain.

There are basically three types of external radiation therapy: conformal radiotherapy (3D-CRT), intensity-modulation radiation therapy (IMRT) and proton therapy. Conformal radiotherapy uses a three-dimensional planning system to target a strong dose of radiation to the cancer. This helps to protect healthy tissue from radiation. Intensity-modulated radiation therapy uses a carefully adjusted amount of radiation. This protects healthy tissues more than conformal radiotherapy does. Proton therapy uses a different type of energy (protons) than X-rays. This approach allows a higher amount of specifically directed radiation, which protects nearby healthy tissues the most. Sometimes proton therapy is combined with X-ray therapy.

Brachytherapy, or internal radiation therapy, uses dozens of tiny seeds that contain radioactive material. It may be used preferably to treat early-stage prostate and other cancer which is localized. Needles are used to insert the seeds through the skin into tissue, most often the prostate. The surgeon uses ultrasound to locate the tissue and guide the needles. As the needles are pulled out, the seeds are left in place. The seeds release radiation for weeks or months, after which they are no longer radioactive. The radiation in the seeds can't be aimed as accurately as external beams, but they are less likely to damage normal tissue. After the seeds have lost their radioactivity, they become harmless and can stay in place.

Radiation therapy may combine brachytherapy with low-dose external radiation. In other cases, treatment combines surgery with external radiation. In the present invention, compounds which are otherwise claimed may be used as radiation sensitizers to enhance or potentiate the effect of radiation by inhibiting the ability of the cancer tissue to repair the damage done by the radiation therapy.

The terms "antagonist" and "inhibitor" are used interchangeably to refer to an agent, especially including chemical agents which are specifically disclosed herein that decreases or suppresses a biological activity, such as to repress an activity of Metnase and Intnase.

The term "acyl" is art-recognized and refers to a group represented by the general formula hydrocarbylC(O)—, preferably alkylC(O)—.

The term "acylamino" is art-recognized and refers to a moiety having an amino group and an acyl group and may include substitutents on same as otherwise disclosed herein.

The term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed herein, except where stability of the moiety is prohibitive. For example, substitution of alkenyl groups by one or more alkyl, carbocyclyl, aryl, heterocyclyl, or heteroaryl groups is contemplated according to the present invention.

The terms "alkoxyl" or "alkoxy" as used herein refers to an alkyl group, as defined below, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$-substituent, where m is 0 to 6 and the substituent is an aryl or substituted aryl group, a cycloalkyl group, a cycloalkenyl, a heterocycle or a polycycle (two or three ringed), each of which may be optionally substituted.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl (lower alkyl) has 10 or fewer carbon atoms in its backbone (e.g., $C_1$-$C_{10}$ for straight chains, $C_1$-$C_{10}$ for branched chains), and more preferably 8 or fewer, and most preferably 6 or fewer. Likewise, preferred cycloalkyls have from 3-10 carbon atoms in their ring structure, and more preferably have 3, 4, 5, 6, 7 or 8 carbons in the ring structure. Within context, the term alkyl, which is optionally substituted subsumes alkylene groups. It is noted within the present application that when a range of elements/atoms or components is given, the complete range which is presented is disclosed and intended as is each individual component falling within the range presented. Thus, according to the present invention and by way of non-limiting example, a $C_0$ to $C_6$ hydrocarbon refers to a hydrocarbon as otherwise described herein which contains zero carbons (and therefore is absent), one carbon, two carbons, three carbons, four carbons, five carbons and six carbons.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety or as otherwise described herein. It will be understood by those skilled in the art that the individual substituent chemical moieties can themselves be substituted. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary, non-limiting substituted alkyls are described herein. Cycloalkyls can be further substituted with alkyls, alkenyls, alkynyls, alkoxys, alkylthios, aminoalkyls, carbonyl-substituted alkyls, —$CF_3$, —CN, and the like.

Analogous substitutions can be made to alkenyl and alkynyl groups to produce, for example, without limitation, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

Unless the number of carbons is otherwise specified, "lower alkyl" as used herein means an alkyl group, as defined above, but having from one to ten, one to eight, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl without further defining the group, is a lower alkyl as otherwise described herein.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$-substituent, wherein m is 0 or an integer from 1 to 8 and substituent is the same as defined herein and as otherwise below (R9 and R10 for amine/amino). Representative alkylthio groups include methylthio, ethylthio, and the like.

The terms "amine" and "amino" are art-recognized and refer to both unsubstituted and substituted amines, e.g., a moiety that can be represented, without limitation, by the general formula:

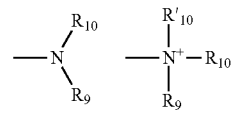

wherein $R_9$, $R_{18}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In certain such embodiments, neither $R_9$ and $R_{10}$ is attached to N by a carbonyl, e.g., the amine is not an amide or imide, and the amine is preferably basic, e.g., its conjugate acid has a $pK_a$ above 7. In even more preferred embodiments, $R_9$ and $R_{10}$ (and optionally, $R'_{10}$) each independently represent a hydrogen, an alkyl, an alkenyl, or —$(CH_2)_m$—R8. Thus, the term "alkylamine" as used herein means an amine group, as defined above, having a substituted or unsubstituted alkyl attached thereto, i.e., at least one of $R_9$ and $R_{10}$ is an alkyl group. Each of the groups which is bonded to the amine group, where applicable, may be optionally substituted.

The term "amido" is art-recognized as an amino-substituted carbonyl and includes a moiety that can be represented by the general formula:

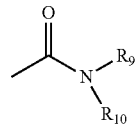

wherein $R_9$, $R_{10}$ are as defined above. Preferred embodiments of the amide will not include imides that may be unstable.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups containing from zero to four heteroatoms, for example, benzene (phenyl), pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "hetaryls", "aryl heterocycles", "heteroaromatics", "heteroaryl groups". The aromatic ring can be substituted at one or more ring positions with such substituents as otherwise described herein, for example, halogen, azide, alkyl, aralkyl, alkenyl, alkynyl, cycloalkyl, polycyclyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons or heteroatoms (heteroaryl) are common to two adjoining rings (the rings are "fused rings") wherein at least one, two or all of the rings is aromatic, or where one of the rings is aromatic and the other cyclic rings can be non-aromatic saturated or unsaturated rings including cycloalkyls, cycloalkenyls, cycloalkynyls, aryls and/or heterocyclyls.

The term "carbocycle" or "carbocyclic", as used herein, refers to an aromatic or non-aromatic ring in which each atom of the ring is carbon.

The term "carbonyl" is art-recognized and includes such moieties as can be represented by the general formula:

wherein X is a bond or represents an oxygen or a sulfur, and $R_{11}$ represents, for example without limitation, a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as otherwise described herein without limitation. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R'_{11}$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "electron withdrawing group" refers to chemical groups which withdraw electron density from the atom or group of atoms to which electron withdrawing group is attached. The withdrawal of electron density includes withdrawal both by inductive and by delocalization/resonance effects. Examples of electron withdrawing groups attached to aromatic rings include perhaloalkyl groups, such as trifluoromethyl, halogens, azides, carbonyl containing groups such as acyl groups, cyano groups, and imine containing groups.

The term "ester", as used herein, refers to a group —C(O)O-substituent wherein the substituent represents, for example, a hydrocarbyl or other substitutent as is otherwise described herein.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heterocyclyl" or "heterocyclic group" refer to 3- to 20-membered ring structures, more preferably 5 to 14 membered rings, 3- to 7-membered rings or 5 to 12- or 5 to 10-membered rings, whose ring structures include one to four heteroatoms. Heterocycles can also be polycycles. Heterocyclyl groups include, for example, without limitation, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above without limitation, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like, and as otherwise described herein.

The terms "heteroaryl" and "hetaryl" include substituted or unsubstituted aromatic single ring structures, preferably 5 to 10-membered rings, 5- to 7-membered rings, or preferably 5- to 6-membered rings, whose ring structures include at least one heteroatom, preferably one to four heteroatoms, more preferably one or two heteroatoms. The terms "heteroaryl" and "hetaryl" may also include, within context, up to 20-membered polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted aromatic or preferably, non-aromatic ring structures (which can be cyclic, bicyclic or a fused ring system), preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "5- to 20-membered heterocyclic group" or "5- to 14-membered heterocyclic group" as used throughout the present specification refers to an aromatic or non-aromatic cyclic group having 5 to 20 atoms, preferably 5 to 14 atoms forming the cyclic ring(s) and including at least one hetero atom such as nitrogen, sulfur or oxygen among the atoms forming the cyclic ring, which is a "5 to 20-membered, preferably 5- to 14-membered aromatic heterocyclic group" (also, "heteroaryl" or "heteroaromatic") in the former case and a "5 to 20-membered", preferably a "5- to 14-membered non-aromatic heterocyclic group" in the latter case. Among the heterocyclic groups which may be mentioned include nitrogen-containing aromatic heterocycles such as pyrrole, pyridine, pyridone, pyridazine, pyrimidine, pyrazine, pyrazole, imidazole, triazole, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole. As examples of the "5- to 14-membered aromatic heterocyclic group" there may be mentioned preferably, pyridine, triazine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzthiazole, phenothiazine, pyrrolopyrimidine, furopyridine and thienopyrimidine, more preferably pyridine, thiophene, benzothiophene, thiazole, benzothiazole, quinoline, quinazoline, cinnoline, pyrrolopyrimidine, pyrimidine, furopyridine and thienopyrimidine. The term "heterocyclic group" shall generally refer to 3 to 20-membered heterocyclic groups, preferably 3 to 14-membered heterocyclic groups and all subsets of heterocyclic groups (including non-heteroaromatic or heteroaromatic) subsumed under the definition of heterocyclic group are 3 to 20-membered heterocyclic groups, preferably 3 to 14-membered heterocyclic groups.

The term "8 to 20-membered heterocyclic group", or "8 to 14-membered heterocyclic group" refers to an aromatic or non-aromatic fused bicyclic or tricyclic group having 8 to 20, preferably 8 to 14 atoms forming the cyclic rings (two or three rings) and include at least one hetero atom such as nitrogen, sulfur or oxygen among the atoms forming the cyclic rings, which is a "8 to 20-membered", preferably a "8- to 14-membered aromatic heterocyclic group" (also, "heteroaryl" or "heteroaromatic") in the former case and a "8 to 20-membered", preferably a "8- to 14-membered non-aromatic heterocyclic group" in the latter case. "8 to 20-membered heterocyclic groups" and "8 to 14 membered heterocyclic groups" are represented by fused bicyclic, tricyclic and tetracyclic ring structures containing nitrogen atoms such as indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, benzimidazole, pyrrolopyridine, pyrrolopyrimidine and pyridopyrimidine; sulfur-containing aromatic heterocycles such as thiophene and benzothiophene; oxygen-containing aromatic heterocycles such as cyclopentapyran, benzofuran and isobenzofuran; and aromatic heterocycles comprising 2 or more hetero atoms selected from among nitrogen, sulfur and oxygen, such as benzoxazole, benzothiazole, benzothiadiazole, phenothiazine, benzofurazan, phenoxazine, pyrazoloxazole, imidazothiazole, thienofuran, furopyrrole, pyridoxazine, furopyridine, furopyrimidine and thienopyrimidine, among others.

The term "5- to 14-membered non-aromatic heterocyclic group" as used throughout the present specification refers to a non-aromatic cyclic group having 5 to 14 atoms forming the cyclic ring and including at least one hetero atom such as nitrogen, sulfur or oxygen among the atoms forming the cyclic ring. As specific examples there may be mentioned non-aromatic heterocycles such as pyrrolidinyl, pyrrolinyl, piperidinyl, piperazinyl, N-methylpiperazinyl, imidazolinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3-dioxolane, 1,3-dioxane, 1,4-dioxane, phthalimide and succinimide. As examples of the "5- to 14-membered non-aromatic heterocyclic group" there may be mentioned preferably, pyrrolidinyl, piperidinyl and morpholinyl, and more preferably pyrrolidinyl, piperidinyl, morpholinyl and pyrrole.

The term "8- to 14-membered non-aromatic heterocyclic group" as used throughout the present specification refers to a non-aromatic fused cyclic ring system (generally with two or three rings) having 8 to 14 atoms forming the cyclic rings (bicyclic or tricyclic) and including at least one hetero atom such as nitrogen, sulfur or oxygen among the atoms forming the cyclic rings.

The term "5- to 14-membered heterocyclic group" as used throughout the present specification refers to an aromatic or non-aromatic cyclic group having 5 to 14 atoms forming the cyclic ring and including at least one hetero atom such as nitrogen, sulfur or oxygen among the atoms forming the cyclic ring, which is a "5- to 14-membered aromatic heterocyclic group" in the former case and a "5- to 14-membered non-aromatic heterocyclic group" in the latter ease. Specific examples of the "5- to 14-membered heterocyclic group" therefore include specific examples of the "5- to 14-membered aromatic heterocyclic group" and specific examples of the "5- to 14-membered non-aromatic heterocyclic group".

As the "5- to 14-membered heterocyclic group" there may be mentioned preferably pyrrolidinyl, piperidinyl, morpholinyl, pyrrole, pyridine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzothiazole, phenothiazine and carbostyryl, more preferably pyrrolidinyl, piperidinyl, morpholinyl, pyrrole, pyridine, thiophene, benzothiophene, thiazole, benzothiazole, quinoline, quinazoline, cinnoline and carbostyryl, and even more preferably thiazole, quinoline, quinazoline, cinnoline and carbostyryl, among others.

The term "6- to 14-membered aromatic heterocyclic group", "hetaryl" or "heteroaryl" as used throughout the present specification refers to those substituents defined by "5- to 14-membered aromatic heterocyclic group" which have 6 to 14 atoms forming the cyclic ring. As specific examples there may be mentioned pyridine, pyridone, pyrimidine, indole, quinoline, isoquinoline, quinolizine, phthalazine, naphthyridine, quinazoline, cinnoline, acridine, benzothiophene, benzofuran, thiazole, benzothiazole and phenothiazine*. "8 to 14-membered aromatic heterocyclic groups" refer to those substituents or radicals having 8 to 14 atoms forming fused two or three cyclic ring systems. Specific examples include indole, quinoline, isoquinoline, quinolizine, phthalazine, naphthyridine, quinazoline, cinnoline, acridine, benzothiophene, benzofuran, benzothiazole, pyrrolopyrimidine, pyrrolopyrazine, furopyrimidine and phenothiazine, among numerous others.

The term "6- to 14-membered heterocyclic group" as used throughout the present specification refers to those substituents defined by "5- to 14-membered heterocyclic group" which have 6 to 14 atoms forming the cyclic ring(s). As specific examples there may be mentioned piperidinyl, piperazinyl, N-methylpiperazinyl, morpholinyl, tetrahydropyranyl, 1,4-dioxane and phthalimide.

The term "3 to 7-membered heterocyclic group" as used throughout the present specification refers to those heterocyclic substituents which have 3 to 7 atoms forming the cyclic ring, preferably 5 to 6 atoms forming the cyclic ring.

The term "8 to 14-membered heterocyclic group" as used throughout the present specification refers to those substituents defined "8- to 14-membered heterocyclic groups which have 8 to 14 atoms forming the fused cyclic ring system.

The term "heterocyclylalkyl", as used herein, refers to an alkyl group substituted with a heterocycle group.

The term "hydrocarbon" or "hydrocarbyl", as used herein, refers to an optionally substituted group that is bonded through a carbon atom and typically has at least one carbon-hydrogen bond and a primarily carbon backbone, but may optionally include heteroatoms. Hydrocarbyl groups include, but are not limited to aryl, heteroaryl, carbocycle, heterocycle, alkyl, alkenyl, alkynyl, and combinations thereof.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "polycyclyl" or "polycyclic group" refer to two or more rings (e.g., cycloalkyls, cycloalkenyls, cycloalkynyls, aryls and/or heterocyclyls) in which two or more atoms are common to two adjoining rings, e.g., the rings are "fused rings". Rings that are joined through non-adjacent atoms are termed "bridged" rings. Each of the rings of the polycycle can be substituted with, without limitation, such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2$^{nd}$ ed.; Wiley: New York, 1991).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic, non-aromatic and inorganic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents (groups) as otherwise described herein, for example, a halogen, a hydroxyl, a carbonyl (such as a carboxyl, an alkoxycarbonyl, a formyl, or an acyl), an ether, a thioether, a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on a moiety or chemical group can themselves be substituted.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. It is acknowledged that the term "unsubstituted" simply refers to a hydrogen substituent or no substituent within the context of the use of the term.

Preferred substituents for use in the present invention include, for example, within context, hydroxyl, carboxyl, cyano (C≡N), nitro (NO$_2$), halogen (preferably, 1, 2 or 3 halogens, especially on an alkyl, especially a methyl group such as a trifluoromethyl), thiol, alkyl group (preferably, $C_1$-$C_6$, more preferably, $C_1$-$C_3$), alkoxy group (preferably, $C_1$-$C_6$ alkyl or aryl, including phenyl), ether (preferably, $C_1$-$C_6$ alkyl or aryl), ester (preferably, $C_1$-$C_6$ alkyl or aryl) including alkylene ester (such that attachment is on the alkylene group, rather than at the ester function which is preferably substituted with a $C_1$-$C_6$ alkyl or aryl group), thioether (preferably, $C_1$-$C_6$ alkyl or aryl) (preferably, $C_1$-$C_6$ alkyl or aryl), thioester (preferably, $C_1$-$C_6$ alkyl or aryl), halogen (F, Cl, Br, I), nitro or amine (including a five- or six-membered cyclic alkylene amine, including a $C_1$-$C_6$ alkyl amine or $C_1$-$C_6$ dialkyl amine), alkanol (preferably, $C_1$-$C_6$ alkyl or aryl), or alkanoic acid (preferably, $C_1$-$C_6$ alkyl or aryl). More preferably, the term "substituted" shall mean within its context of use alkyl (it is noted with respect to the use of alkyl that in context, alkylene groups as alkyl substituents are clearly contemplated by the present invention), alkoxy, halogen, hydroxyl, carboxylic acid, nitro and amine (including mono- or di-alkyl substituted amines). Any substitutable position in a compound according to the present invention may be substituted in the present invention, but preferably no more than 5, more preferably no more than 3 substituents are present on a single ring or ring system. Preferably, the term "unsubstituted" shall mean substituted with one or more H atoms.

The term "sulfamoyl" is art-recognized and includes a moiety represented by the general formula:

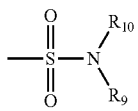

Where $R_9$ and $R_{10}$ are substituents as described above.

The term "sulfate" is art-recognized and includes a moiety represented by the general formula:

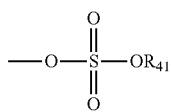

Where $R_{41}$ is an electron pair, hydrogen, alkyl, cycloalkyl or aryl.

The term "sulfonamido" is art-recognized and includes a moiety represented by the general formula:

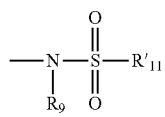

Where $R_9$ and $R'_{11}$ are as described above.

The term "sulfonate" is art-recognized and includes a moiety represented by the general formula:

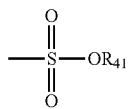

Where $R_{41}$ is an electron pair, hydrogen, alkyl, cycloalkyl or aryl.

The term "sulfoxido" or "sulfinyl" is art-recognized and includes a moiety represented by the general formula:

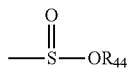

Where $R_{44}$ is is selected from the group consisting of hydrogen, alkyl, alkenyl, alkynyl, cycloalkyl, heterocyclyl, aralkyl or aryl., which groups may be optionally substituted.

The term "thioester" is art-recognized and is used to describe a group —C(O)SR$^9$ or —SC(O)R$^9$ wherein R$^9$ represents an optionally substituted hydrocarbyl group as otherwise described herein.

As used herein, the definition of each expression of alkyl, m, n, etc. when it occurs more than once in any structure, is intended to reflect the independence of the definition of the same expression in the structure, whether the term "independently" or a related term is expressly used. When a range of components, atoms, substituents, etc. is used, it is understood that each number/element falling within the range is disclosed and described. Thusly a $C_1$-$C_6$ alkyl group refers individually to a methyl group ($C_1$), ethyl group ($C_2$), propyl or isopropyl ($C_3$), butyl, iso-butyl, sec-butyl ($C_4$), pentyl, isopentyl, neopentyl, etc. ($C_5$), hexyl, etc. ($C_6$).

By way of example, certain preferred aromatic and aliphatic rings and their derivatives and substituents which may be used as pharmacophores or substituents in compounds according to the present invention include, but are not limited to, phenyl, benzyl, pyridine, cyclohexadiene, dihydropyridine, tetrahydropyridine, piperidine, pyrazine, tetrahydro-pyrazine, dihydro-pyrazine, piperazine, pyrimidine, dihydropyrimidine tetrahydro-pyrimidine, hexahydro-pyrimidine, pyrimidinone, triazine, dihydro-triazine, tetrahydro-triazine, triazinane, tetrazine, dihydro-tetrazine, tetrahydro-tetrazine, tetrazinane, pyrrol, dihydro-pyrrole, pyrrolidine, imidazolidine, dihydro-imidazolidine, imidazole, dihydro-imidazole, azetidine, triazole, dihydro-triazole, triazolidine, tetrazole, dihydro-tetrazole, tetrazolidine, diazepane, tetrahydro-diazepine, dihydro-diazepine, diazepine, oxazole, dihydrooxazole, oxazolidine, isoxazole, dihydroisoxazole, isoxazolidine, thiazole, dihydrothiazole, thiazolidine, isothiazole, dihydroisothiazole, isothiazolidine, oxadiazole, dihydrooxadiazole, oxadiazolidine, thiadiazole, dihydro-thidiazole, thidiazolidine, oxazinane, dihydro-oxazinane, dihydro-oxazine, oxazine (including morpholine), thiazinane, dihydro-thiazinane, dihydro-thiazine, thiazine (including thiomorpholine), thiazine, furan, dihydrofuran, tetrahydrofuran, thiophene, pyridazine-3,6-dione, tetrahydrothiophene, dihydrothiophene, tetrahydrothiophene, dithiolane, dithiole, dithiolone, dioxolane, dioxole, oxathiole, oxathiolane, pyridinone, dioxane, dioxanedione, benzoquinone, dihydro-dioxine, dioxine, pyran, 3,4-dihydro-2H-pyran, pyranone, 2H-pyran-2,3(4H)-dione, oxathiane, dihydro-oxathiine, oxathiine, oxetane, thietane, thiazeto, cyclohexadienone, lactam, lactone, piperazinone, pyrroledione, cyclopentenone, oxazete, oxazinanone, dioxolane, 3,4-dihydro-2H-thiopyran 1,1-dioxide, dioxolanone, oxazolidinone, oxazolone, thiane 1-oxide, thiazinane 1-oxide, tetrahydro-thiopyran, thiane 1,1-dioxide, dioxazinane, pyrazolone, 1,3-thiazete, thiazinane 1,1-dioxide, 6,7-dihydro-5H-1,4-dioxepine, 1,2-dihydropyridazin-3(4H)-one, pyridine-2,6(1H,3H)-dione, sugar (glucose, mannose, galactose, fucose, fructose, ribose) and derivatives.

Bicyclic and fused rings include, for example, naphthyl, quinone, quinolinone, dihydroquinoline, tetrahydroquinoline, naphthyridine, quinazoline, dihydroquinazoline, tetrahydroquinazoline, quinoxaline, dihydroquinazoline, tetrahydroquinazoline, pyrazine, quinazoline-2,4(1H,3H)-dione, isoindoline-1,3-dione, octahydro-pyrrolo-pyridine, indoline, isoindoline, hexahydro-indolone, tetrahydropyrrolo oxazolone, hexahydro-2H-pyrrolo[3,4-d]isoxazole, tetrahydro-1,6-naphthyridine, 2,3,4,5,6,7-hexahydro-1H-pyrrolo[3,4-c]pyridine, 1H-benzo[d]imidazole, octahydropyrrolo[3,4-c]pyrrole, 3-azabicyclo[3.1.0]hexane, 7-azabicyclo[2.2.1]hept-2-ene, diazabicyclo-heptane, benzoxazole, indole, 1,4-diazabicyclo[3.3.1]nonane, azabicyclo-octane, naphthalene-1,4-dione, indene, dihydroindene, 2,3,3a,7a-tetrahydro-1H-isoindole, 2,3,3a,4,7,7a-hexahydro-1H-isoindole, 1,3-dihydroisobenzofuran, 1-methyl-3a,4,5,6,7,7a-hexahydro-1H-indole, 3-azabicyclo[4.2.0]octane, 5,6-dihydrobenzo[b]thiophene, 5,6-dihydro-4H-thieno[2,3-b]thiopyran, 3,4-dihydropyrazin-2(1H)-one, 2H-benzo[b][1,4]thiazine, naphthyridin-4(1H)-one, octahydropyrrolo[1,2-a]pyrazine, imidazo-pyridazine, tetrahydroimidazo-pyridazine, tetrahydropyridazine, thiazinone, 5-thia-1-azabicyclo[4.2.0]oct-2-en-8-one, 4-thia-1-azabicyclo[3.2.0]heptan-7-one, 1,6,7,8-tetrahydroimidaz[4,5-d][1,3]diazepine, 8H-thiazolo[4,3-c][1,4]oxazin-4-ium, 8H-thiazolo[4,3-c][1,4]thiazin-4-ium, pteridine, thiazolo[3,4-a]pyrazin-4-ium, 7-(methylimino)-7H-pyrrolo[1,2-c]thiazol-4-ium, thiazolo-pyrazine, 3,7-dioxabicyclo[4.1.0]hept-4-ene, 6,7-dihydro-5H-pyrrolo[1,2-a]imidazole, 3,3a-dihydrofuro[3,2-b]furan-2(6aH)-one, tetrahydro-3aH-[1,3]dioxolo[4,5-c]pyrrole, 7-ethylidene-7H-pyrrolo[1,2-c]thiazol-4-ium, hexahydro-1H-pyrrolo[2,1-c][1,4]oxazine, 6,7,8,8a-tetrahydro-1H-pyrrolo[2,1-c][1,4]oxazine, 2-azabicyclo[2.2.2]oct-2-ene, 6,6a-dihydrothieno[3,2-b]furan-5(3aH)-one, 4,5-dihydropyridin-3(2H)-one, 4,7a-dihydro-3aH-[1,3]dioxolo[4,5-c]pyran, 6,7-dihydro-1H-furo[3,4-c]pyran-1,3(4H)-dione, 3,3a,4,7a-tetrahydro-2H-furo[2,3-b]pyran, 2,4a,7,7a-tetrahydro-1H-cyclopenta[c]pyridine, 4H-pyrano[3,2-b]pyridine-4,8(5H)-dione, 1,2,3,3a,4,7a-hexahydropyrano[4,3-b]pyrrole, 2,3,8,8a-tetrahydroindolizin-7(1H)-one, octahydro-1H-pyrido[1,2-a]pyrazin-1-one, 2,6,7,8,9,9a-hexahydro-1H-pyrido[1,2-a]pyrazin-1-one, 6,7,8,8a-tetrahydropyrrolo[1,2-a]pyrazin-1(2H)-one, hexahydropyrrolo[1,2-a]pyrazin-1(2H)-one, bicyclo[2.2.1]hepta-2,5-diene.

Spiro moieties: 1,5-dioxaspiro[5.5]undecane, 1,4-dioxaspiro[4.5]decane, 1,4-diazabicyclo[3.2.1]octane, 5-azaspiro[2.5]octane, 5-azaspiro[2.4]heptane, 3,9-diaza-6-azoniaspiro[5.5]undecane, 3,4-dihydrospiro[benzo[b][1,4]oxazine-2,1'-cyclohexane], 7-oxa-4-azaspiro[2.5]oct-5-ene.

In the present art, Metnase/Intnase inhibitor moieties are preferably fused to a nitrogen mustard group which can covalently bind DNA in a cross-linked form. Nitrogen mustard groups have the general form of a di-chloro moiety (e.g., di-(2-chloroethyl) linked to a single nitrogen.

Pharmaceutical compositions comprising combinations of an effective amount of at least one difunctional Metnase and/or Intnase inhibitor compound according to the present invention, and one or more of the compounds otherwise described herein, all in effective amounts, in combination with a pharmaceutically effective amount of a carrier, additive or excipient, represents a further aspect of the present invention.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat skin cancers, psoriasis or other diseases which occur in or on the skin. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain preferably between about 0.05 milligram to about 750 milligrams or more, more preferably about 1 milligram to about 600 milligrams, and even more preferably about 10 milligrams to about 500 milligrams of active ingredient, alone or in combination with at least one additional anticancer agent which may be used to treat cancer, prostate cancer or metastatic prostate cancer or a secondary effect or condition thereof.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a male human) suffering from cancer can be treated by administering to the patient (subject) an effective amount of a Metnase/Intnase inhibitor compound according to the present invention including pharmaceutically acceptable salts, solvates or polymorphs, thereof optionally in a pharmaceutically acceptable carrier or diluent, either alone, or in combination with other known anticancer or pharmaceutical agents. These agents, for example, can assist in treating numerous cancers, including prostate cancer, including metastatic prostate cancer, or ameliorate the secondary effects and conditions associated with prostate cancer. The anticancer treatment according to the present invention can also be administered in conjunction with other conventional cancer therapies, such as radiation treatment or surgery and is applicable to a large number of cancers for which radiation therapy is an option including prostate cancer, including metastatic prostate cancer, melanoma, including metastatic melanoma, among a number of other cancers.

These compounds can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-3% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent, as are topically administered compositions.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, antibiotics, antifungals, antiinflammatories, or antiviral compounds. In certain preferred aspects of the invention, one or more chimeric antibody-recruiting compound according to the present invention is coadministered with another anticancer agent and/or another bioactive agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Synthetic Chemistry

The compounds according to the present invention may be prepared using techniques which are well-known in the art. Chemical synthetic approaches are well-known as exemplified in related patents, U.S. Pat. Nos. 7,169,780; 7,538,112; 7,538,112; 7,138,408; 7,517,532; 7,399,763; 7,479,497; 7,148,237; 7,358,249; 7,157,447; 7,368,571; 7,135,467; 7,468,375; 7,135,482; 7,135,482; 7,459,459; 7,115,601; 7,109,201; 7,109,186; 7,037,908; 7,001,912; 7,015,212, each of which patent is incorporated by reference in its entirety herein. The approach uses standard functional group chemistry according to well-known reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the known reaction schemes in the art. It is noted here that all of the chemical compounds contain a quinolinone pharmacophore containing a carboxylic acid group on the carbon alpha to the keto group within the quinolinone moiety (a 4-keto-3-carboxylic acid quinoline pharmacophore). This pharmacophore is well known in the art and chemical synthetic approaches which produce the basic pharmacophore and allow flexibility to provide the various substituents on compounds according to the present invention are well within the routineer's skill.

In an exemplary synthesis, compound WW-10 (FIG. 19) provides a synthesis which may be used by analogy to provide synthetic routes to the compounds according to the present invention. In general, the synthetic schemes proceed by condensing a functionalized compound, such as, for example a compound A as depicted in scheme I, below, which contains the 2,2,-dichloro-diethylamine group onto a compound B which contains a 3-carboxy-quinolin-4-one moiety (the amine group of the quinoline moiety is readily derivatized to provide an isopropyl group and/or a cyclopropyl group), to provide the corresponding bifunctional anticancer agent WW-10 as set forth below.

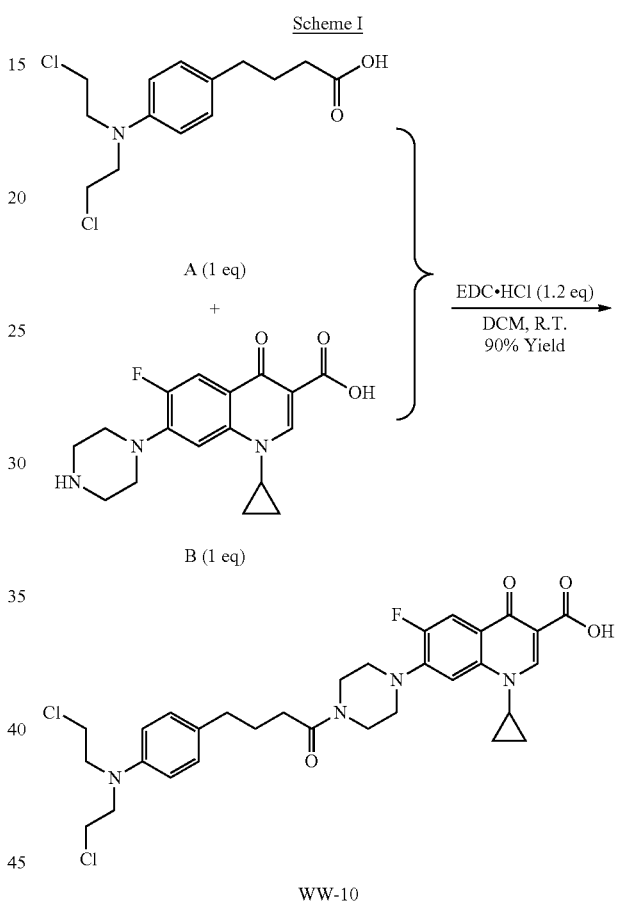

In exemplary scheme I, above, ciprofloxacin (comp. B, 109 mg, 0.33 mmol) in dichloromethane was added dropwise to a solution of 100 mg of chlorambucil (A, 0.33 mmol) and EDC.HCl (76 mg, 0.40 mmol) at 0° C. in dichloromethane. After 3 h stirring, water was added to the reaction mixture, and the mixture was extracted with dichloromethane. Removal of solvent gave a mixture, which was purified by silica gel column chromatography with DCM/MeOH (20:1) to give a pure compound in yield 90%.

In an additional exemplary synthesis, compound WW-01 (FIG. 19) was prepared according to the synthesis which is set forth in scheme II, below. In this scheme, indole alkylene carboxylic acid compound 1 (compound A) was condensed onto the quinilin-4-one compound 2 (1-cyclopropyl-3-carboxy-6-fluoro-7-piperazinyl-quinolin-4-one) at the secondary amine of the piperazinyl group to form WW-01 as indicated in high yield.

Scheme II

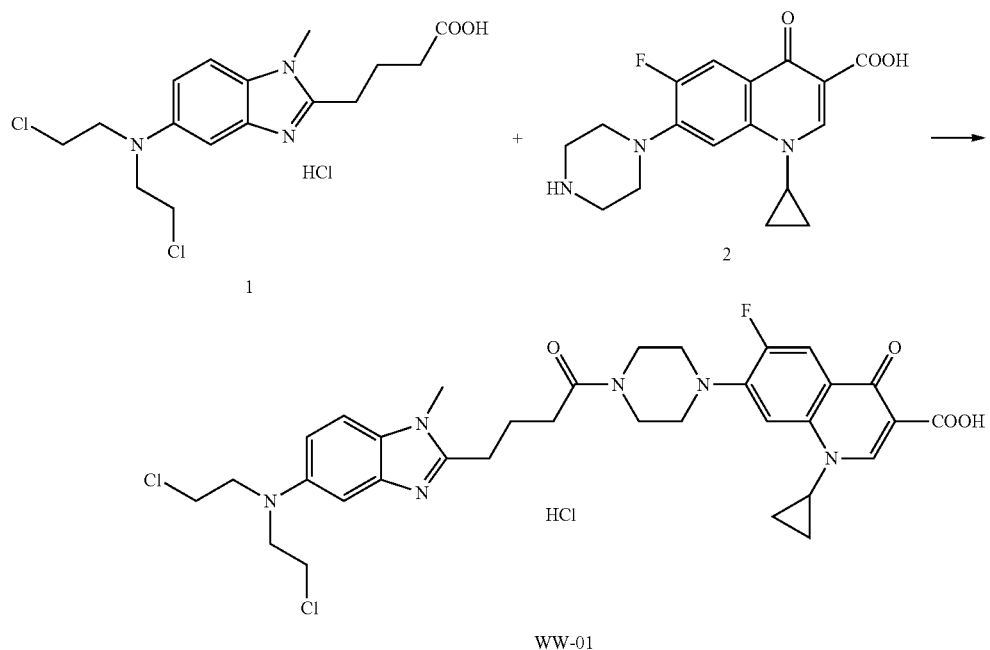

WW-01

In Scheme II above, to compound 1 (395 mg, 1.0 mmol) in $CH_2Cl_2$ (6 mL) was added EDC.HCl (211 mg, 1.1 mmol) at 0° C. The reaction mixture was stirred for 15 min at 0° C., and then compound 2 (331 mg, 1.0 mmol) in $CH_2Cl_2$ (4 mL) was added. The reaction was stirred for 1 h at rt, water (50 mL) and EtOAc (100 mL) were added, filter through filter paper and the solid was washed with EtOAc and dried over vacuum. Pure product (517 mg) was obtained in 73% yield. $^1$H NMR (300 MHz, CDCl$_3$): δ 8.78 (s, 1H), 8.05 (d, J=12.9 Hz, 1H), 7.39 (d, J=7.2 Hz, 1H), 7.23 (d, J=9.0 Hz, 1H), 7.03 (d, J=2.4 Hz, 1H), 6.81 (dd, J=2.4, 9.0 Hz, 1H), 3.77 (s, 3H), 3.74-3.52 (m, 13H), 3.36 (m, 2H), 3.22 (m, 2H), 3.06 (t, J=6.9 Hz, 2H), 2.64 (t, J=6.6 Hz, 2H), 2.26 (m, 2H), 1.42 (m, 2H), 1.20 (m, 2H). $^{13}$C NMR (75 MHz, CDCl$_3$): δ 176.9, 170.7, 166.7, 155.1, 154.3, 151.5, 147.4, 145.3, 142.9, 138.9, 128.9, 120.1, 120.0, 112.5, 112.2, 110.8, 110.1, 108.0, 105.1, 102.2, 54.5, 49.9, 49.5, 45.1, 41.1, 40.6, 35.3, 31.8, 29.9, 26.4, 22.3, 8.2.

In similar fashion, the remaining compounds according to the present invention may be prepared generally, by introducing functional groups (leaving groups, nucleophilic groups or electrophilic groups) at the 6 and 7 positions (i.e., $R_2$ and $R_3$) of the 3-carboxy-quinolin-4-one compound which allows the introduction of a variety of substituents at the 6 and 7 positions of the quinoline moiety. In general terms, a leaving group at the 6 or 7-position, e.g., an iodo, bromo or other leaving group, will allow a nucleophilic substitution onto the carbon position of the quinolin-4-one which contains the iodo group. Amines and/or oxygen groups (hydroxyl, etc.) may be introduced into the quinolin-4-one moiety, and the nucleophilic amine and/or oxygen may be used to introduce onto the amine or oxygen a group containing an electrophilic group or a leaving group. Introduction of a carboxyl group at 6 or 7 will facilitate the introduction of a group which contains a nucleophilic group to form, for example a keto functionality, an amide or other functionality represented by compounds according to the present invention. Introduction of an alkyl group at the 1-amine position of the quinolin-4-one is generally facile and occurs using a compound containing a leaving group which is displaced when the nucleophilic amine group of the quinolin-4-one moiety is condensed onto the alkyl group. Methods for providing cyclopropyl groups on nucleophilic amines are well known in the art. Alternative syntheses based upon routine synthetic chemistry well known in the art are readily contemplated for providing compounds according to the present invention. These are all routine and represent approaches well within the skill set of the chemist of ordinary skill.

EXAMPLES

The invention may be better understood by reference to the following non-limiting examples, which are provided as exemplary of the invention. The following examples are presented in order to more fully illustrate the preferred embodiments of the invention and should in no way be construed, however, as limiting the broad scope of the invention.

Example 1

Docking Studies

Omega software (v. 2.2.1, see Boström, J.; Greenwood, J. R.; Gottfries, J.; Assessing the Performance of OMEGA with Respect to Retrieving Bioactive Conformations. *J. Mol. Graph. Model.* 2003, 21, 449-462) was used to generate 1000 conformations of each compound using RMS threshold of 0.3 and the default values for the other parameters. Fast Rigid Exhaustive Docking (FRED v. 2.2.3, see, for example, McGann, M. R.; Almond, H. R.; Nicholls, A.; Grant, J. A.; Brown, F. K.; Gaussian docking functions. *Biopolymers* 2003, 68, 76-90) was the chosen docking program and all calculations were based on the default parameters, with chemgauss3 as the scoring function and number of alternative poses (num_alt_poses)=9. VIDA (v. 3.0.0) was chosen for visual analysis of docking results, generation of pictures and molecular drawing/editing tool. Omega, FRED and VIDA are from OpenEye Scientific Software, Inc., Santa Fe, N.Mex., USA.

The three-dimensional structure of metnase transposase domain used for docking was generated by homology modeling. The crystallographic X-rays structure of this domain was determined some months after (PDB code: 3F2K) and the comparison of the α-carbons (890 pm) and all atoms (940 pm) showed that the overall difference was not significant at the structured regions comprising α-helices and β-sheets.

Initially, in the development of compounds of the invention, an alkylator moiety was linked to a dihydroquinoline core in accordance with the following structure (where R indicates substitution by various substituents):

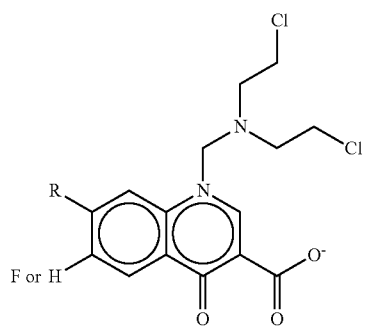

Hypothetically, derivatives having the above structure would be able to bind to Intnase and then link the alkylating portion to the DNA base pair. Once the alkylating moiety is nearby the active site, it could in principle also form a covalent bond with one of the aspartates. Docking showed that this may happen to Metnase (see the arrow in FIG. 1 which points to this region at the catalytic site).

However, the docking results using Intnase showed that there is not much space to accommodate the alkylating moiety pointed downward (i.e. in the direction of the aspartates). Hence the alkylator fragment is pointing upward, in the direction of the oncoming DNA. The DNA is usually distorted when binding to these types of enzymes, exposing the base pairs directly to the catalytic site (in which the alkylator is positioned). This molecule would then be sandwiched between Intnase and DNA in order to have this mechanism of action, forming a ternary complex intnase-compound-DNA. In addition, the portion of this compound was not a biologically active Metnase/Intnase inhibitor. Therefore, the decision was made to fuse the nitrogen mustard groups to 5483-0023, a known biologically active Metnase/Intnase inhibitor.

Structures for 4H and 4F Derivatives

Thus, future docking studies used nitrogen mustard groups fused to 5483-0023. There are two binding modes for these molecules in Intnase. Referring to FIG. 4, if the compound follows the binding pose (1), it might form a covalent bond between the alkylator tail and carboxy groups of aspartate or glutamate, placed nearby the arrowhead. But, binding as in (2) implies that there is no alkylation. It was observed that the compounds 4F and 4H could bind to one aspartate in Intnase, if this amino acid is rotated. It means that at least in principle these compounds could alkylate the aspartate if it moves its side chain to the surface, instead of interacting with a serine. This compound would probably not be able to form the covalent bond, because the alkyl group and the aspartate are still too far away.

The replacement of the N-methyl group by hydrogen in compounds 4H and 4F can increase the affinity of these molecules to Intnase if they bind like (1). This happens because the methyl group of the original compound is pointing to a tyrosine (see FIG. 4) and the replacement by hydrogen provides an extra hydrogen bonding site.

Based on the foregoing, the following compounds were selected as representative bifunctional inhibitors of Metnase and Intnase (each as has a starting structure the parent 5483-0023 compound):

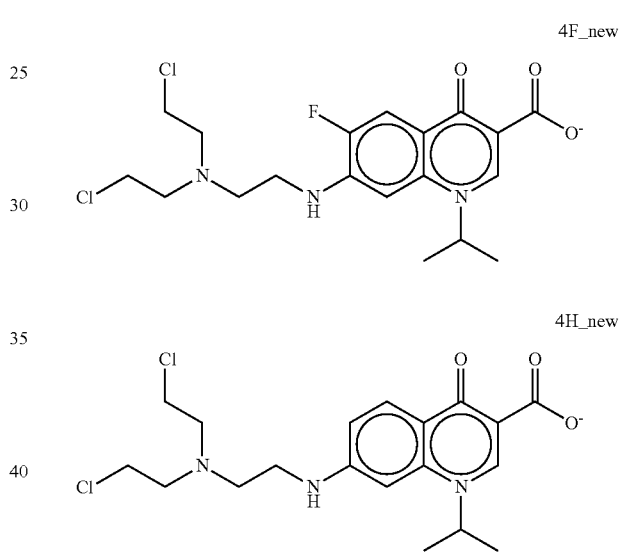

Additional new derivatives of compounds 4H and 4F were proposed with longer spacer groups, once it was determined that it was not always possible to have the compound completely stretched when in contact with the protein. One possibility came from the inclusion of a carbonyl group, now forming an amide (FIG. 2 shows the docking result for Intnase, including the two binding modes 1 and 2):

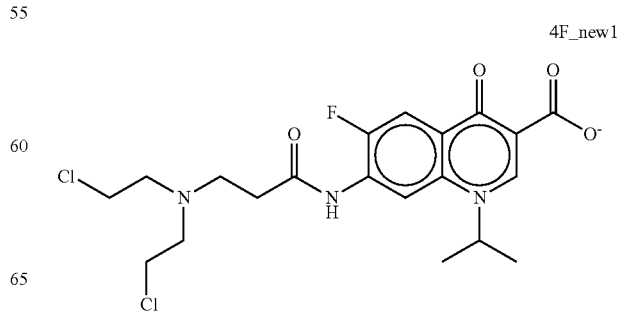

-continued

4H_new1

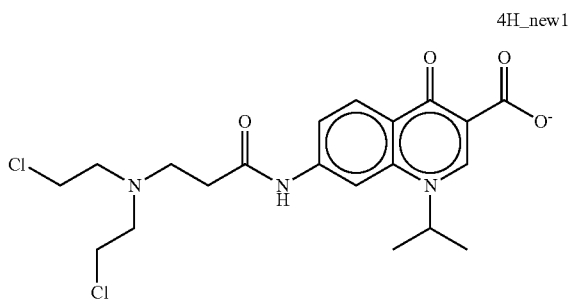

Other less flexible derivatives were also devised. These molecules bear a benzoyl group instead of the amide, leading to a reduction of the entropic penalty. This increases the distance between the two ends of the structure and extends the alkylating moiety to be further away of the catalytic site:

4F_new2

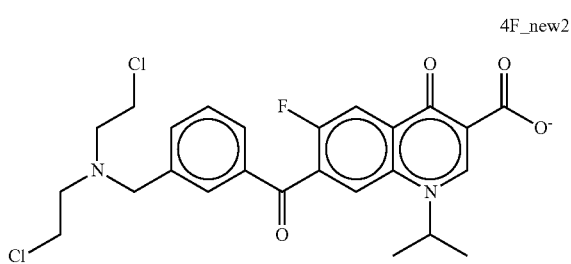

4H_new2

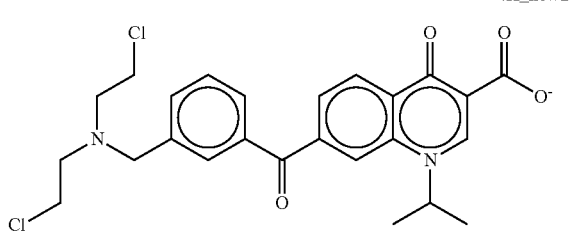

4H_new3

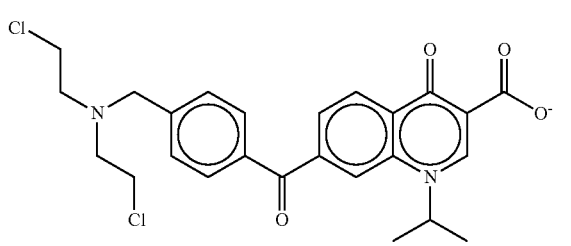

4F_new3

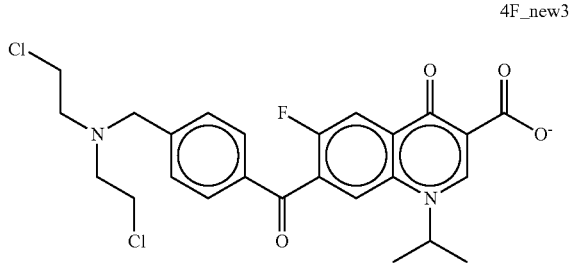

The best docking results for Metnase were achieved by derivatives 4H_new3 and 4F_new3, i.e. the fitting was better for these two derivatives in relation to the others.

Example 2

Metnase/Intnase Inhibitor ChemDiv 5483-0023 and Related Studies

Virtually screening for compounds that can dock within the active site of the transposase domain of Metnase uncovered a family of related compounds, including 5483-0023:

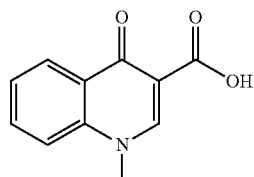

5483-0023

Metnase docking study results for 5483-0023 are shown in FIG. 5. The electrostatic surface of the enzyme is displayed on the left: high-electron density regions (red), low-electron density regions (blue), normal density (white). The right panel shows the required magnesium atom (red dot).

5483-0023 Decreases Proliferation of KG-1 Cells on its Own and Potentiates VP-16

KG-1 cells are a human acute myeloid leukemia cell line established from a patient with acute myelogenous leukemia that had evolved from an erythroleukemia. Cytotoxicity of etoposide, a semisynthetic derivative of podophyllotoxin that also is called Vepesid (Bristol; code designation VP-16-213, abbreviated VP-16), is mediated by its interaction with DNA topoisomerase II (Topo II), an ATP-dependent nuclear enzyme that regulates DNA topology by transiently breaking and rejoining double-stranded DNA to allow DNA strand passage. Under normal conditions, the formation of a DNA strand break by Topo II is followed by precise realignment and resealing of the broken ends.

The human myeloid cell line KG-1 was grown in RPMI1640 with 10% FBS. The small cell lung cancer cell line CRL5898 was grown in HITES medium (Dulbecco's medium:Ham's F12, 50:50 mix, Insulin 0.005 mg/ml Transferrin 0.01 mg/ml Sodium selenite 30 nM Hydrocortisone 10 nM beta-estradiol 10 nM HEPES 10 mM L-glutamine 2 mM (in addition to that in the base medium)). Both cell lines were seeded at 10,000 cells/ml in the appropriate medium in 6 well plates. The Chem Div compounds were resuspended as 5 mM stock solutions in DMSO. The Chem Div compounds were added alone at 2 uM and 5 uM or in combination with VP-16 (also called etoposide) at 0.05 uM. DMSO was added to the control wells. Cells were plated and treated in triplicate and counted daily for 4 days in trypan blue to assess survival and proliferation.

DNA Combing Shows that Metnase is Required for Replication Fork Progression

The replication fork is a structure that forms within the nucleus during DNA replication. It is created by helicases, which break the hydrogen bonds holding the two DNA strands together. The resulting structure has two branching "prongs", each one made up of a single strand of DNA, that are called the leading and lagging strands. DNA polymerase creates new partners for the two strands by adding nucleotides. DNA combing is a process whereby single DNA molecules bind by their extremities to a silanised surface and are then uniformly stretched and aligned by a receding air/water interface. This method, with a high resolution ranging from a few kilobases to megabases, has many applications in the field of molecular cytogenetics, allowing structural and functional analysis of DNA replication at the genome level. By labeling newly synthesized DNA during replication, immunofluorescent microscopy can then be used to measure the number and length of newly formed replication forks. We used this method to show that when Metnase is repressed there is a decrease in forks that can be restarted after fork stalling is induced.

Figure 3:
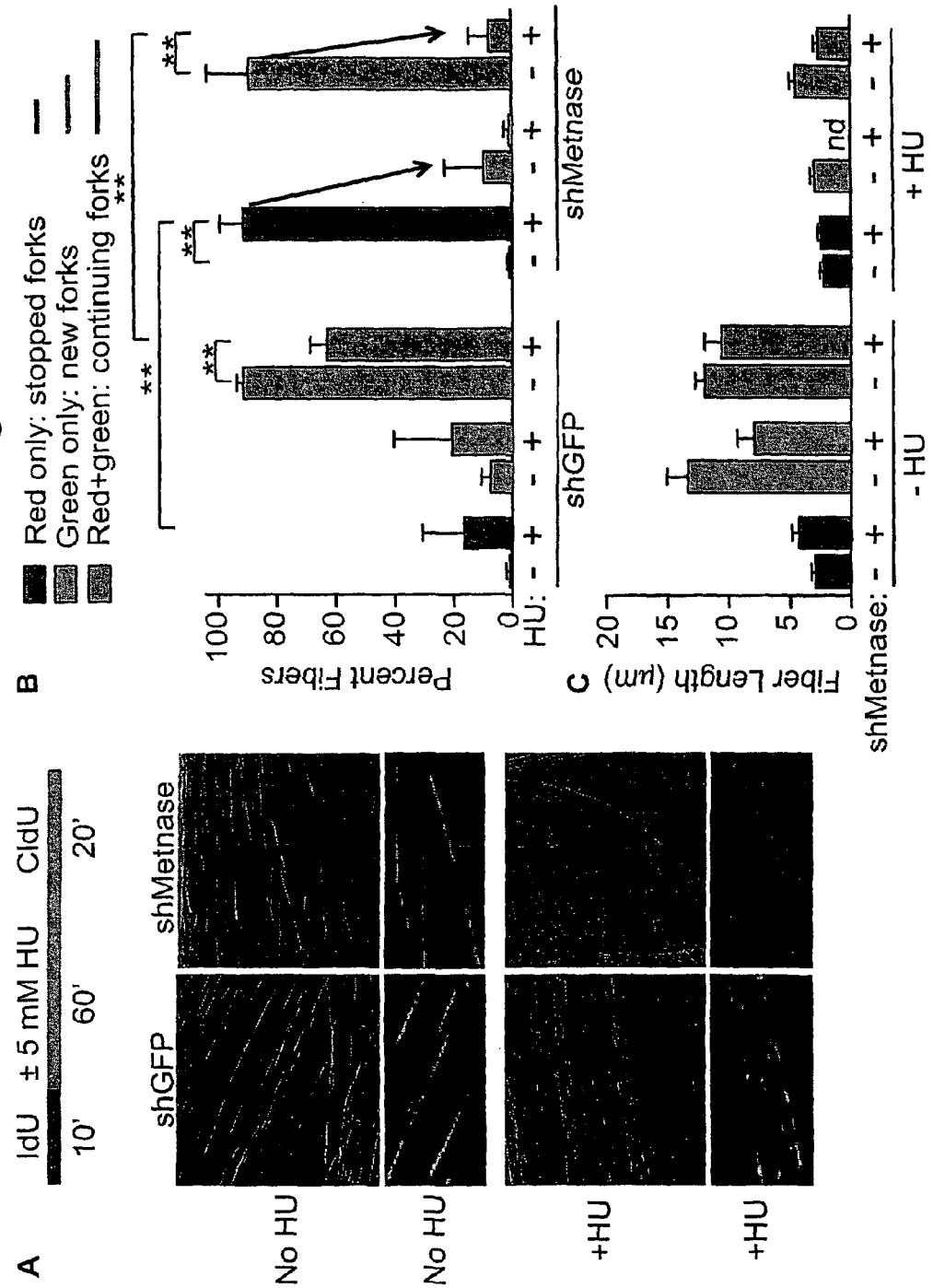
FIG. 3. DNA combing showing that after replication fork stalling from exposure to hydroxyurea (HU). Metnase is required for restarting the stalled forks. Knocking-down Metnase markedly reduced the number of forks that could be started after HU (arrows).
Figure 6:
FIG. 6. This illustrates 3-dimensionally the docking of 4H_new3 and 4F_new3 into the transposase active site of Metnase.
Figure 7:
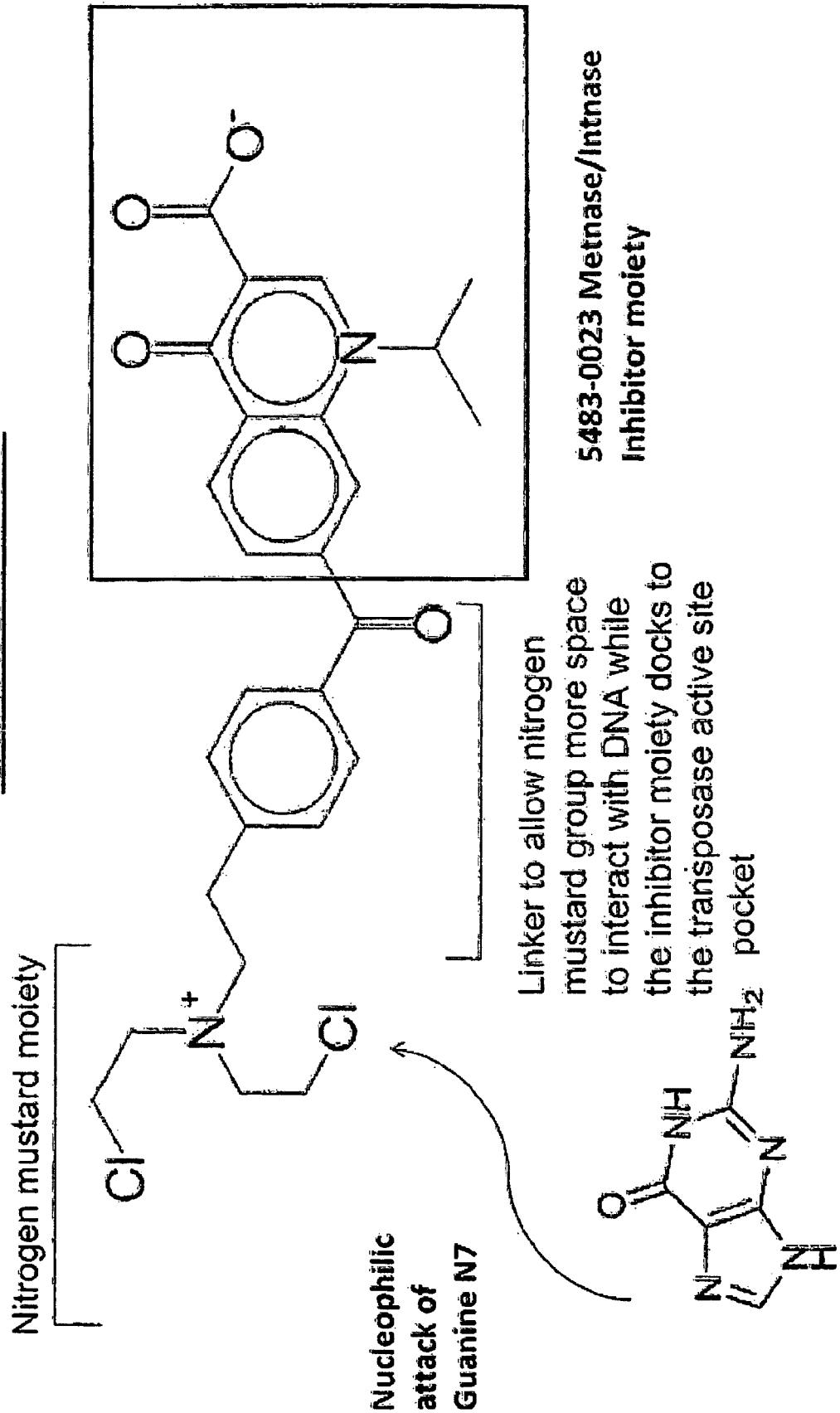
FIG. 7. Metnase and Intnase are required for replication fork progression, and cross-linking DNA stalls replication forks. This illustrates the structure of one possible bi-functional compound, 4H_new5, that cross-links DNA using a nitrogen mustard group and that docks into the active site of Metnase, thereby inhibiting it. Thus, the nitrogen mustard group's cross-linking of DNA via nucleophilic attack on guanine N7 will stall a cancer cell's replication fork, while the 5483-0023 transposase domain inhibitor will block the ability of Metnase/Gypsy Integrase to re-start the fork. These functions can occur simultaneously because of a linker group that provides space between the nitrogen mustard group and the transposase inhibitory domain of the 5483-0023 parent, allowing the nitrogen mustard group to escape the transposase active site pocket.
Figure 10:
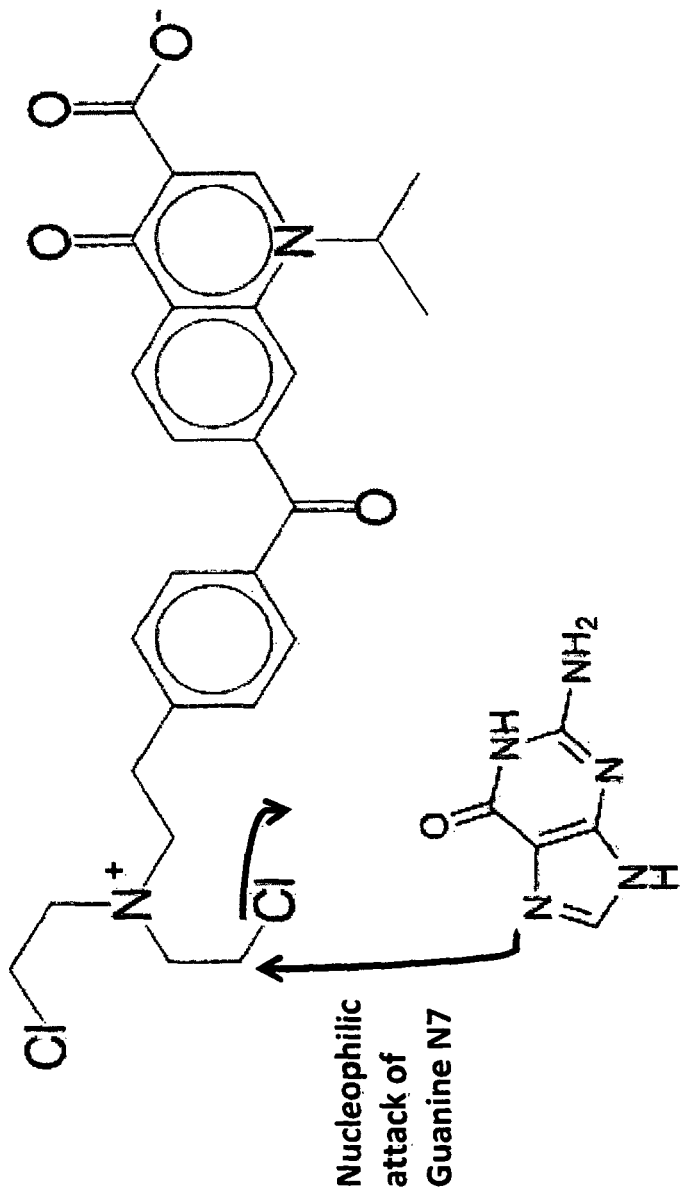
FIG. 10 shows that Metnase is required for replication fork progression, and cross-linking DNA stalls replication forks and the inventors generated a bi-functional compound that both cross-links DNA and docks into the active site of Metnase, to inhibit it.
Figure 12:
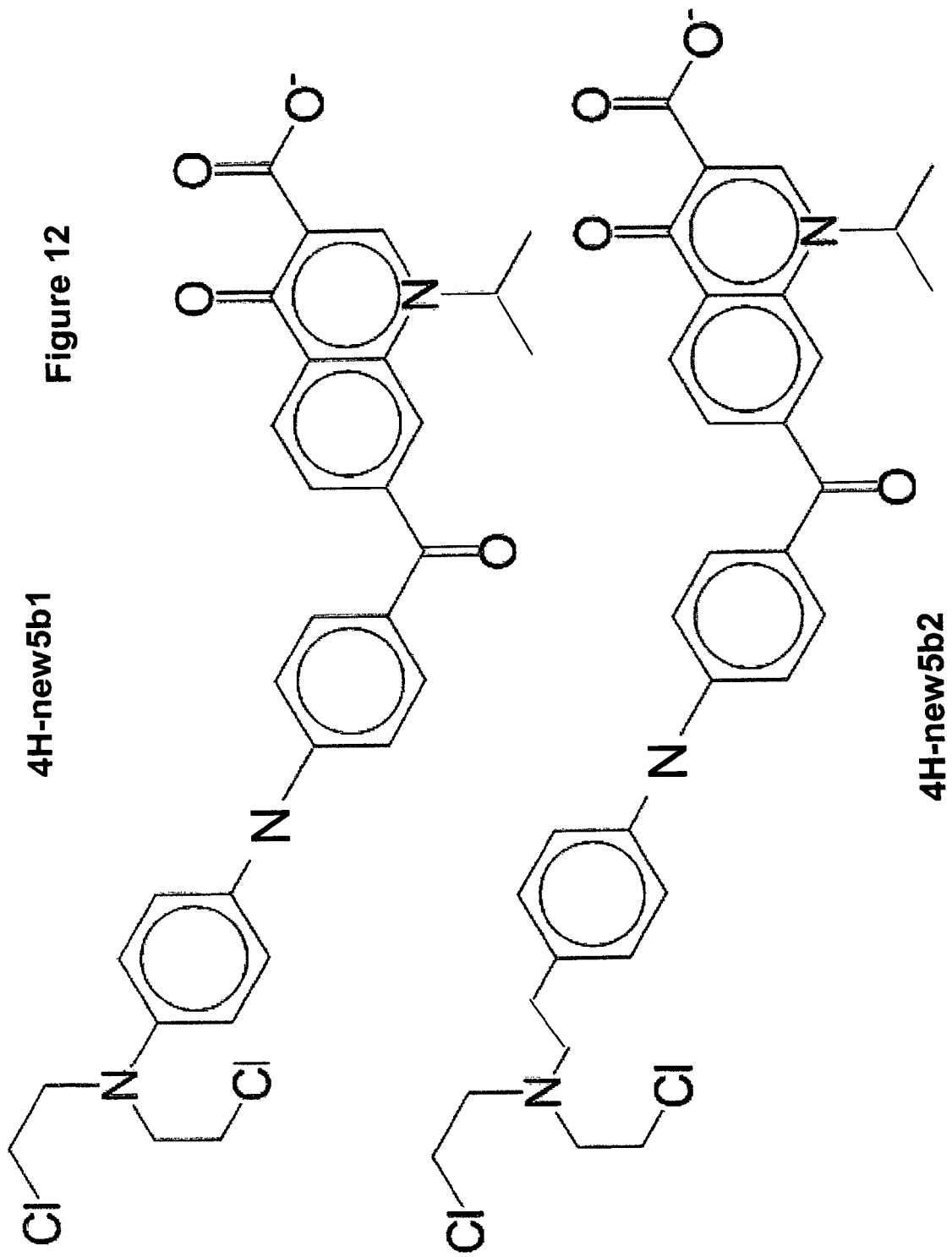
Figure 14:
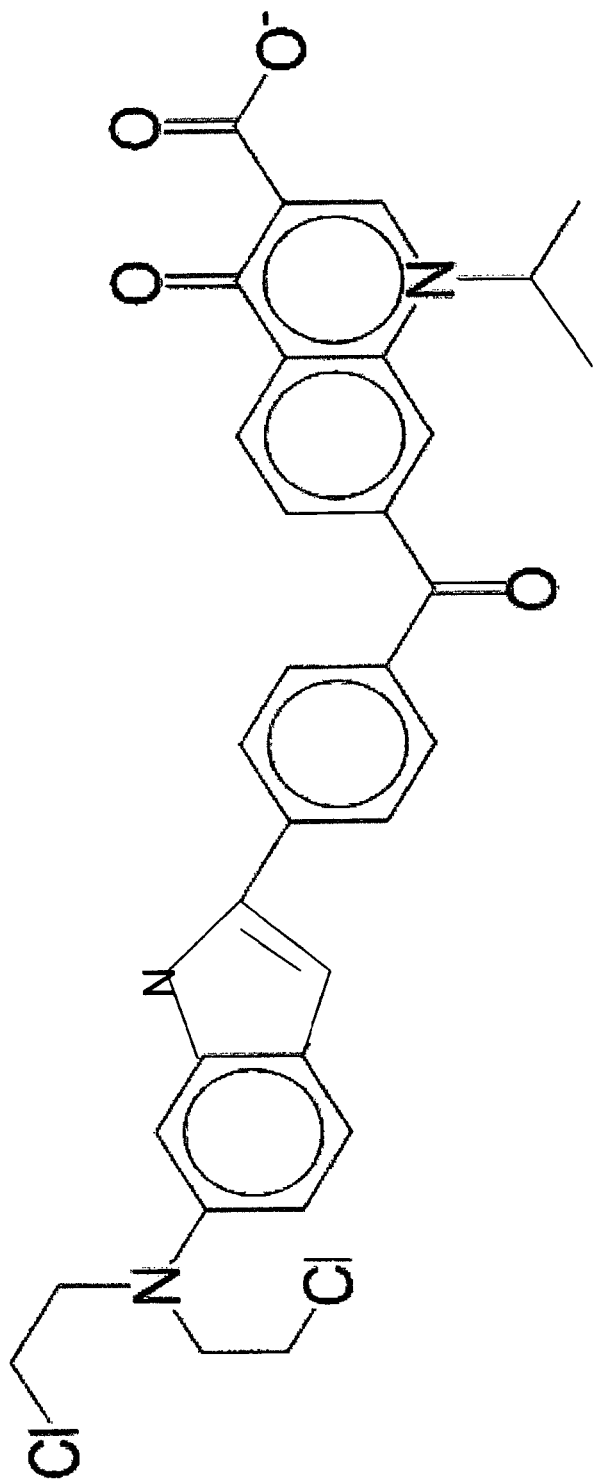
Figure 16:
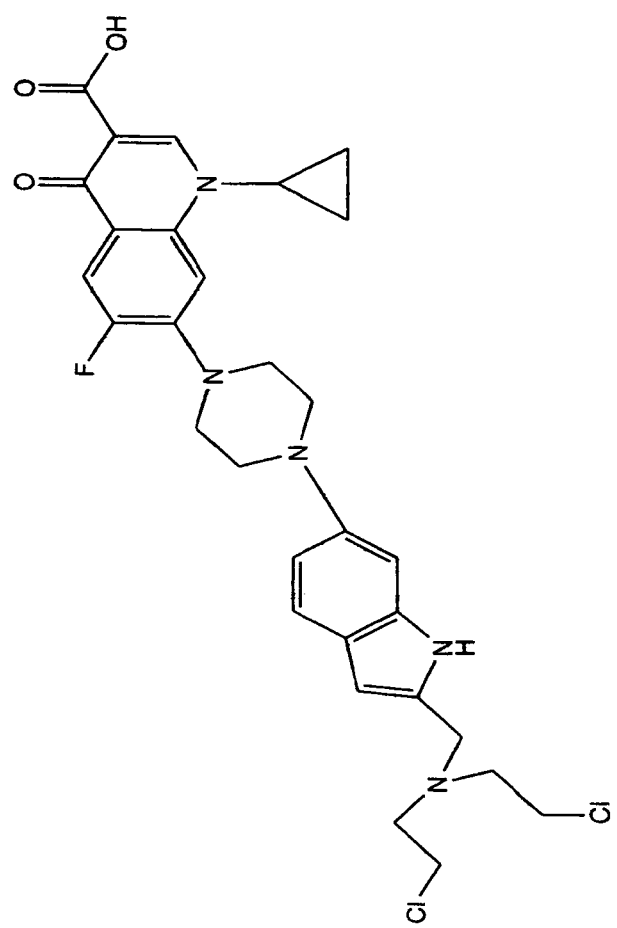

To explore the cellular response to transient replication stress, 293 cells were treated for 1 h with 5 mM of the ribonucleotide reductase inhibitor hydroxyurea (HU) or left untreated. HU induces a reversible stalling of replication forks and cells can re-enter the cell cycle after removal of the drug. As shown in FIG. 3 using the DNA combing technique Metnase is required for replication fork restart after the replication stressor hydroxyurea (HU) stalls such forks. The arrows indicate the decrease in replication fork restart after Metnase is repressed and cells are treated with HU.

5483-0023 is a Transposase Domain Inhibitor

Since Metnase and Gypsy Integrase are required for replication fork progression, and cross-linking DNA stalls replication forks, we generated a bi-functional compound that both cross-links DNA using a nitrogen mustard group and docks into the active site of Metnase, to inhibit it. Thus, the cross-linking of DNA will stall a cancer cell's replication fork, while the 5483-0023 transposase domain inhibitor will block the ability of Metnase/Gypsy Integrase to re-start the fork. See FIG. 8 and the structure of 4H-new5 below (the parent 5483-0023 structure is highlighted). It should be noted that adding a fluorine group as above could allow this agent to be administered orally.

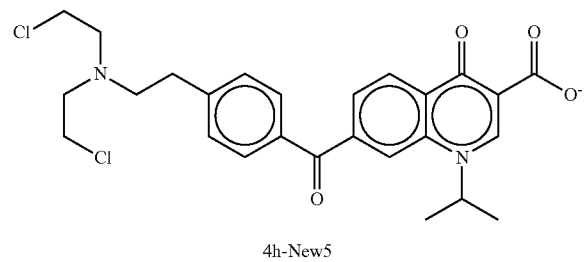

4h-New5

Docking of 4H-new5 into the active site of the Metnase Transposase domain shows that the nitrogen mustard domain is free to interact with DNA, because the linker group provides sufficient space.

Metnase docking study results for 4H-new5 and 5483-0023 are shown in FIG. 8 and are summarized in Table 1 below and are shown in FIG. 8:

TABLE 1

| Name | Total Score | Steric | Desolvation | HB Acc | HB Donor | Metal |
|---|---|---|---|---|---|---|
| 4H_new5 | −77.41 | −58.37 | 7.62 | −1.70 | 0 | −24.96 |
| 5483-0023 | −43.29 | −27.00 | 7.59 | 0 | 0 | −23.87 |

Referring to FIG. 8, the electrostatic surface of the enzyme is displayed on the left: high-electron density regions (red), low-electron density regions (blue), normal density (white). The metal atom and the catalytic aspartates are shown at the bottom of the pictures on the right. Ligands are depicted as stick figures. Only nearby amino acids (up to 350 pm away from these compounds) are represented as wireframes on the right. Atom colors: oxygen (red), carbon (gray), polar hydrogen (white), nitrogen (blue), fluorine (orange) and chlorine (green). The illustrated representation of the protein depicts helices (red) and loops (gray).

Therefore, docking of 4H-new5 into the active site of the Metnase Transposase domain shows that the nitrogen mustard domain is free to interact with DNA. In addition, the docking studies reveal that the bifunctional drug 4H_new5 binds tighter to Metnase than the parent compound 5843-0023. This demonstrates that it will be a more efficient Metnase inhibitor than the 5843-0023 parent compound.

Biological Data

The structures of various bifunctional anti-neoplastic compounds tested in colony formation assays for activity against drug resistant lung cancer cells. See FIGS. 20-41. Colony formation assays were chosen because they measure not just inhibition of cancer cell proliferation, but cancer cell death. These assays measure cell death in the cell within a population that is able to form a colony. The cell is similar in nature to a cancer stem cell. The bifunctional agents tested have an alkylating group that can cross-link DNA, and a Metnase inhibitor. The cross-linking of DNA by the alkylating group stalls the replication fork. The transposase domain DNA repair protein Metnase is required to re-start stalled replication forks. Thus, the same compound can both stall a replication fork and inhibit their re-start. Generating both the alkylating group and the Metnase inhibitor in the same compound will raise the local concentration of both adjacent to the DNA, ensuring that cross-linked DNA will have a Metnase inhibitor in the immediate vicinity.

Figure 17:
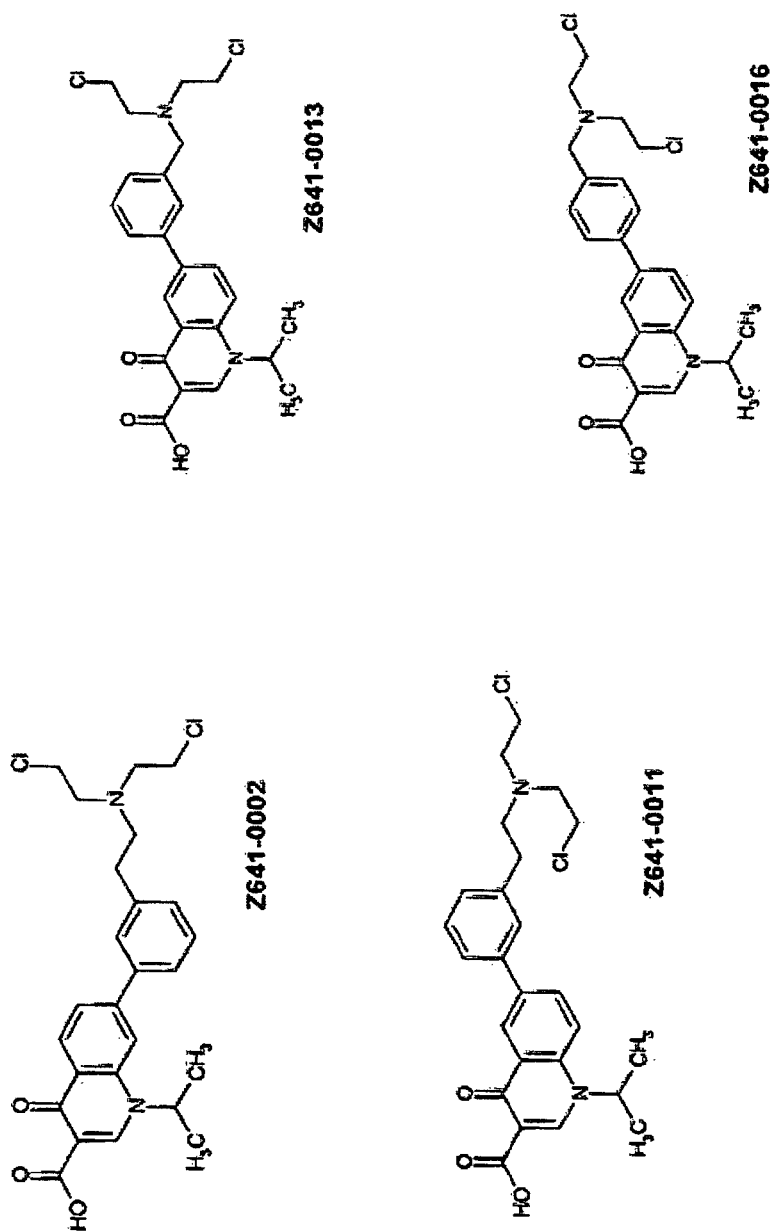
FIGS. 17-19 show additional bifunctional compounds according to the present invention, each of which contains a bifunctional alkylating moiety. These include Z641-0002, Z641-0011, Z641-0013, Z641-0016, Z641-0017, Z641-0032, Z641-0033, Z641-0035, Z641-0036, WW-10 and WW-01.
Figure 18:
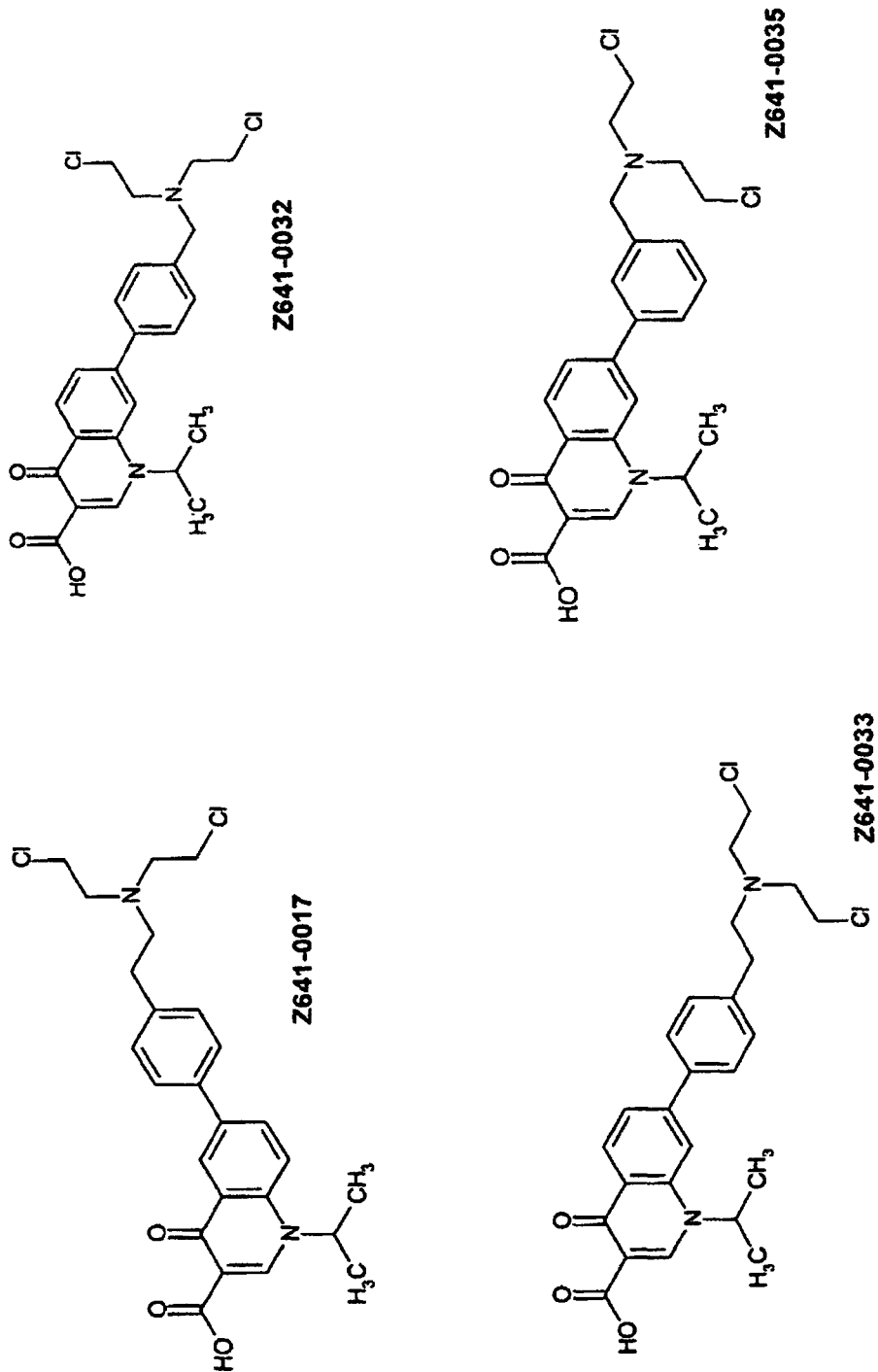
Figure 19:
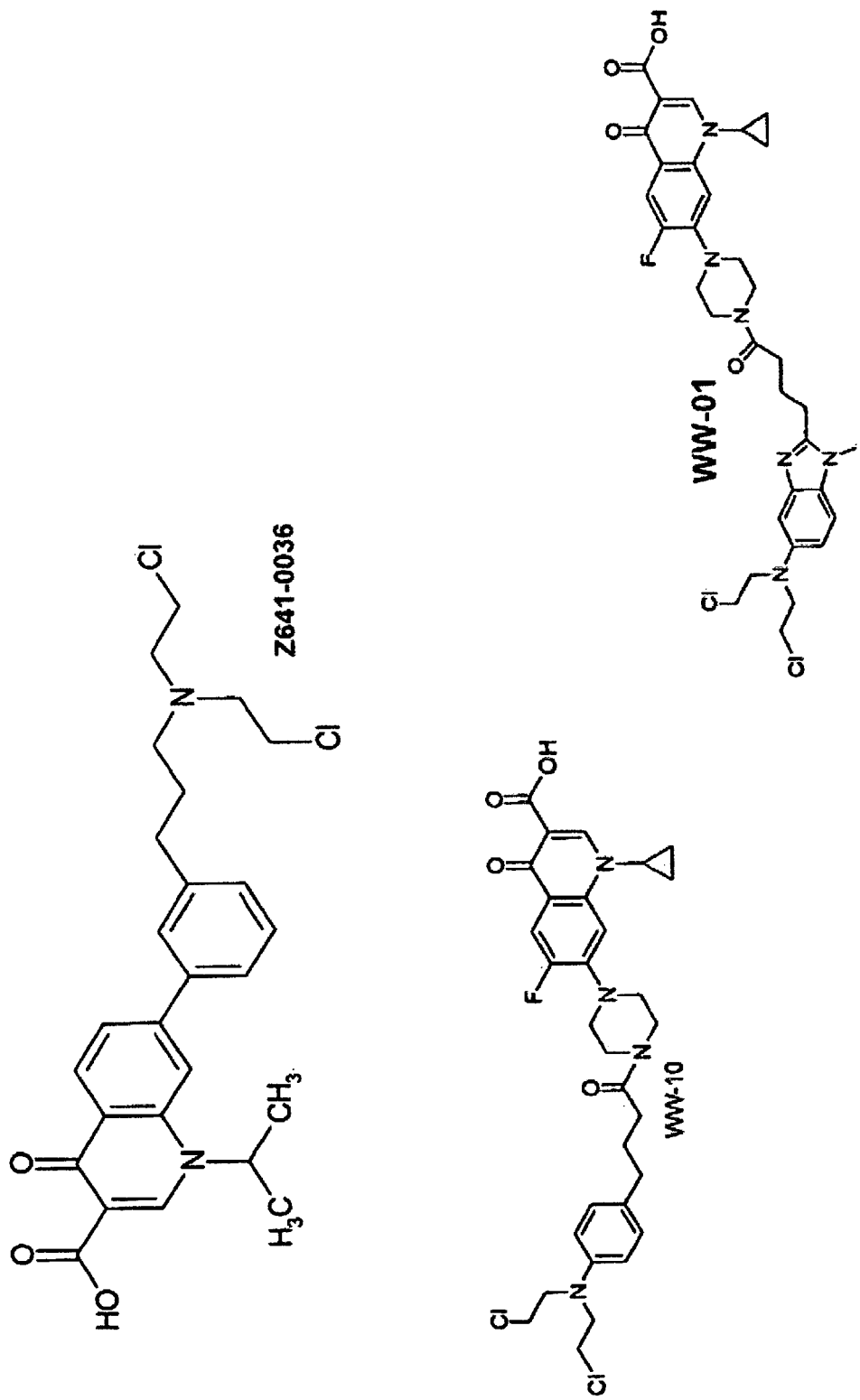
Figure 20:
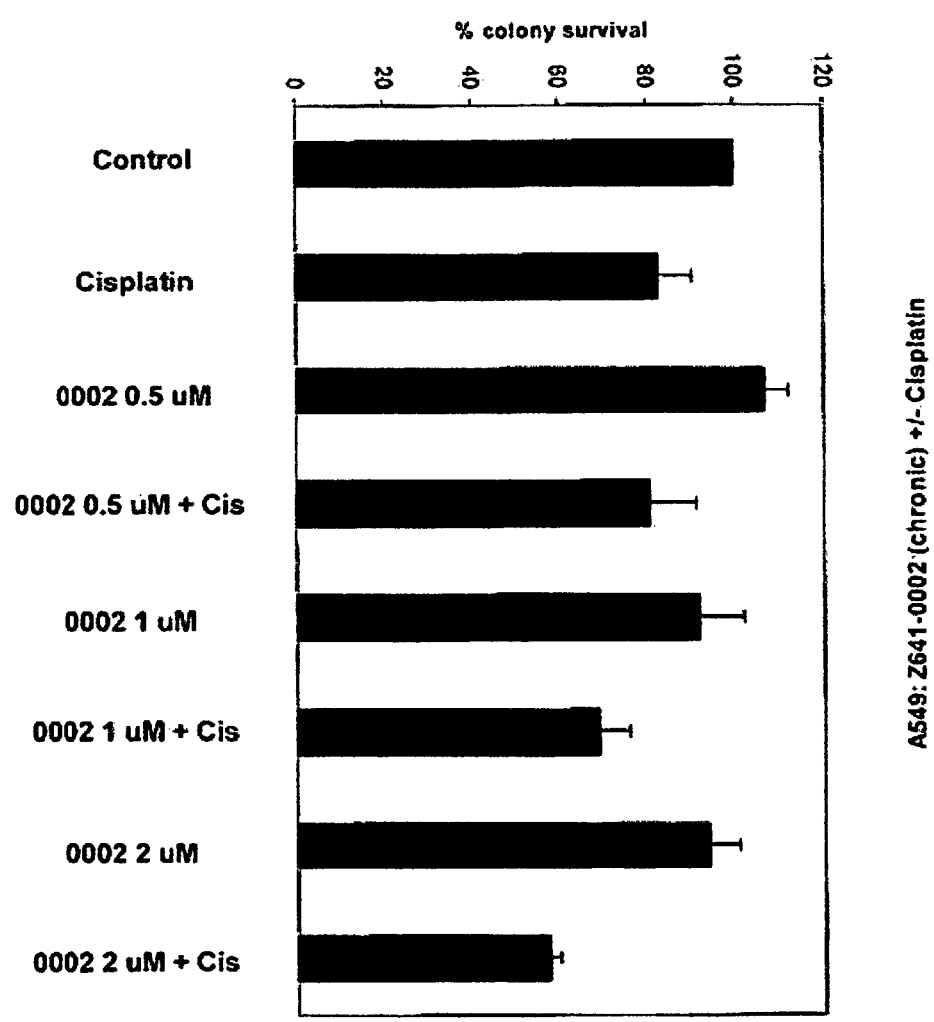
FIGS. 20-42 show the biological (anti-cancer) activity of compounds which are depicted in FIGS. 17-19 hereof and which were tested in colony formation assays for activity against cancer cells, either alone or in combination with cisplating. The colony formation assays which gave rise to the data presented in these figures is presented in the specification. Colony formation assays were chosen because they measure not just inhibition of cancer cell proliferation, but cancer cell death. These assays measure cell death in the cell within a population that is able to form a colony. This cell is similar in nature to a cancer stem cell. These bifunctional agents have an alkylating functionality which can crosslink DNA, and a Metnase inhibitor. The crosslinking of DNA by the alkylating agent stalls the replication fork. The transposase domain DNA repair protein Metnase is required to re-start stalled replication forks. Thus, the same compound can both stall a replication fork and inhibit their re-start. Generating both the alkylating group and the Metnase inhibitor in the same compound will raise the local concentration of both adjacent to the DNA, ensuring that cross-linked DNA will have a Metnase inhibitor in the immediate vicinity.
Figure 21:
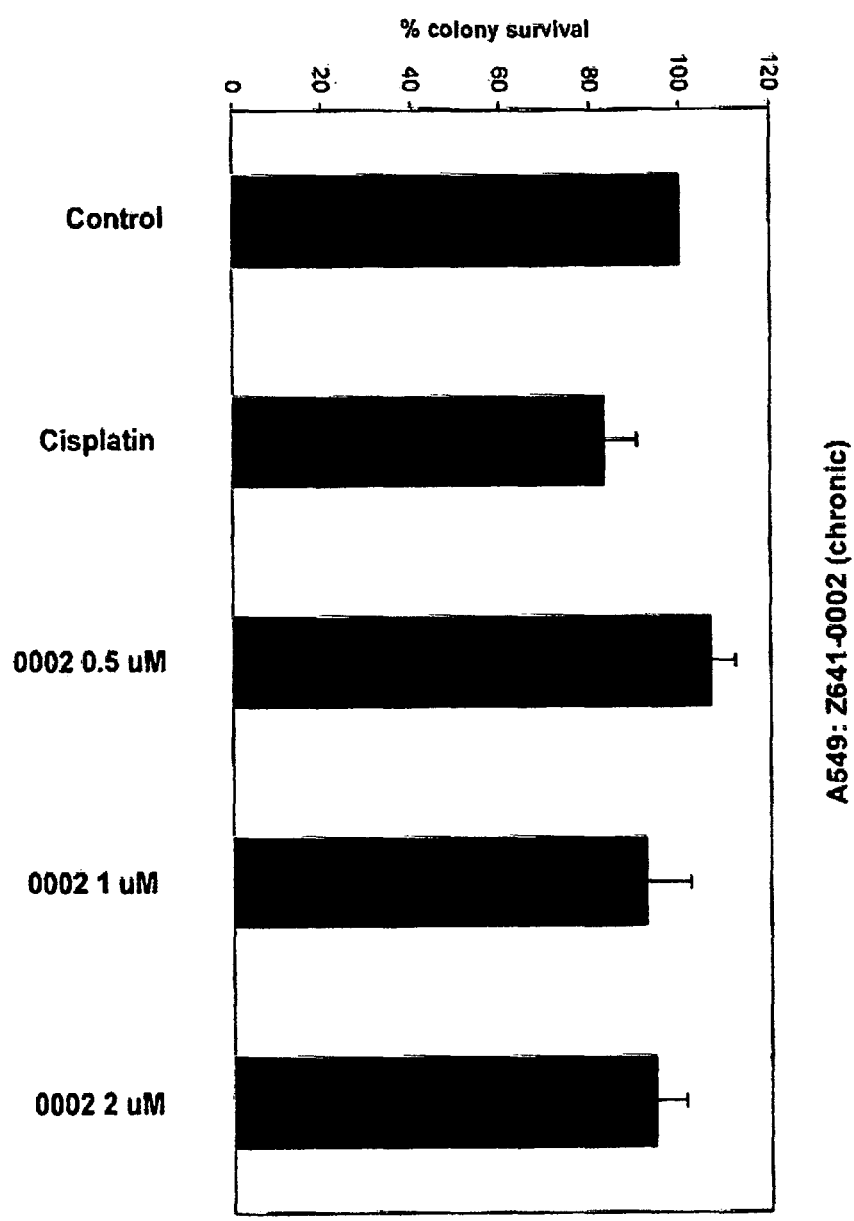
Figure 22:
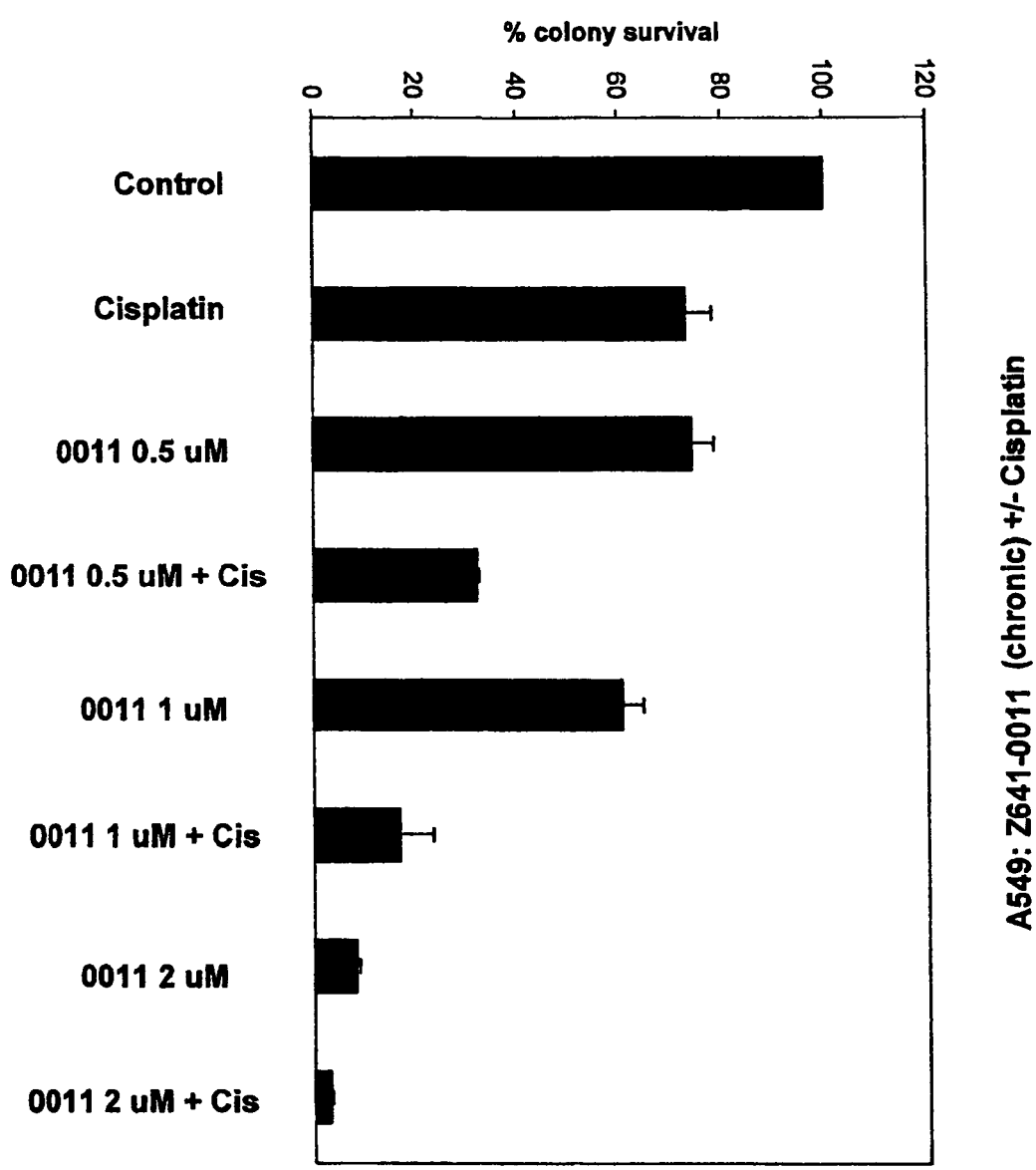
Figure 23:
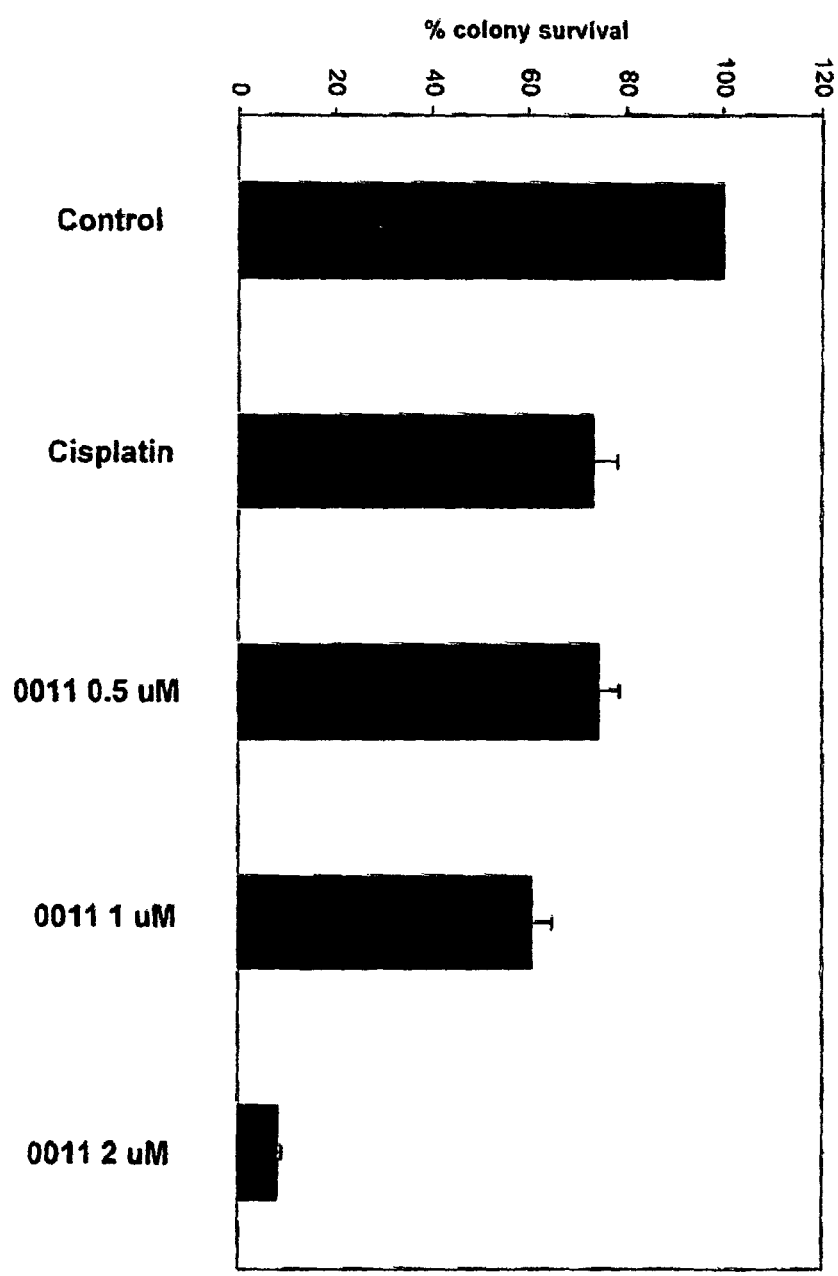
Figure 24:
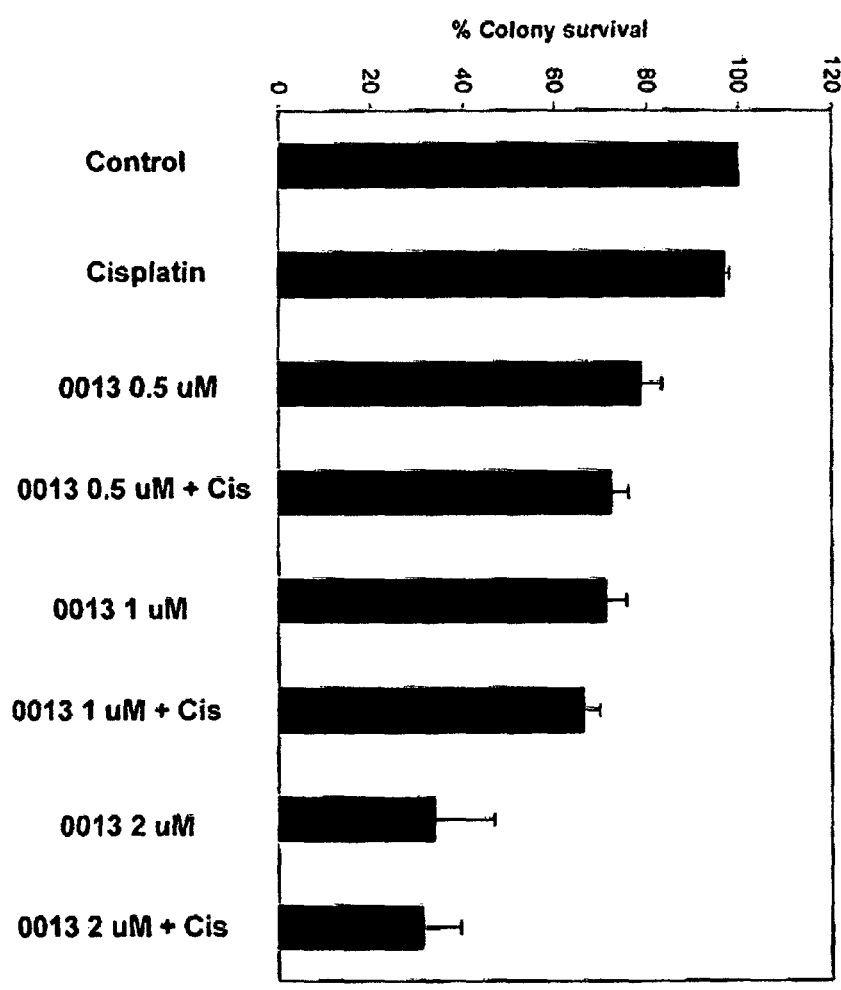
Figure 25:
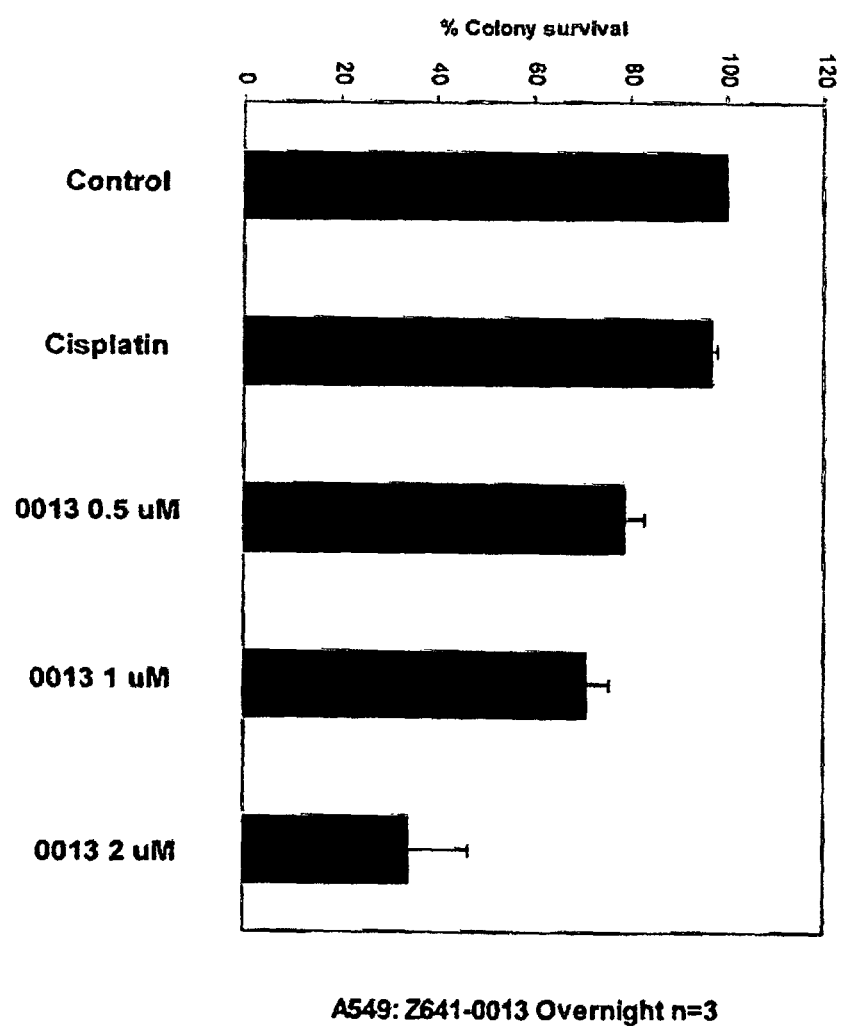
Figure 26:
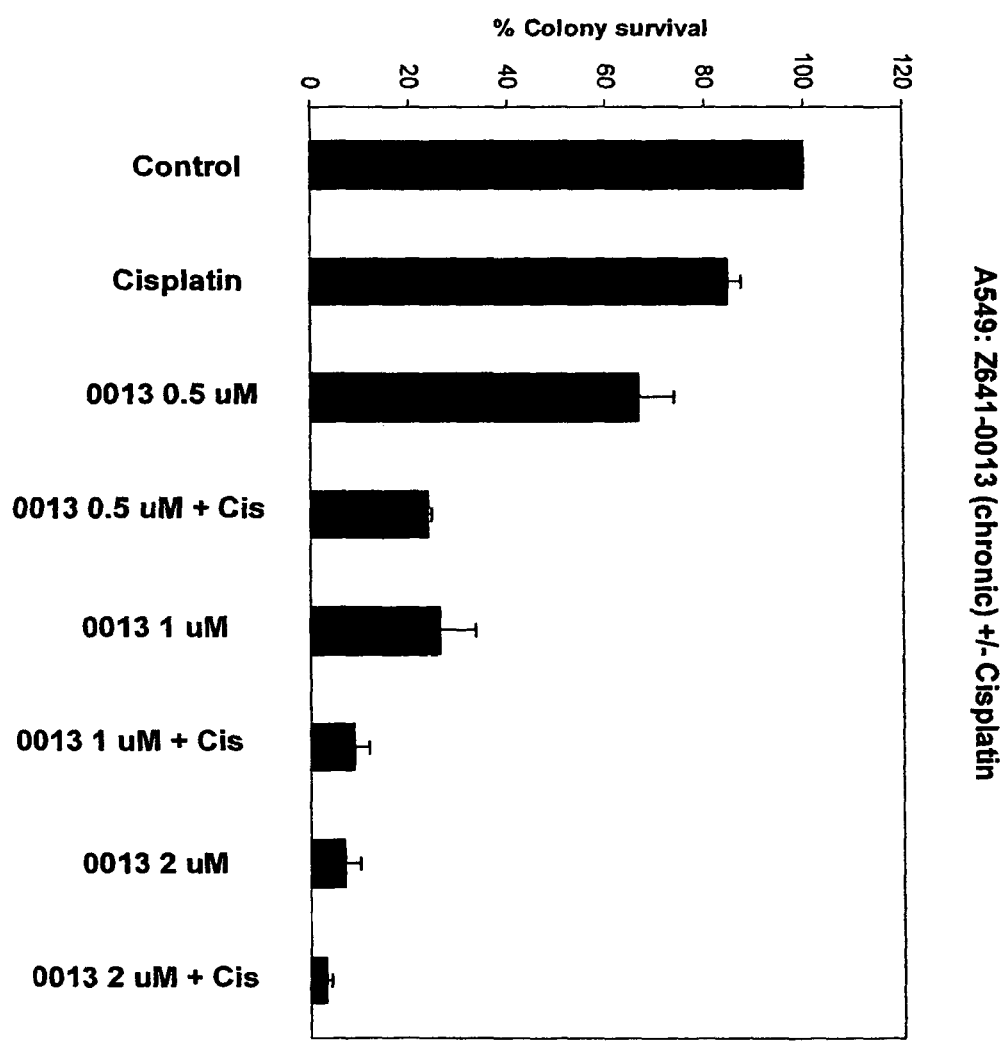
Figure 27:
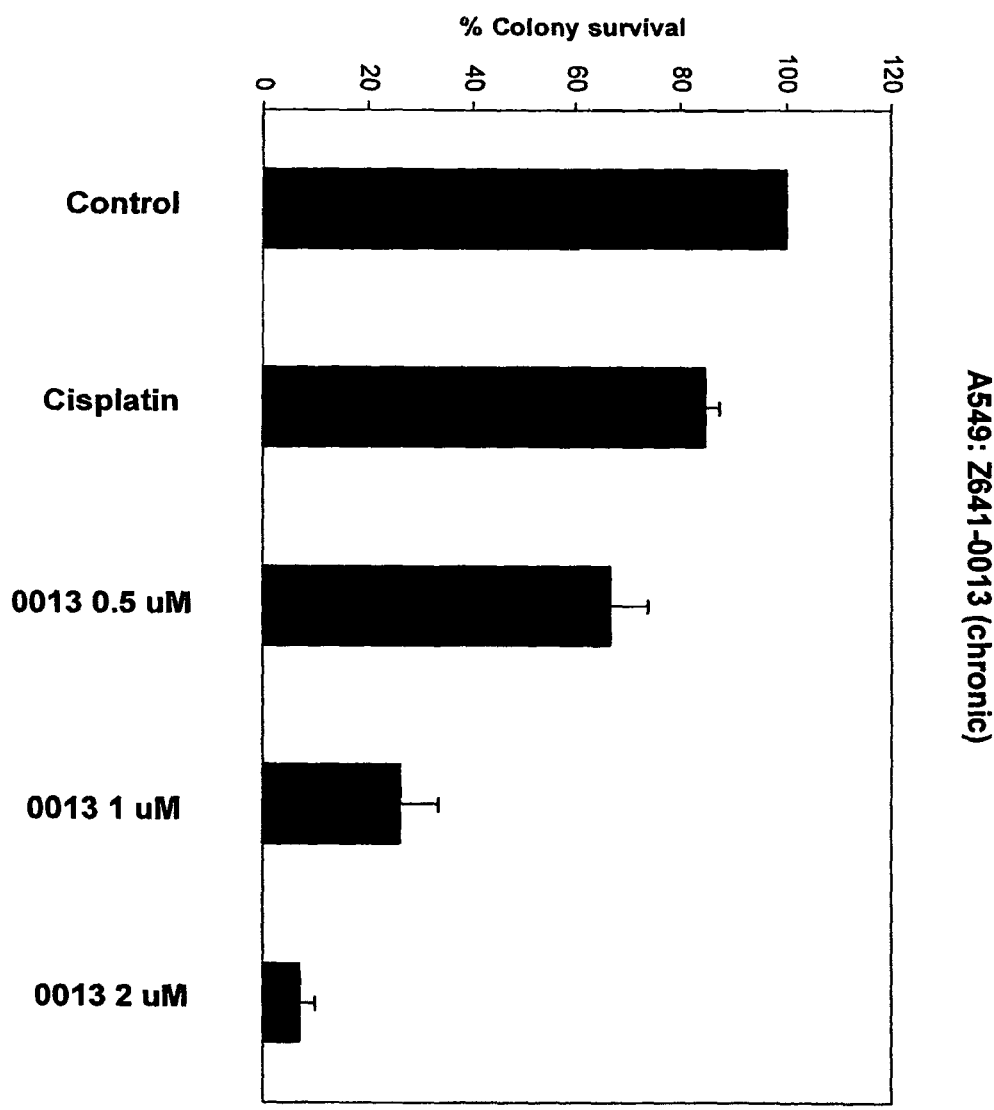
Figure 28:
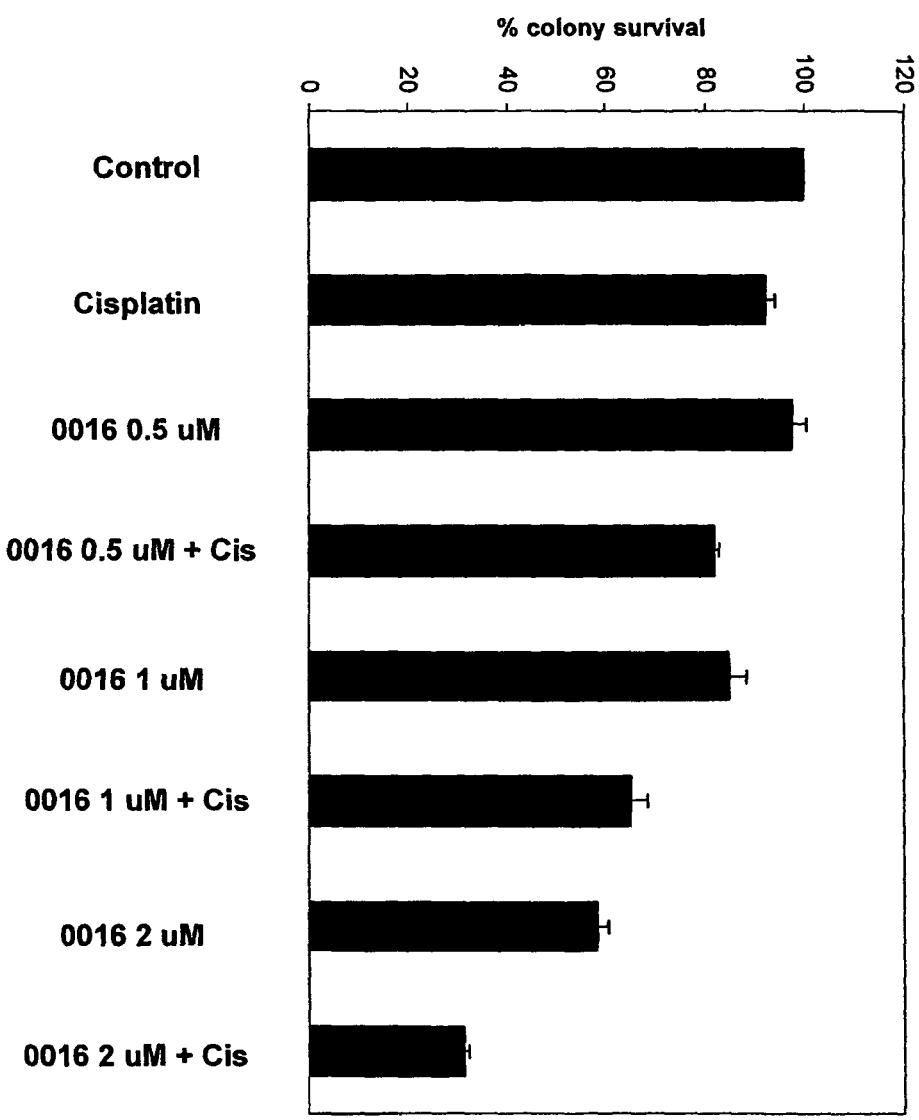
Figure 29:
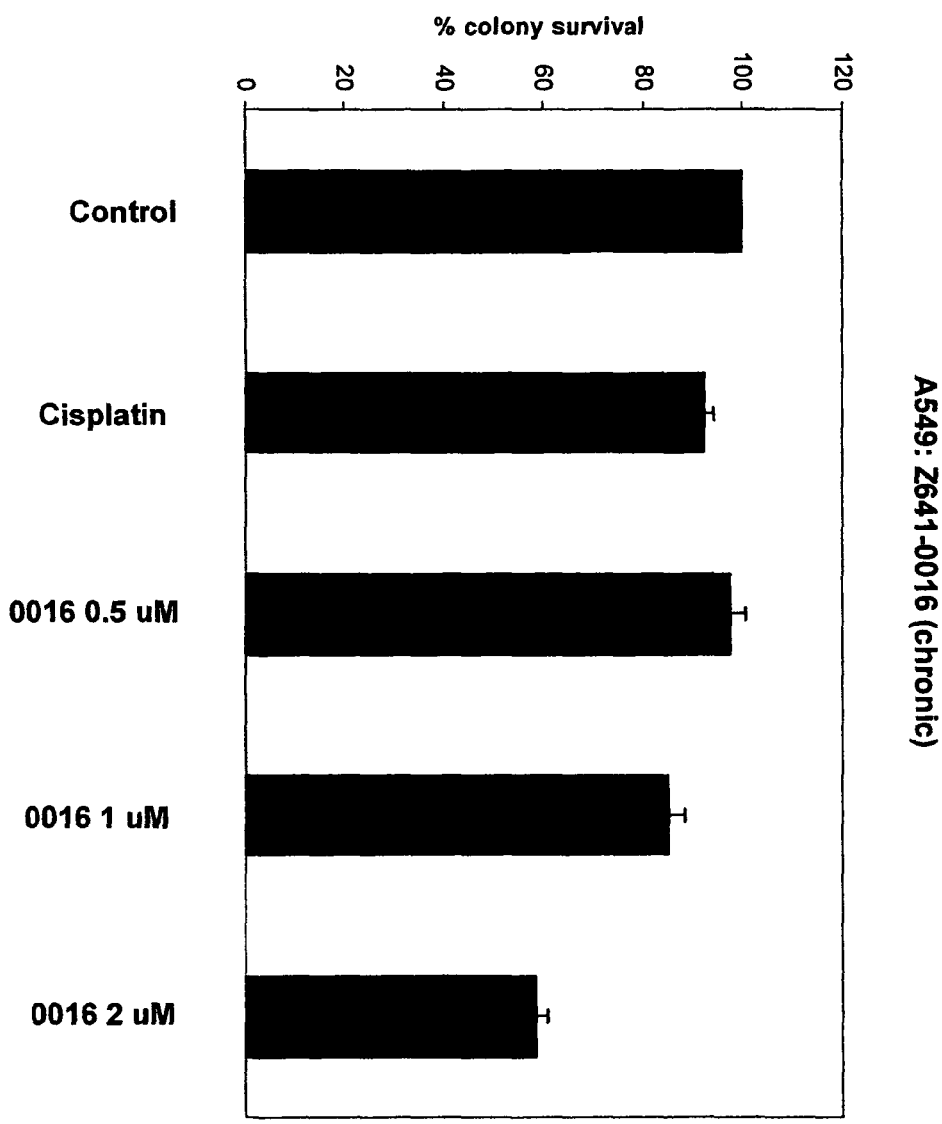
Figure 30:
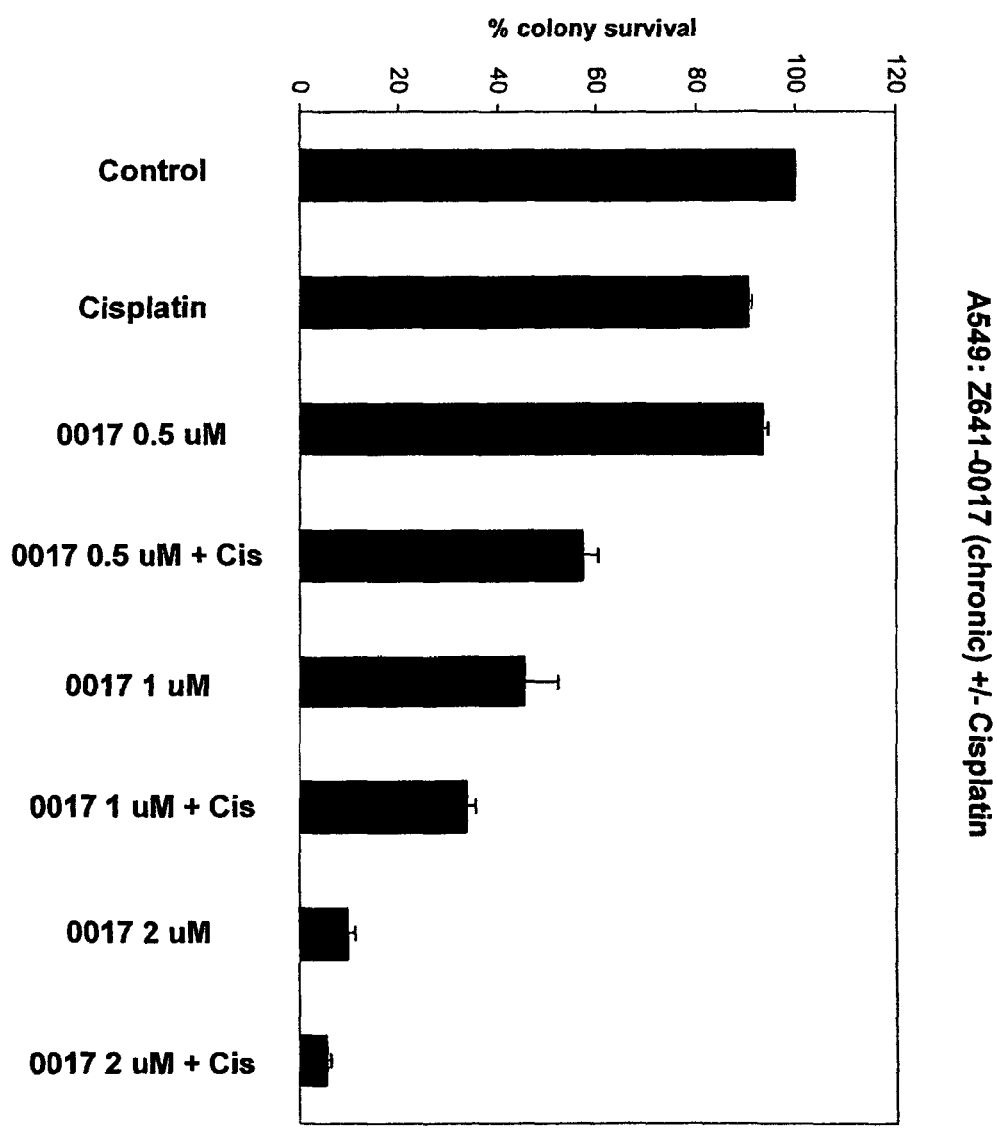
Figure 31:
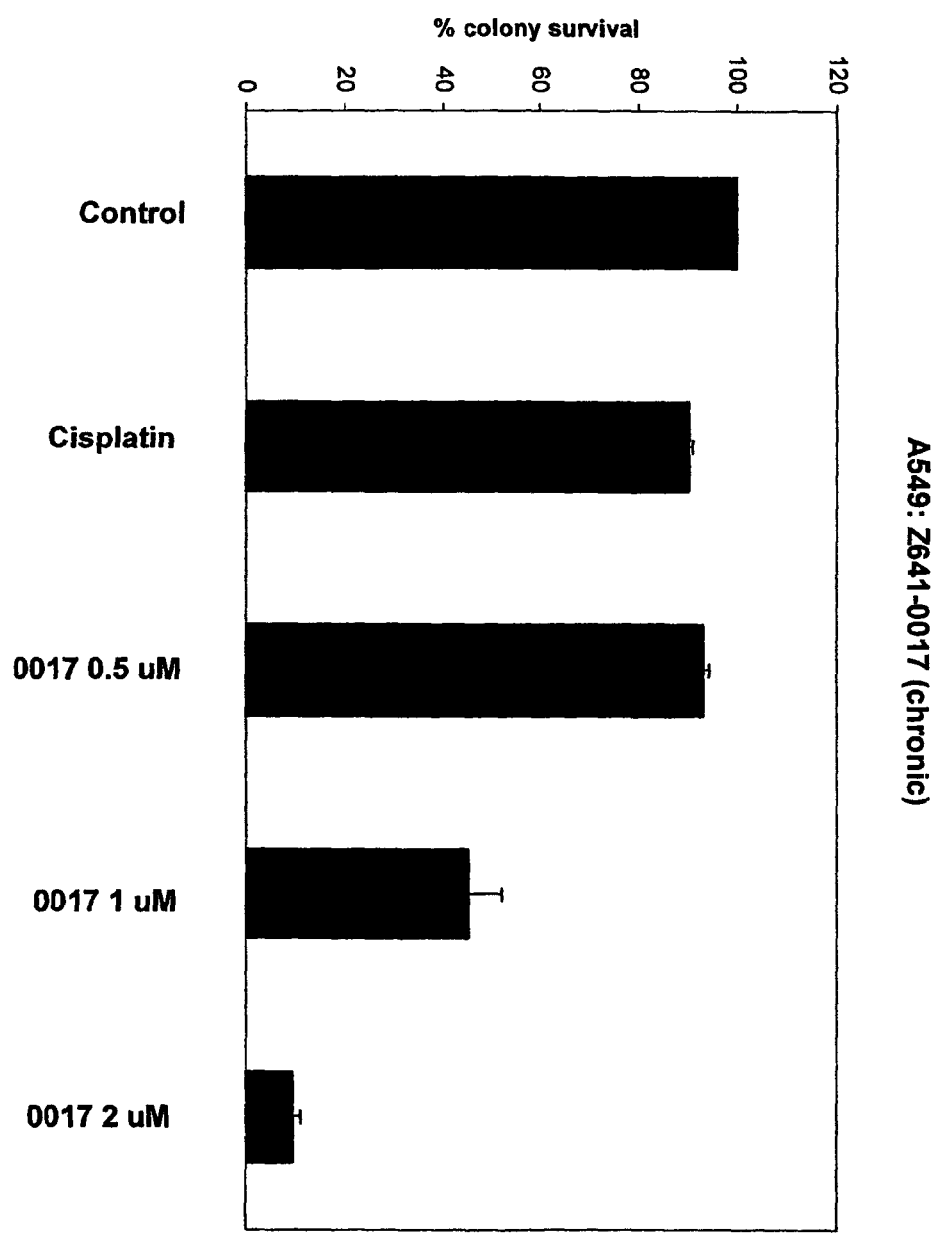
Figure 32:
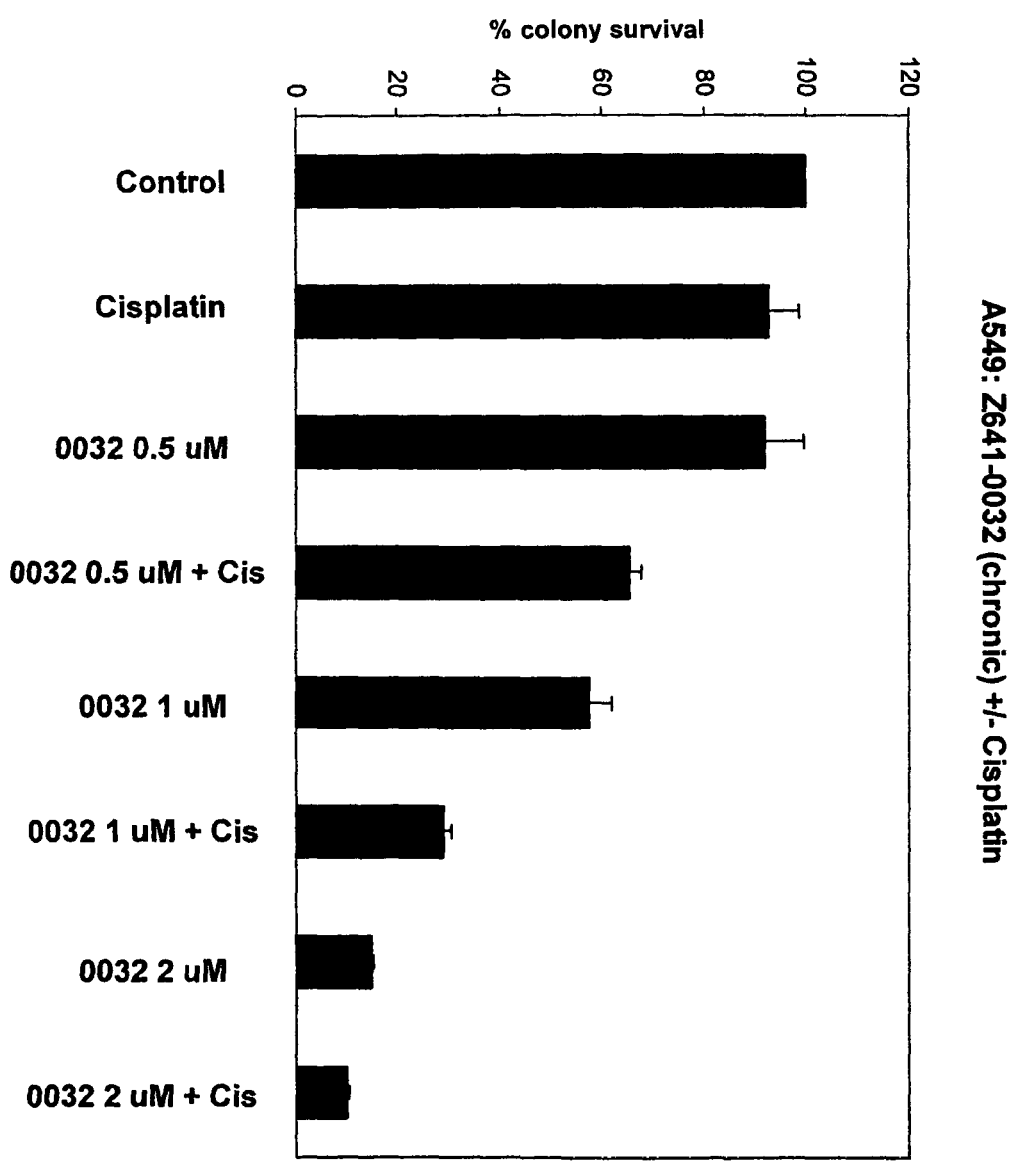
Figure 33:
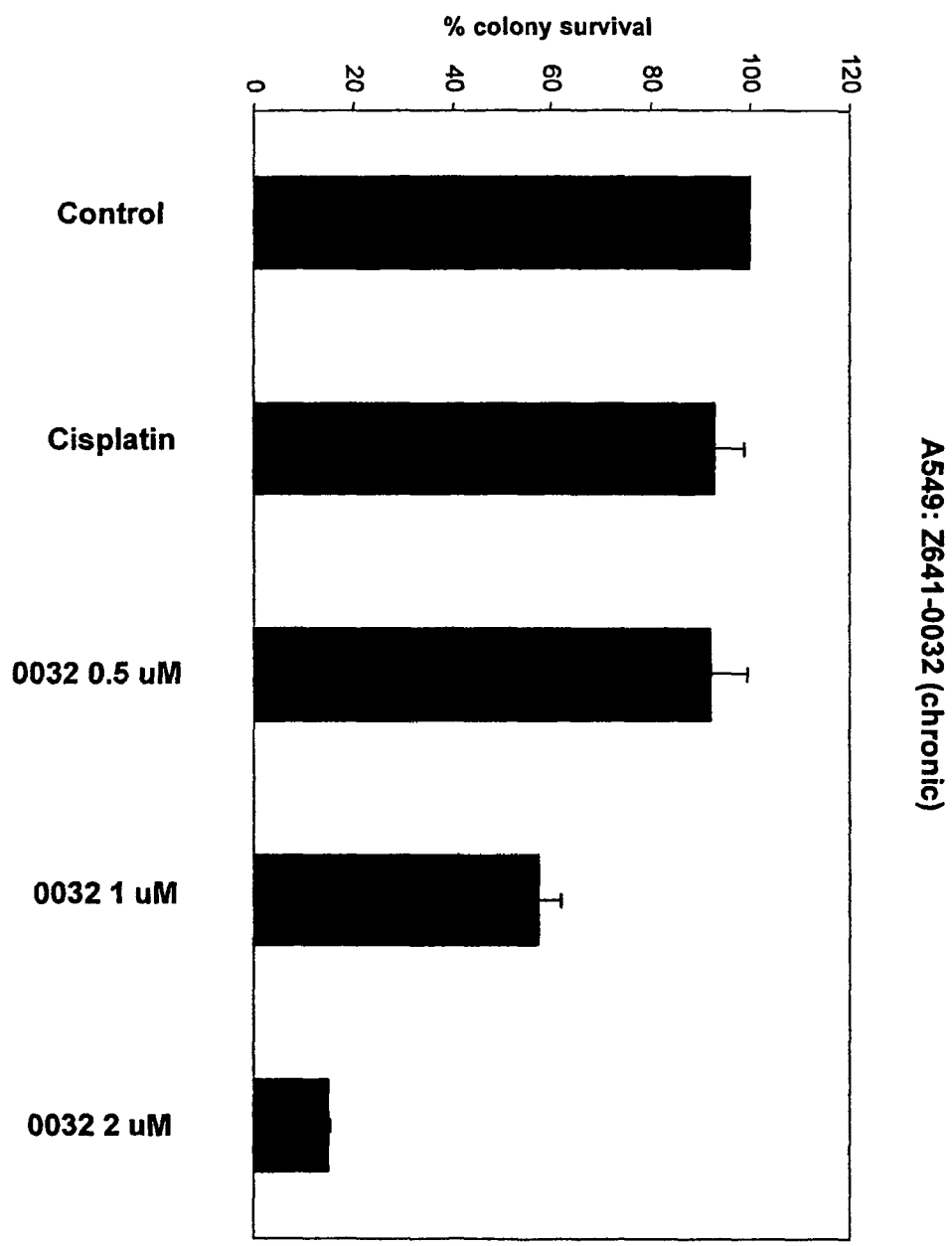
Figure 34:
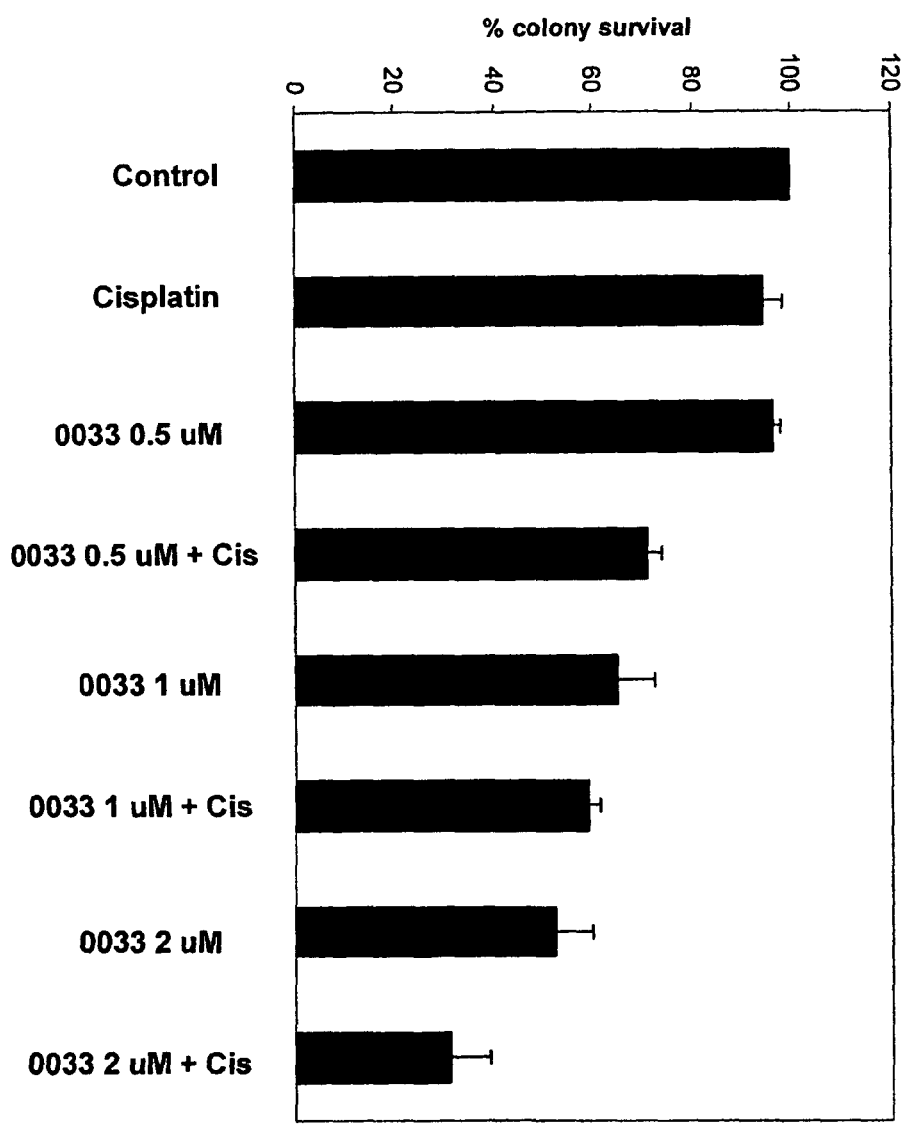
Figure 35:
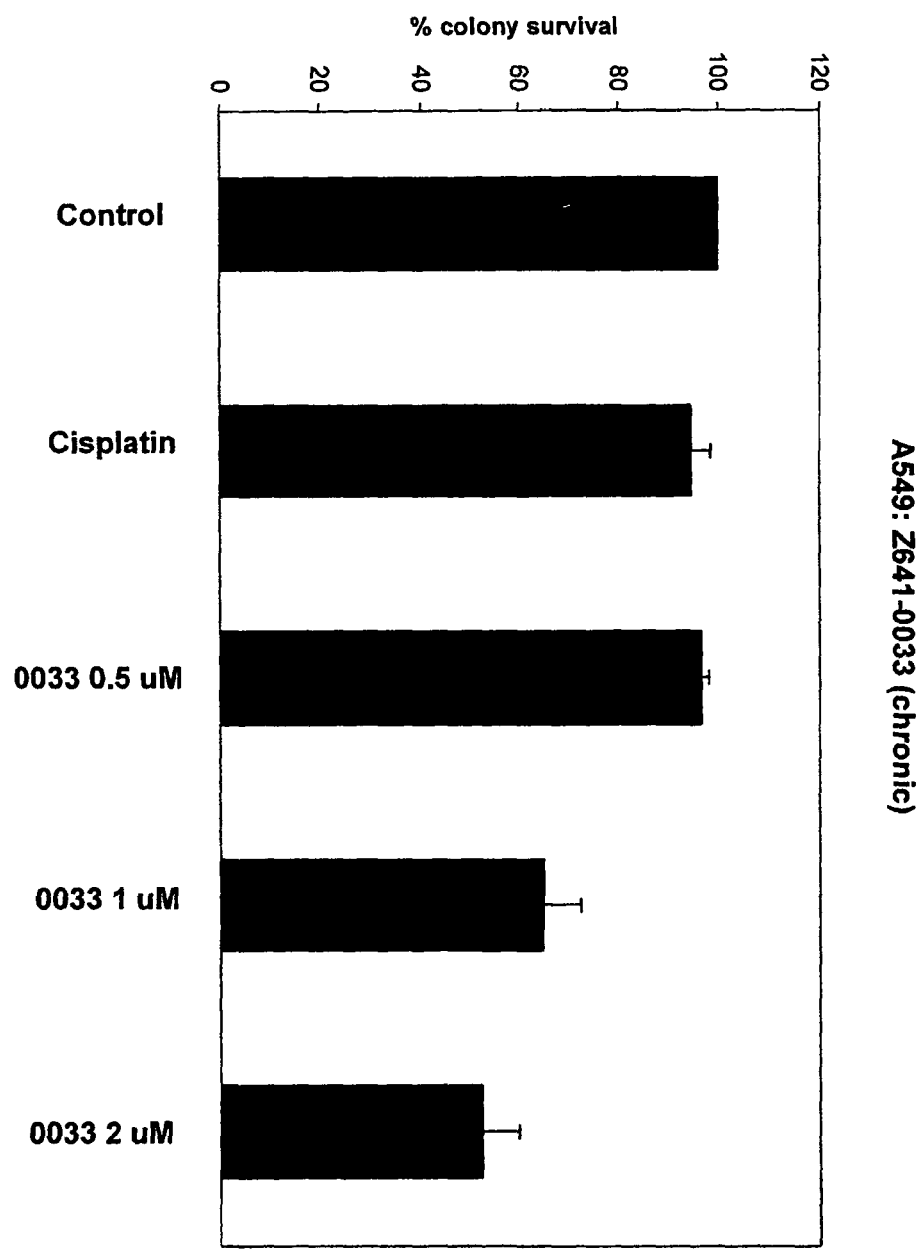
Figure 36:
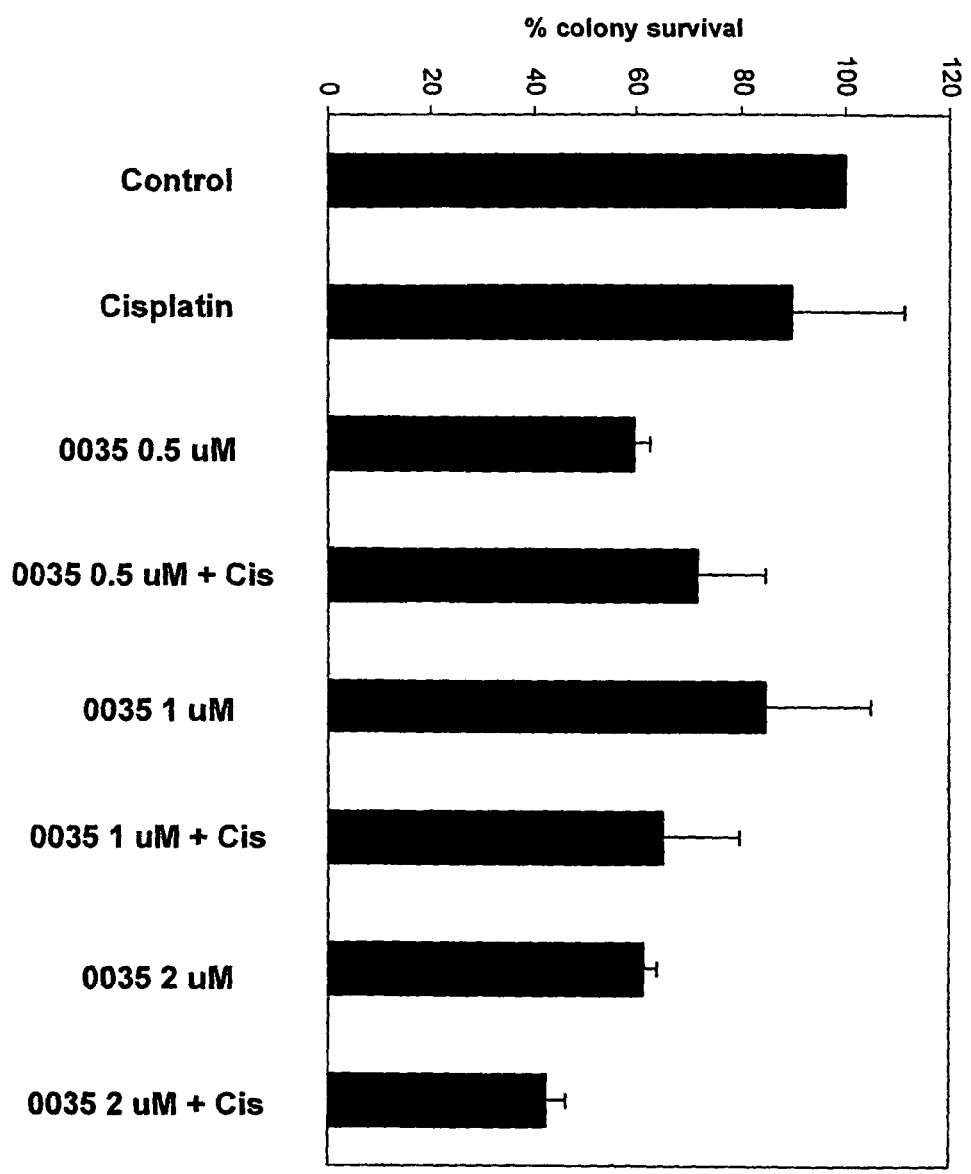
Figure 37:
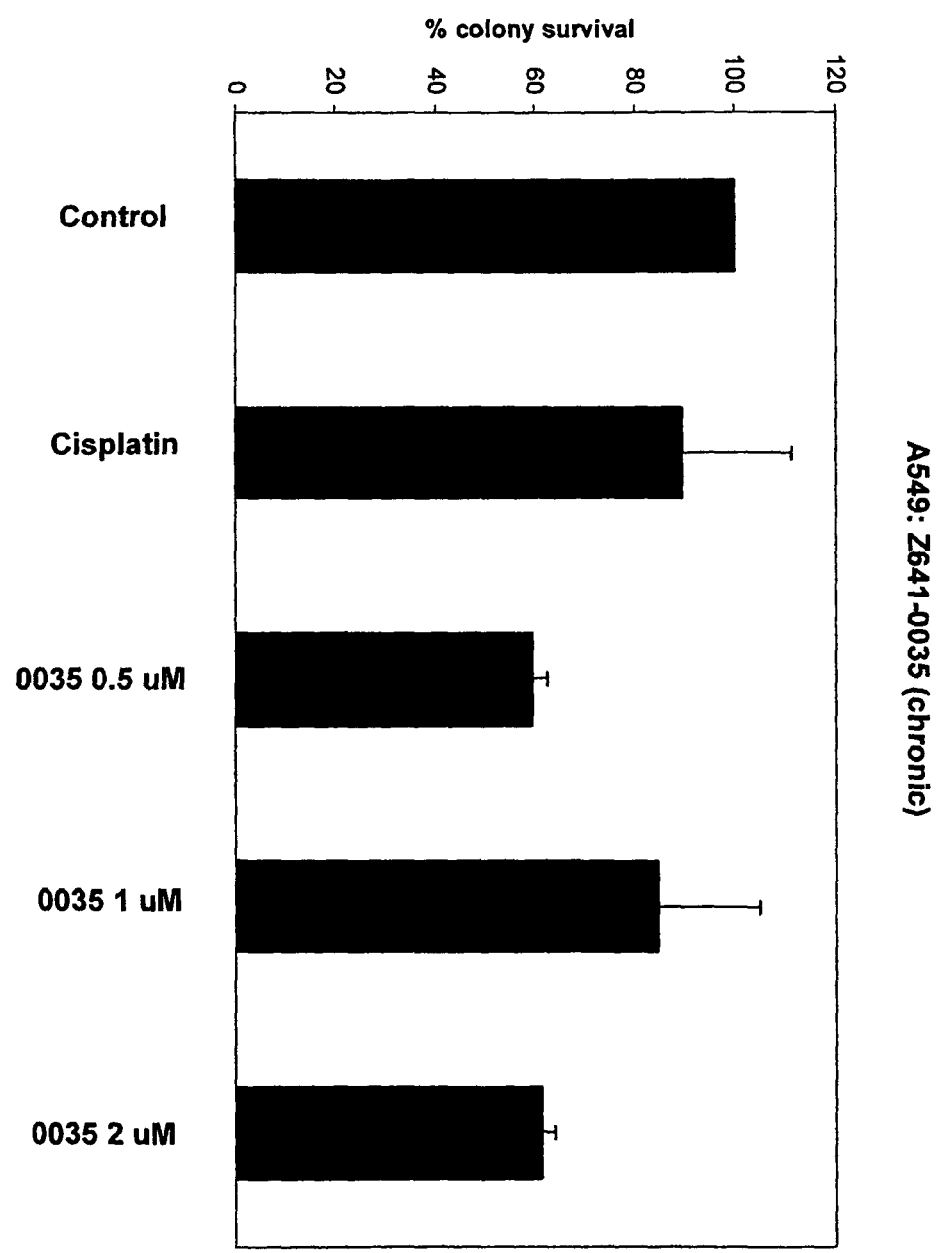
Figure 38:
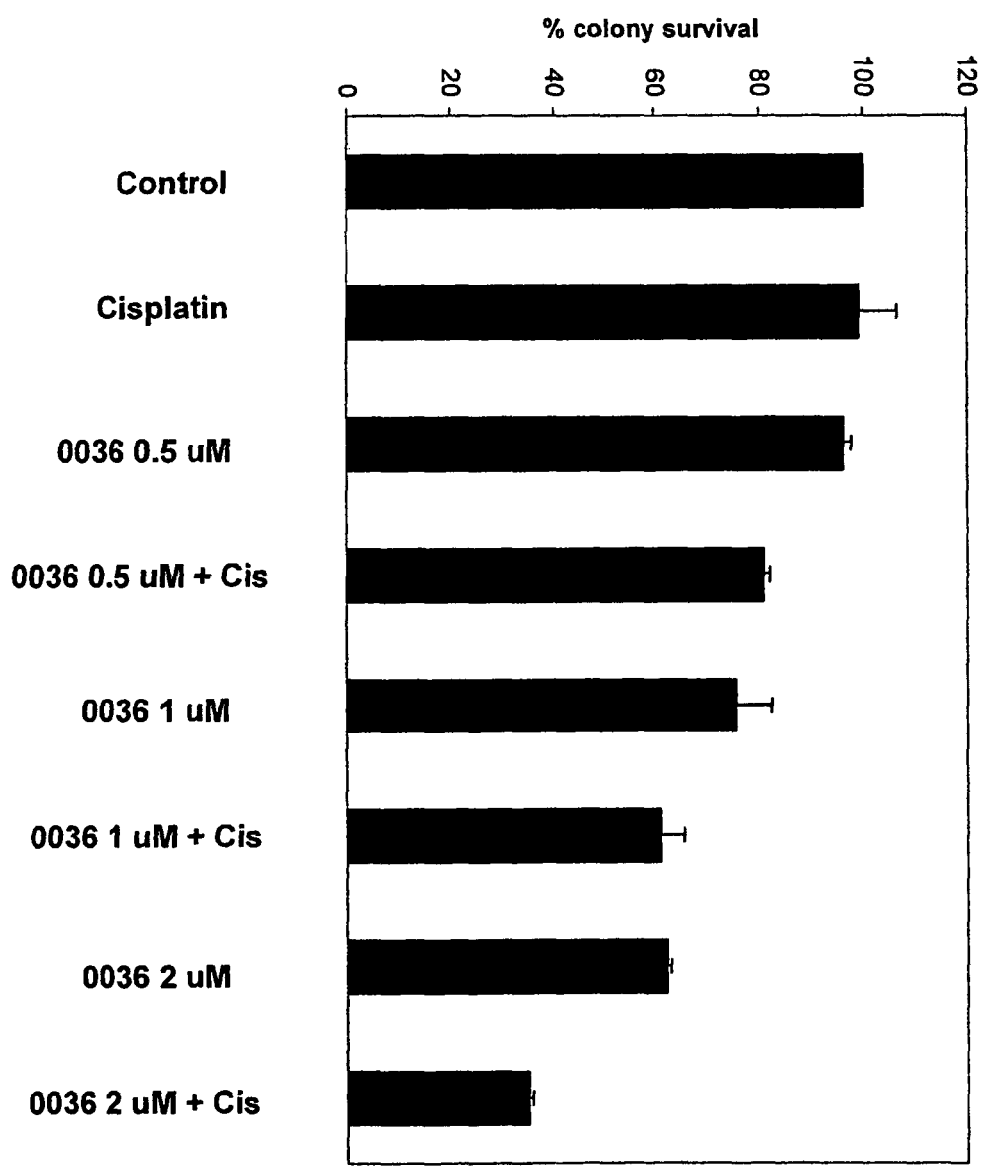
Figure 39:
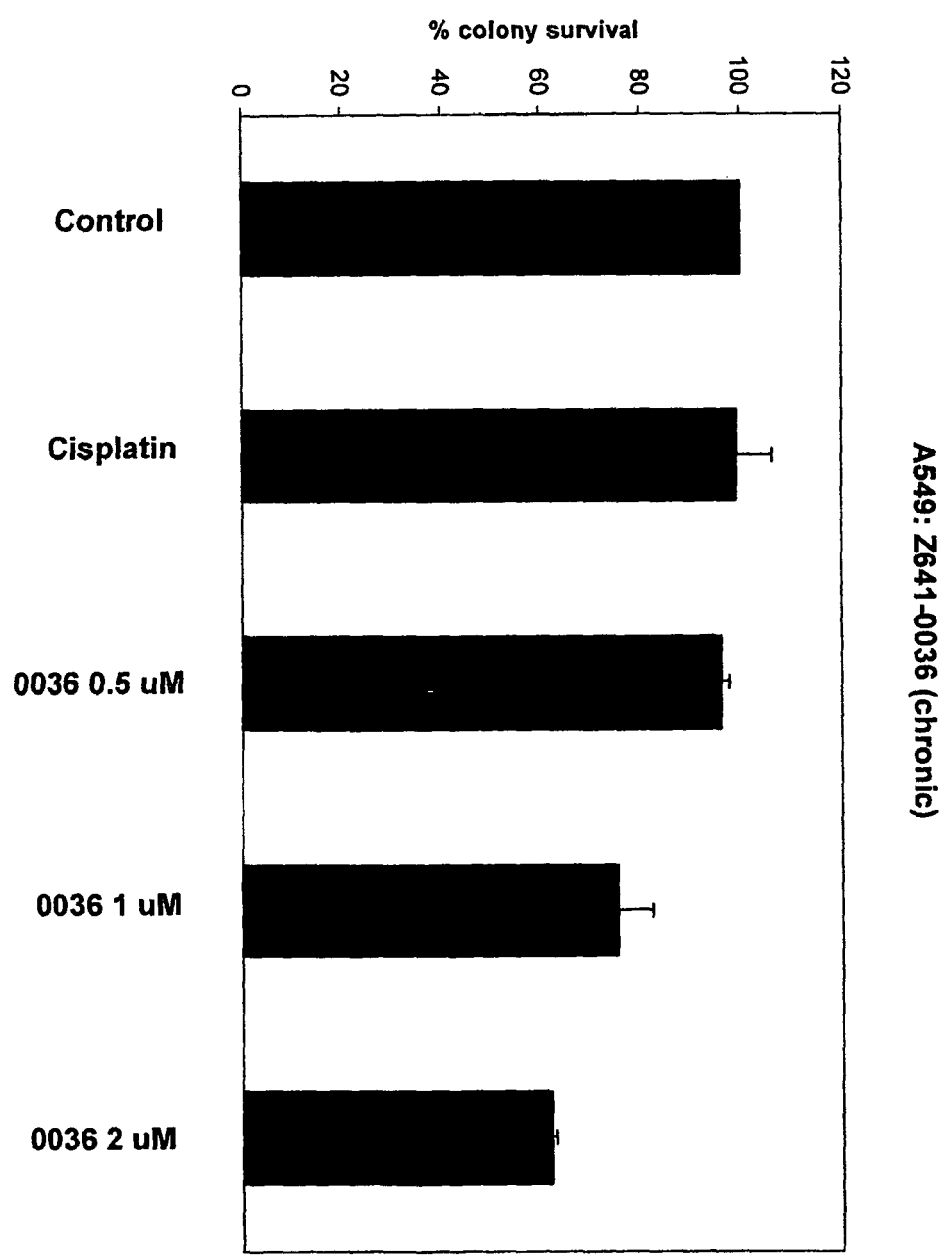
Figure 40:
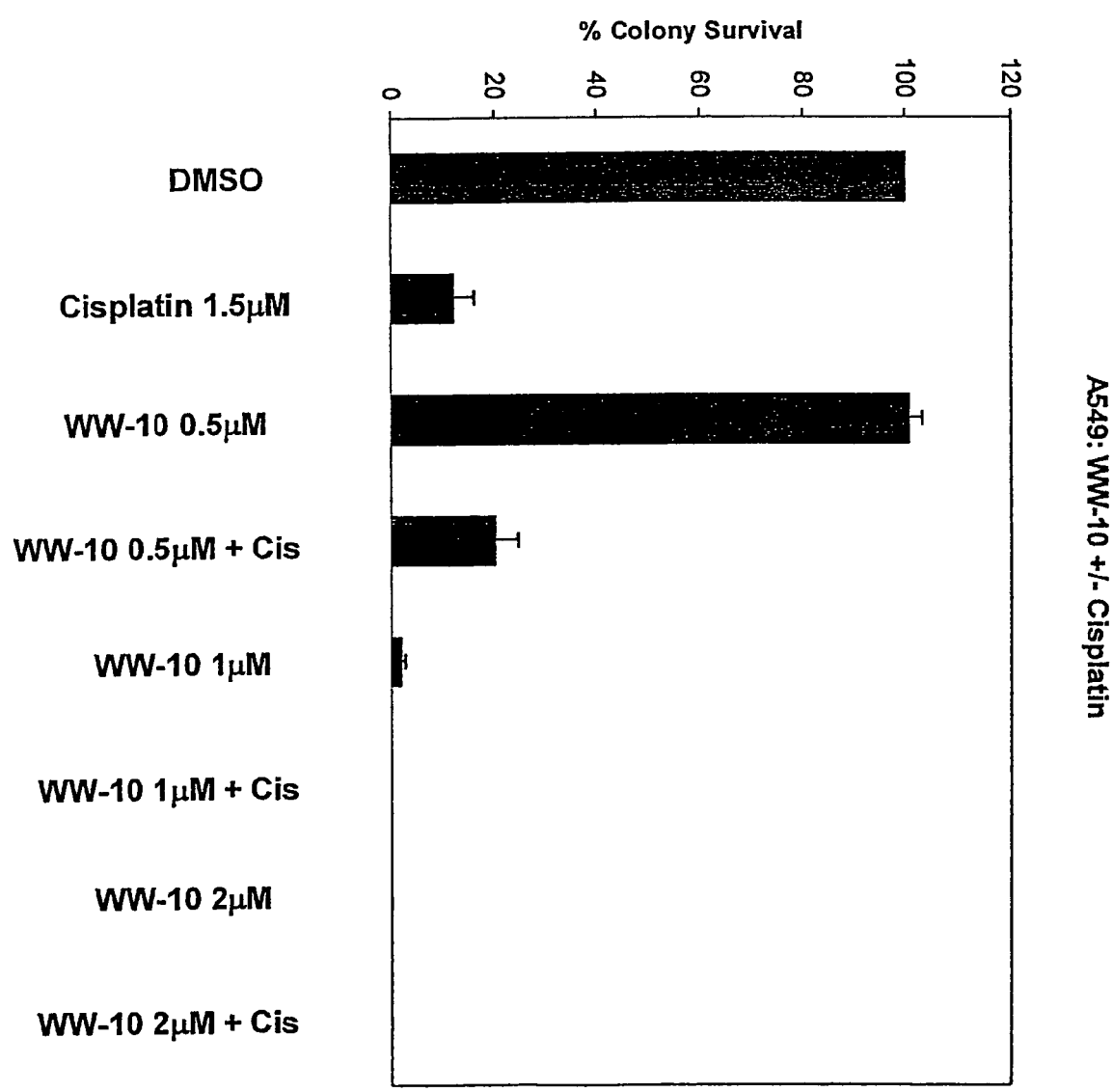
Figure 41:
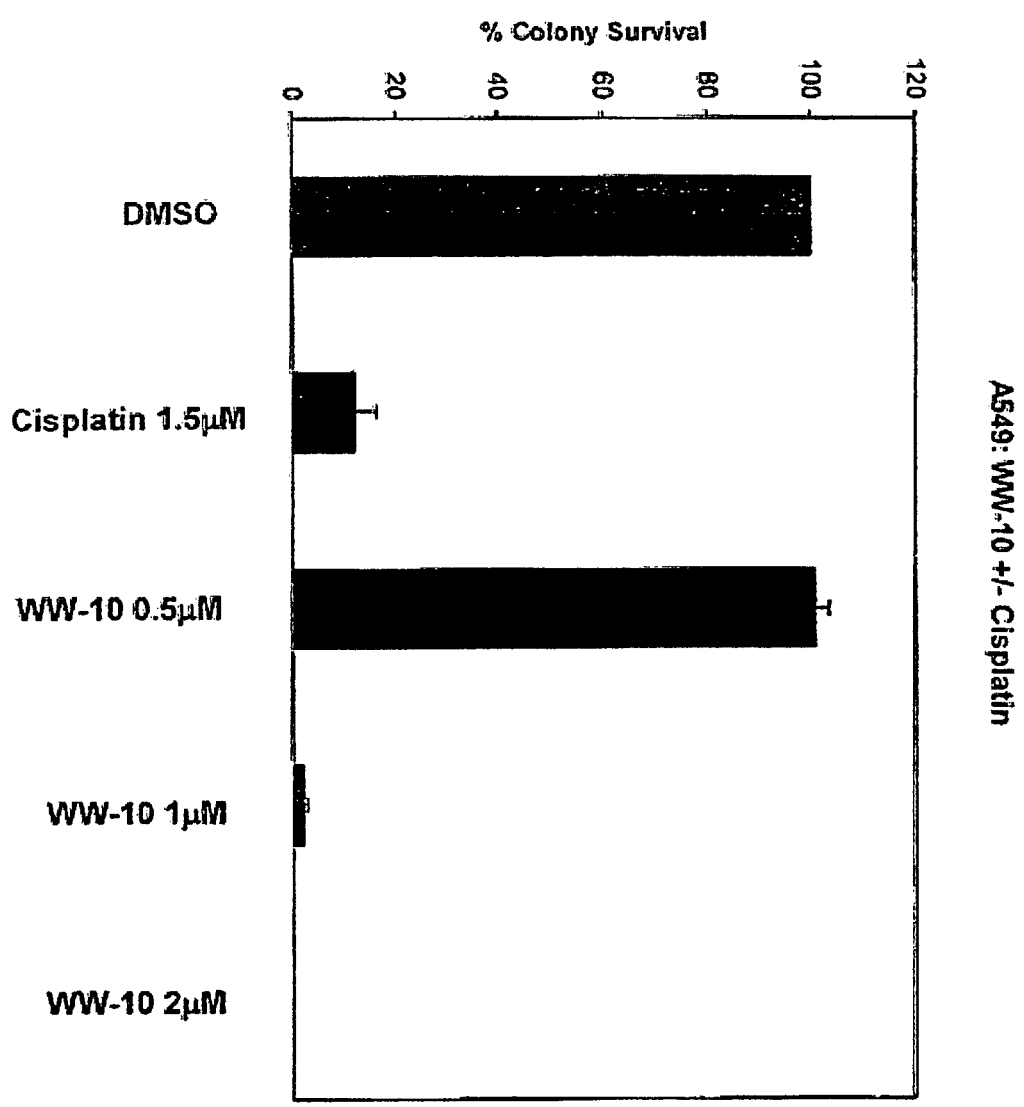
Figure 42:
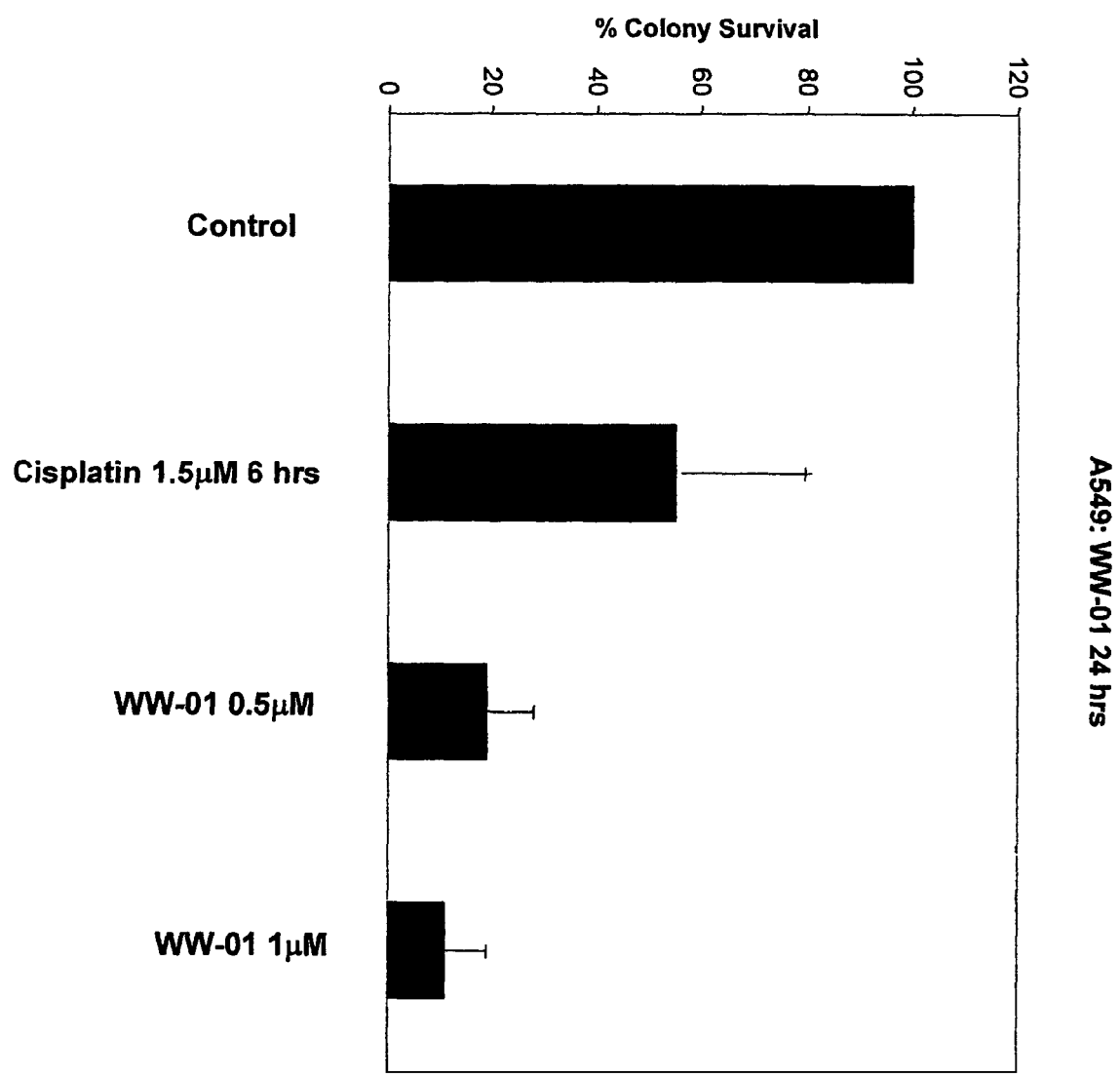

The compounds which are presented in FIGS. 17-19 hereof were tested in the colony formation assay as described above. Lung cancer cells were chosen for these assays because they are often resistant to most chemotherapeutic agents, and novel compounds to treat lung cancer patients are needed. Although cisplatin is one of the most active current drugs for treating lung cancer, the lung cancer cell line used is resistant to cisplatin. Colony formation assays were performed with the compounds constantly present over the time course of the assay with the exception of an overnight assay for compound Z641-0013, FIGS. 24-25. Fractional colony formation with the compound present was compared to colony formation in the presence of vehicle, and shown as a percentage of the control.

The cytotoxic activity of the bifunctional anti-neoplastic compounds Z641-0002, Z641-0011, Z641-0013, Z641-0016, Z641-0017, Z641-0032, Z641-0033, Z641-0035, Z641-0036, WW-10 and WW-01 (FIGS. 17-19) was tested against A549 lung cancer cells in colony formation assays as described above and shown in FIGS. 20-42. All of the compounds tested showed at least some cytotoxic activity alone or in combination with cisplating, consistent with these compounds being useful as anti-cancer agents both alone and in combination with other anticancer agents. Note that certain of the compounds evidenced cytotoxic activity in the colony forming assay at high dosages alone or in combination with cisplatin. In general, the effects of the compounds was dose dependent with greater cytotoxicity being evidenced at higher concentrations, although, not always (see Z641-0035, FIGS. 36-37).

The cytotoxic activity of the above bifunctional anti-neoplastic agents was tested against A549 lung cancer cells in colony formation assays. Colony formation assays were performed with these compounds constantly present over the time course of the assay (chronic). Fractional colony formation with the compound present was compared to colony formation in the presence of vehicle, and shown as a percentage of the control. In general, the compounds of the present application were present in the colony formation assay for longer periods, where the cisplatin was present for a shorter period. The cisplatin time period was chosen to mimic the physiologic serum presence of the drug in patients.

In most instances the cytotoxic effects of the tested compounds were greater than was cisplatin and with certain compounds (among them, Z641-0011, Z641-0013, Z641-0033, Z641-0035), the cytotoxic effects of the agent alone were significantly greater than was cisplatin alone. In most instances the compounds provided additive, even synergistic cytotoxic effects in combination with cisplatin. Compound WW-10 and WW-01 were especially active in combination with cisplatin at higher concentrations of WW-10 and WW-01. See FIGS. 40-42.

Figure 43:
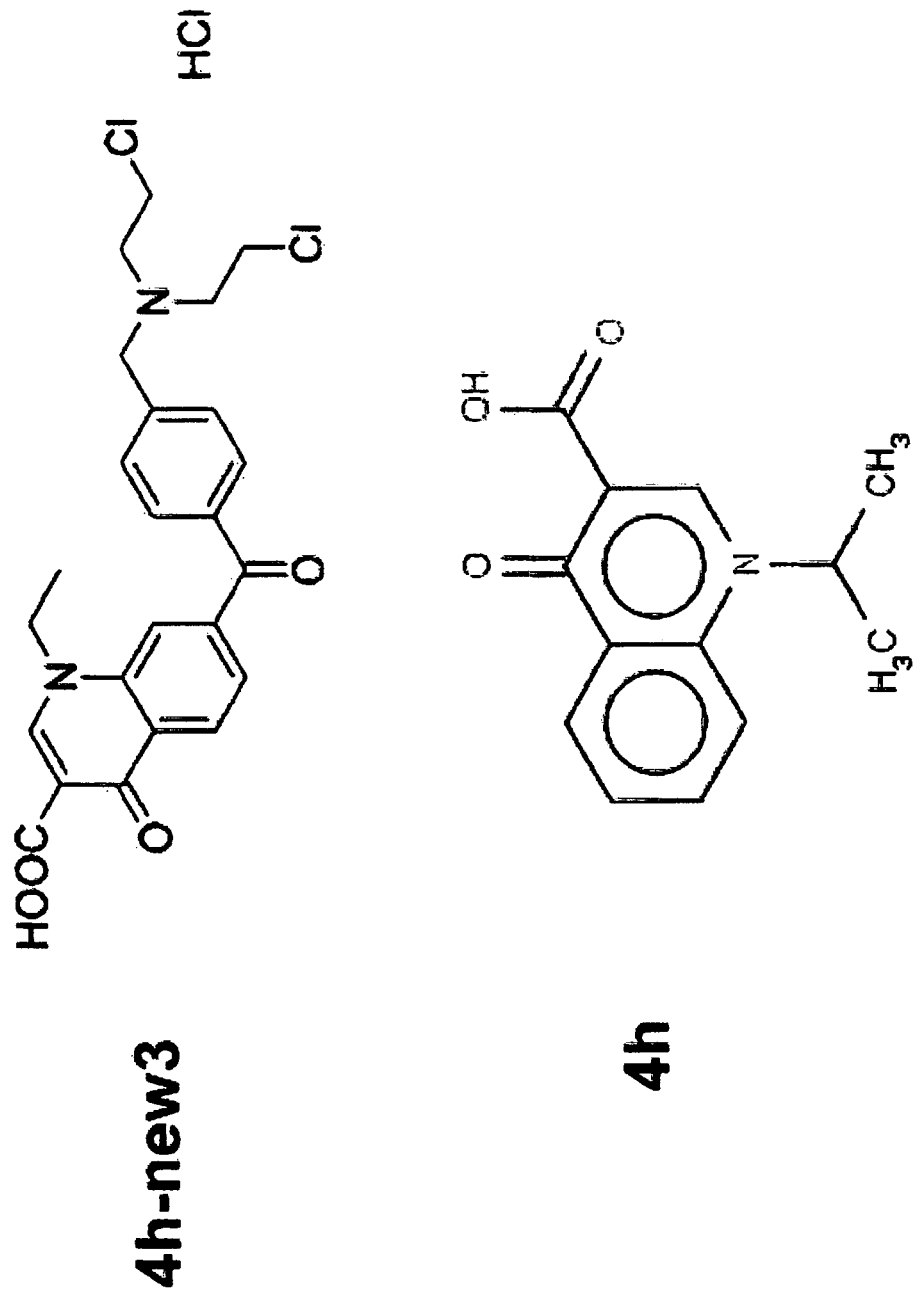
FIG. 43 shows the chemical structures of 4h-new3 and 4h, the two compounds used in the cytotoxicity experiments on Raji leukemia cells (FIG. 43) and NCI-H929 myeloma cells.
Figure 44:
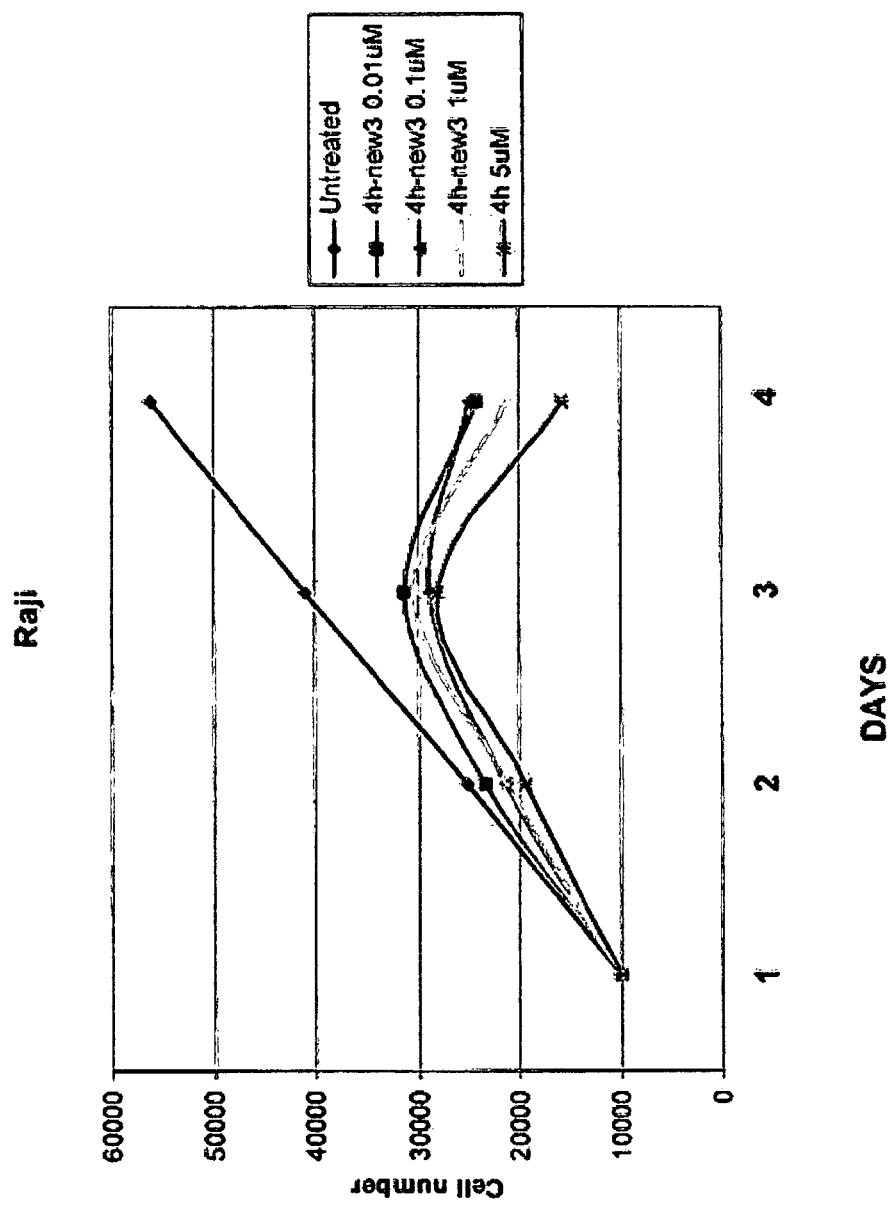
FIGS. 44-45 show the results of inhibition of Raji leukemia cells (FIG. 43) and NCI-H929 (FIG. 44) at varying concentrations using compounds 4h-new3 and 4h. The graphs evidence that the bifunction inhibitor 4h-new3 is significantly more effective at decreasing cancer cell proliferation than was the related monofunctional Metnase inhibitor 4h.
Figure 45:
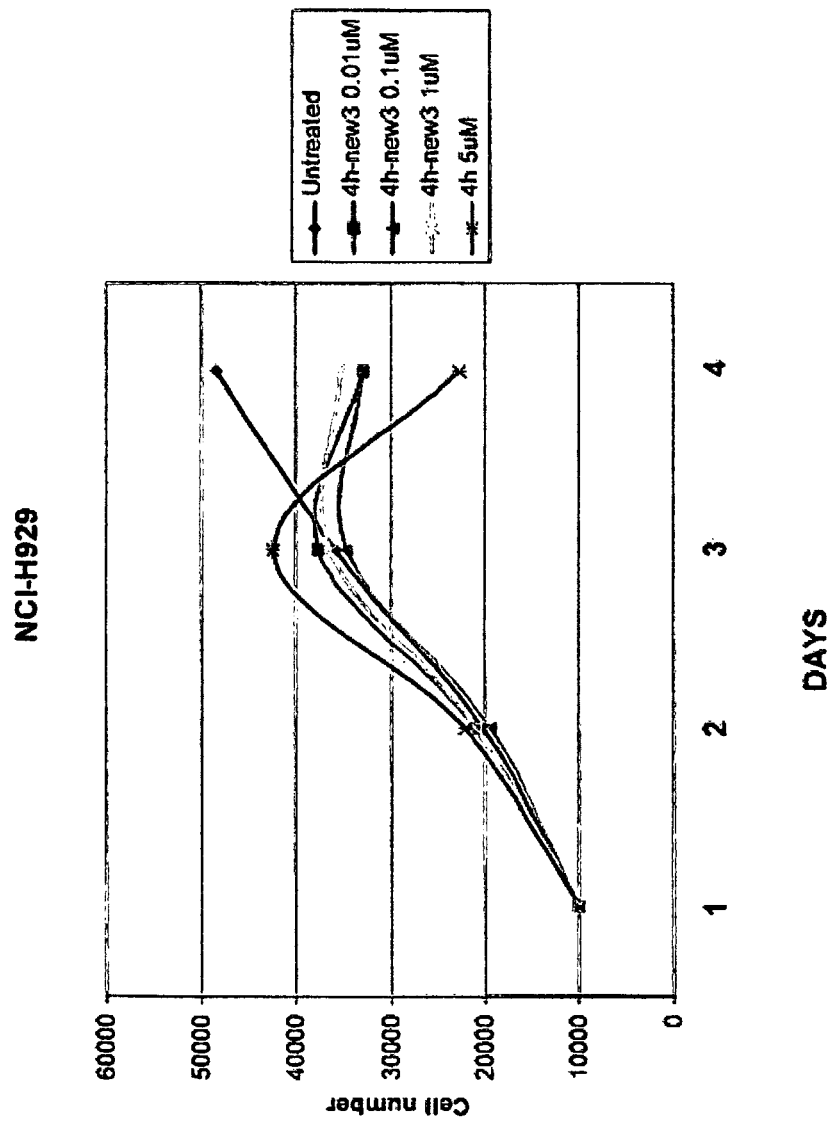

In separate experiments, the bifunctional Metnase inhibitor, 4h-new3 (see FIGS. 4 and 43) and the monofunctional Metnase inhibitor 4h (FIG. 1 and FIG. 43), were tested at varying concentrations to determine cytotoxic activity in Raji leukemia eels and MCI-H929 myeloma cells. The compounds were tested against vehicle control at varying concentrations in the above-described cancer cell lines. As evidenced by the graphs presented in FIGS. 44 and 45, compound 4h-new3 decreases the proliferation of these cell lines at levels below 1 μM and is significantly more effective at decreasing cancer cell proliferation than the related monofunctional Metnase inhibitor 4h.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. Any inconsistency between the material incorporated by reference and the material set for in the specification as originally filed shall be resolved in favor of the specification as originally filed. The foregoing detailed description and examples have been given for clarity of understanding only. No unnecessary limitations are to be understood therefrom. The invention is not limited to the exact details shown and described, for variations obvious to one skilled in the art will be included within the invention defined by the following claims.

All headings are for the convenience of the reader and should not be used to limit the meaning of the text that follows the heading, unless so specified.

What is claimed is:

1. A compound of the formula:

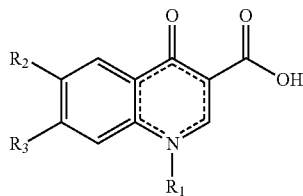

wherein:

$R_1$ is a $C_3$-$C_6$ hydrocarbon, a $(CH_2)_j$—$C_1$-$C_6$ acyl group which is optionally substituted, a $(CH_2)_j$—$NR^1R^2$ group wherein $R^1$ and $R^2$ are each independently H, or a $C_1$-$C_6$ alkyl group optionally substituted with halo or at least one hydroxyl group, an optionally substituted $(CH_2)_n$-amide group, an optionally substituted $(CH_2)_n$-thioamide group, an optionally substituted $(CH_2)_n$-aryl group or an optionally substituted $(CH_2)_n$-heterocyclic group;

Each j is independently 0, 1, 2, 3, 4, 5 or 6;
Each i' is independently 1, 2, 3, 4, 5 or 6;
Each n is independently 0, 1, 2, 3, 4, 5, or 6;
$R_2$ is H, halo, or an, optionally substituted $C_1$-$C_6$ hydrocarbon which itself is optionally substituted with a —$C_0$-$C_6$-hydrocarbon-$NR^cR^d$ group, where $R^c$ and $R^d$ are each independently a —$(CH_2)_{iw}$—W group where each iw is independently 1, 2, 3, 4, 5 or 6 and W is a halo group;

$R_3$ is —N(H)$R^a$, —N(H)C(=O)$R^a$, —C(=O)$R^b$, a

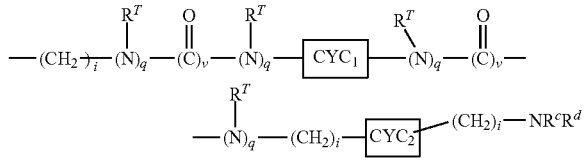

group or a —$C_0$-$C_6$-hydrocarbon-$NR^cR^d$ group which is optionally substituted;

each of $R^c$ and $R^d$ is independently the same as described above;

each i is independently 0, 1, 2, 3, 4, 5, or 6;
each $R^T$ is independently H or a $C_1$-$C_3$ alkyl group which is optionally substituted with one or two hydroxyl groups;
each q is independently 0 or 1;
each v is independently 0 or 1;
CYC₁ is a first cyclic hydrocarbon group which is optionally substituted;
CYC₂ is a second cyclic hydrocarbon group which is optionally substituted;
$R^a$ is

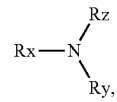

where $R_x$ is a $C_1$-$C_6$ hydrocarbon which is optionally substituted, an optionally substituted $(CH_2)_j$—$C_1$-$C_6$ ether or thioether group, an optionally substituted $(CH_2)_j$—$C_1$-$C_6$ acyl group, an optionally substituted $(CH_2)_n$-amide group, or an optionally substituted $(CH_2)_n$-thioamide group;

$R_y$, and $R_z$ are each independently, an optionally substituted $C_1$-$C_6$ hydrocarbon, an optionally substituted $(CH_2)_j$—$C_1$-$C_6$ ether or thioether group, an optionally substituted $(CH_2)_j$—$C_1$-$C_6$ acyl group, a $(CH_2)_j$—$NR^1R^2$ group wherein $R^1$ and $R^2$ are each independently H, or a $C_1$-$C_6$ alkyl group optionally substituted with halo or at least one hydroxyl group, an optionally substituted $(CH_2)_n$-amide group, or an optionally substituted $(CH_2)_n$-thioamide group;

$R^b$ is an optionally substituted aryl, an optionally substituted $(C_0$-$C_6$ hydrocarbon)-aryl, an optionally substituted —O-aryl, an optionally substituted $(C_0$-$C_6$ hydrocarbon)-aryl, an optionally substituted —O-hetaryl wherein each $R^b$ group is optionally substituted with one or more substituents, each of which is independently $R^a$ as defined above, halo, $C_1$-$C_6$ hydrocarbon, —$C_1$-$C_6$ haloalkyl, —O—$C_1$-$C_6$ alkyl, —O—$C_1$-$C_6$ haloalkyl, oxo (=O), or —$CO_2R_m$, where $R_m$ is —H or —$C_1$-$C_6$ alkyl which is optionally substituted with at least one hydroxyl group, or $R^b$ may be an optionally substituted $C_0$-$C_6$alkyl-W—X—Z group, where W is an optionally substituted carbocyclic aryl or heteroaryl group;

X is absent, S, O or a —N($R^N$)— group where $R^N$ is H or a $C_1$-$C_3$ alkyl group which is optionally substituted with one or two hydroxyl groups; and Z is absent, a carbocyclic aryl or heteroaryl group each of which group is further optionally substituted with one or more substituents, each of which substituent is independently $R^{a'}$, halo, $C_1$-$C_6$ hydrocarbon, —$C_1$-$C_6$ haloalkyl, —O—$C_1$-$C_6$ alkyl, —O—$C_1$-$C_6$ haloalkyl, oxo (=O), or —$CO_2R_m$, wherein $R^{a'}$ is

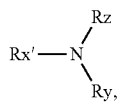

where Rx' is absent or $R_x$, and Ry and Rz are the same as described above, or a pharmaceutically acceptable salt, solvate or polymorph thereof.

2. The compound according to claim 1 wherein said chemical compound is according to the chemical structure:

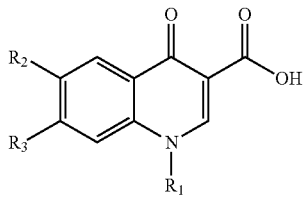

or a pharmaceutically acceptable salt, solvate or polymorph thereof.

3. The compound according to claim 1 wherein $R_3$ is —N(H)$R^a$, —N(H)C(=O)$R^a$, or —C(=O)$R^b$, a

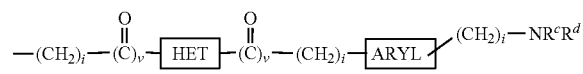

group, a

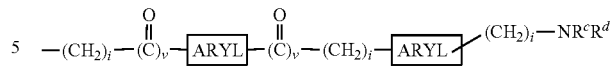

group or a

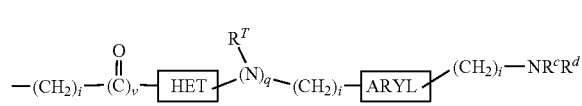

group

Where HET is a non-aromatic heterocyclic group which is optionally substituted; ARYL is a carbocyclic aryl or heteroaryl group;

Each i is independently 0, 1, 2, 3, 4, 5 or 6;

q is 0 or 1;

Each v is independently 0 or 1;

and $R^c$ and $R^d$ are each independently a $C_1$-$C_3$ alkyl group which is substituted with at least one chloro group, and where $R^b$ is an carbocyclic aryl group which is substituted in the meta- or para-position by a $R^a$ group where $R_x$ is a —(CH$_2$)$_i$— group, and each of $R_y$ and $R_z$ is a —CH$_2$CH$_2$Cl group.

4. The compound according to claim 1 wherein $R^c$ and $R^d$ are each a —CH$_2$CH$_2$Cl group.

5. The compound according to claim 3 wherein $R_3$ is

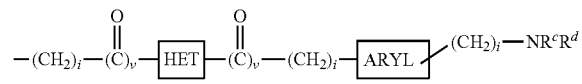

and i is 0, 1 or 2.

6. The compound according to claim 1 wherein $R_1$ is a $C_3$ alkyl group.

7. The compound according to claim 6 wherein said $C_3$ alkyl group is an isopropyl group or cyclopropyl group.

8. The compound according to claim 1 wherein $R_1$ is a cyclopropyl group.

9. A compound of claim 1 according to the chemical structure:

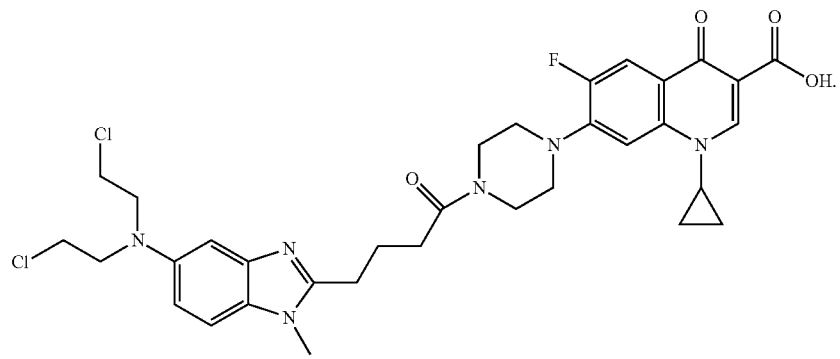 [SMILES: Cn1c(CCCC(=O)N2CCN(c3cc4c(cc3F)c(=O)c(C(=O)O)cn4C3CC3)CC2)nc2cc(N(CCCl)CCCl)ccc21]

10. A pharmaceutical composition comprising an effective amount of a compound according to claim 1 and at least one pharmaceutically acceptable carrier, additive, or excipient, optionally in combination with an additional agent useful in treating cancer.

11. A pharmaceutical composition comprising an effective amount of a compound according to claim 2 and at least one pharmaceutically acceptable carrier, additive, or excipient, optionally in combination with an additional agent useful in treating cancer.

12. A pharmaceutical composition comprising an effective amount of a compound according to claim 3 and at least one pharmaceutically acceptable carrier, additive, or excipient, optionally in combination with an additional agent useful in treating cancer.

13. A pharmaceutical composition comprising an effective amount of a compound according to claim 9 and at least one pharmaceutically acceptable carrier, additive, or excipient, optionally in combination with an additional agent useful in treating cancer.

* * * * *